US008038986B2

(12) United States Patent
Schofield

(10) Patent No.: US 8,038,986 B2
(45) Date of Patent: Oct. 18, 2011

(54) IMMUNOGENIC COMPOSITIONS AND DIAGNOSTIC AND THERAPEUTIC USES THEREOF

(75) Inventor: Louis Schofield, Gisborne (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 558 days.

(21) Appl. No.: 10/522,494

(22) PCT Filed: Jul. 25, 2003

(86) PCT No.: PCT/AU03/00944
§ 371 (c)(1),
(2), (4) Date: Sep. 6, 2005

(87) PCT Pub. No.: WO2004/011026
PCT Pub. Date: Feb. 5, 2004

(65) Prior Publication Data
US 2006/0147476 A1    Jul. 6, 2006

(51) Int. Cl.
*A61K 49/00* (2006.01)
*A61K 39/02* (2006.01)
*A61K 39/00* (2006.01)

(52) U.S. Cl. .... 424/9.1; 424/9.2; 424/130.1; 424/184.1; 424/234.1; 424/265.1; 424/268.1; 435/4; 435/7.1; 435/7.22

(58) Field of Classification Search ............ 424/9.1, 424/9.2, 130.1, 184.1, 234.1, 265.1, 268.1; 435/4, 7.1, 7.22
See application file for complete search history.

(56) References Cited

U.S. PATENT DOCUMENTS
2006/0089330 A1    4/2006    Seeberger et al.

FOREIGN PATENT DOCUMENTS
DE    43 11 580 C1    8/1994
WO    WO 00/15254    3/2000
WO    WO 00/24406    5/2000

OTHER PUBLICATIONS

Naik R.S. et al., "Glycosylphosphatidylinositol Anchors of *Plasmodium falciparum*: Molecular Characterization and Naturally Elicited Antibody Response that May Provide Immunity to Malaria Pathogenesis", *The Journal of Experimental Medicine* 192(11):1563-1575 (2000).
Vafai A., "Boosting Immune Response with a Candidate Varicella-Zoster Virus Glycoprotein Subunit Vaccine", *Vaccine* 13(14):1336-1338 (1995).
Romero G. et al., "Anti-Inositolglycan Antibodies Selectively Block Some of the Actions of Insulin in Intact $BC_3H1$ Cells", *Proc. Natl. Acad. Sci. USA* 87:1476-1480 (1990).
Schofield L. et al., "Synthetic GPI as a Candidate Anti-toxic Vaccine in a Model of Malaria", *Nature* 418:785-789 (2002).
Schofiled, L, et al., "Synthetic GPI as a Candidate Anti-Toxic Vaccine in a Model of Malaria" *Nature* (2002) pp. 785-789, vol. 418.

*Primary Examiner* — Rodney P. Swartz
(74) *Attorney, Agent, or Firm* — Scully, Scott, Murphy & Presser, P.C.

(57) ABSTRACT

The present invention relates to a method of inducing an immune response to a parasite utilizing an immunogenic composition comprising a glycosylphosphatidylinositol ("GPI") inositolglycan domain or its derivative or equivalent. The present invention is useful as a prophylactic and/or therapeutic treatment for microorganism infections of mammals such as parasite infections and particularly infection by *Plasmodium* species. The invention also provides a method of monitoring, or qualitatively or quantitatively assessing an immune response to a microorganism such as a parasite. More particularly, this aspect of the present invention is directed to assessing said immune response utilizing a GPI inositoglycan domain or its derivative or equivalent, which facilitates the qualitative and/or quantitative analysis of anti-GPI antibodies in a biological sample, the identification of unique specificities of antibodies, epitope specific screening or the rational design of immunogenic molecules and the generation, thereby, of functionally effective immunointeractive molecules.

40 Claims, 24 Drawing Sheets

| Protein | MW | Maleimide groups | Conjugation Ratio | Glycan (ng / ug) |
|---|---|---|---|---|
| OVA | 45 000 | 8 moles per mole OVA | 3 : 1 (molar) | 84 |
| KLH | 8 000 000 | 479 moles per mole KLH | 191 : 1 (molar) | 28 |
| BSA | 67 000 | 17 moles per mole BSA | NA | - |

Figure 18

| Molar Excess Synthetic Glycan | Percentage reduction |
|---|---|
| 0 | 0 |
| 25 | 76 |
| 50 | 89 |
| 100 | 95 | ps
IMMUNOGENIC COMPOSITIONS AND DIAGNOSTIC AND THERAPEUTIC USES THEREOF

Cross-Reference to Related Application:

This application is the §371 national phase of International Application PCT/AU2003000944, filed Jul. 25, 2003, which claims the benefit of U.S. Provisional Application No. 60/398,607, filed Jul. 26, 2002.

FIELD OF TH INVENTION

The present invention relates generally to a method of eliciting or otherwise inducing an immune response to a microorganism and compositions for use therein. More particularly, the present invention relates to a method of inducing an immune response to a parasite utilising an immunogenic composition comprising a glycosylphosphatidylinositol (referred to herein as "GPI") inositolglycan domain or its derivative or equivalent. The present invention is useful, inter alia, as a prophylactic and/or therapeutic treatment for microorganism infections of mammals such as, for example, parasite infections and in particular infection by *Plasmodium* species.

In another aspect the invention provides a method of diagnosing, monitoring, screening for or otherwise qualitatively or quantitatively assessing an immune response to a microorganism and, in particular, a parasite. More particularly, this aspect of the present invention is directed to assessing said immune response utilising a GPI inositoglycan domain or its derivative or equivalent. The development of this aspect of the present invention facilitates, inter alia, the qualitative and/or quantitative analysis of anti-GPI antibodies in a biological sample, the identification and/or isolation of unique specificities of antibodies (such as those which bind a parasite derived toxin or the parasite itself), epitope specific screening or the rational design of immunogenic molecules and the generation, thereby, of functionally effective immunointeractive molecules.

BACKGROUND OF TH INVENTION

Bibliographic details of the publications referred to by author in this specification are collected at the end of the description.

The reference to any prior art in this specification is not, and should not be taken as, an acknowledgment or any form of suggestion that that prior art forms part of the common general knowledge in Australia.

The malaria parasite is considered to be one of the single most serious infectious agents in the world, infecting 5% of the global population and causing serious mortality and morbidity to sensitive populations and hampering socio-economic development.

Severe malaria infection shares several clinical features in common with bacterial septic shock. In both conditions, the excess production by macrophages of pro-inflammatory cytokines such as Tumor Necrosis Factor (TNF), Interleukin-1 (IL-1) and IL-6 occurs in response to malaria "toxins" and lipopolysaccharide (LPS), respectively, leading to complications such as fever and hyperpyrexia, leukopenia, thrombocytopenia, hypotension, disseminated intravascular coagulation, leukocyte infiltration, vascular permeability and multi-organ inflammation, which may lead eventually to death. Thus, many signs, symptoms and syndromes in acute and severe malaria infection result from the activity of a parasite "toxin" released into the circulation during the blood-stage developmental cycle of the infection.

GPI has been identified as a candidate toxin of parasite origin (Schofield, L. and Hackett, F. (1993) *Journal of Experimental Medicine* 177:145-153 and Tachado, S. D., Gerold, P., Schwarz, R., Novakovic, S., McConville, M., and Schofield, L. (1997) *Proceedings of the National Academy of Sciences USA* 94:4022-4027). The structure of the molecule has been elucidated (Gerold, P., Dieckman-Schuppert A. and Schwarz, R. T. (1992) *Bio. Soc. Trans.* 29:297 and Gerold, P., Schofield, L., Brackman, M., Holder, A. A., Schwarz, R. T. (1996) *Mol. Biochem. Parasitol* 75:131) and it comprises a lipidic domain and a glycan domain. Intact GPI occurs in two closely related forms, Pfg1α (NH—$CH_2$—$CH_2$—$PO_4$-(Manα1-2)-6Manα1-2Manα1-6Manα1-4GlcN-$H_2$α1-6 (myristoyl)-myo-Inositol-1-$PO_4$-dipalmitoylglycerol), and Pfg1β (NH—$CH_2$—$CH_2$—$PO_4$-6Manα1-2Manα1-6Manα1,4GlcN-$H_2$α1-6(myristoyl)-myo-Inositol-1-$PO_4$-dipalmitoylglycerol).

The parasite derived GPI molecule regulates host cell function and gene expression in various tissues by activating endogenous GPI-based signal transduction pathways, involving hydrolysis into second messengers and the activation of both tyrosine and serine/threonine kinases. This leads to the activation of the NFκB/c-rel family of transcription factors, which regulate the expression of numerous pro-inflammatory loci implicated in malarial pathology, such as TNF, IL-1, iNOS and ICAM-1.

The toxin theory of malarial pathogenesis can be ascribed to Camillo Golgi, in 1886, who hypothesized that the proximal cause of the febrile paroxysm was a released toxin of parasite origin (Golgi, C. (1886) *Arch. Sci. Med.* (*Torino*) 10:109). Clark proposed that the systemic inflammation of malaria infection resulted from a functional malarial endotoxin, and suggested that this agent exerts systemic effects largely through the induction of endogenous pyrogens of host origin. Clark correctly identified TNF as a major host mediator of disease (Clark, I. A. (1978) *Lancet* 2:75 and Clark, I. A., Virelizier, J.-L., Carswell, E. A., and Wood, P. R. (1981) *Infect. Immun.* 32:1058). Consequently, the production of this and related pyrogenic cytokines (IL-1, IL-6) from monocyte/macrophages is often taken as a useful surrogate marker for the initiation of pathological processes in malaria infection. John Playfair and his colleagues extended this work to show that crude extracts of rodent malaria parasites could induce macrophages to secrete TNF in vitro (Bate, C. A., Taverne, J., and Playfair, J. H. (1988) *Immunology* 64:227 and Bate, C. A., Taverne, J., and Playfair, J. H. (1989) *Immunology* 66:600) and inferred that the toxin included a phospholipid moiety. Nonetheless, prior to the advent of the present invention, the specific biochemical identity of the parasite toxin, and its mechanism of action, have remained obscure.

In work leading up to the present invention, the inventors investigated the use of portions of GPI to induce protective immunity against malarial pathology. The inventors have surprisingly discovered that GPI portions which exclude the lipidic domain induce protective immunity whereas portions carrying the lipidic domain do not.

In still another surprising aspect, it has been determined that the above-described GPI portions can be effectively utilised to facilitate the qualitative and/or quantitative analysis of the immune response which has been generated to a parasite, in particular *Plasmodium*, to parasite pathology, such as malarial pathology. Still further, the analysis of the immune response in this unique and surprisingly effective antigen-based manner provides a means of facilitating epitope specific screening or the rational design of functionally effective immunogenic molecules. This aspect of the present invention has been particularly facilitated by the successful generation of synthetic GPI molecules.

SUMMARY OF THE INVENTION

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

One aspect of the present invention is directed to a method of eliciting or inducing, in a mammal, an immune response directed to a microorganism said method comprising administering to said mammal an effective amount of an immunogenic composition which composition comprises a molecule capable of inducing an immune response directed to the inositolglycan domain of a GPI but which molecule is substantially incapable of inducing an immune response directed to a lipidic domain of said GPI.

Another aspect of the present invention provides a method of eliciting or inducing, in a mammal, an immune response directed to a microorganism said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain.

Still another aspect of the present invention is directed to a method of eliciting or inducing, in a mammal, an immune response directed to a parasite said method comprising administering to said mammal an effective amount of an immunogenic composition which composition comprises the inositolglycan domain portion of a parasite GPI or derivative or equivalent thereof and which inositolglycan domain portion comprises insufficient lipidic domain of said parasite GPI to induce or elicit an immune response directed to said lipidic domain.

Still yet another aspect of the present invention contemplates a method of eliciting or inducing, in a mammal, an immune response directed to $P.\ falciparum$ said method comprising administering to said mammal an effective amount of an immunogenic composition which composition comprises a GPI inositolglycan domain wherein said GPI inositolglycan domain comprises the structure
ethanolamine-phosphate-(Man$\alpha$1,2)-Man$\alpha$1,2Man$\alpha$1, 6Man$\alpha$1,4GlcN-myo-inositol phosphoglycerol
or derivative or equivalent thereof.

Still yet another aspect of the present invention contemplates a method of eliciting or inducing, in a mammal, an immune response directed to $P.\ falciparum$ said method comprising administering to said mammal an effective amount of an immunogenic composition which composition comprises a GPI inositolglycan domain wherein said GPI inositolglycan domain comprises the structure
$X_1$—$X_2$—$X_3$—$X_4$-ethanolamine-phosphate-Man$\alpha$1,2)-Man$\alpha$1,2Man$\alpha$1,6Man$\alpha$1,4GlcN-myo-inositol phosphoglycerol
wherein $X_1$, $X_2$, $X_3$ and $X_4$ are any 4 amino acids, or derivative or equivalent of said GPI inositolglycan domain.

Still yet another aspect of the present invention contemplates a method of eliciting or inducing, in a mammal, an immune response directed to $P.\ falciparum$ said method comprising administering to said mammal an effective amount of an immunogenic composition which composition comprises a GPI inositolglycan domain wherein said GPI inositolglycan domain comprises the structure
EtN-P-[M$\alpha$2]M$\alpha$2 M$\alpha$6 M$\alpha$4G$\alpha$6Ino
EtN-P-[M$\alpha$2][G]M$\alpha$2 M$\alpha$6 M$\alpha$4G$\alpha$6Ino
EtN-P-[M$\alpha$2][X]M$\alpha$2 M$\alpha$6 M$\alpha$4G$\alpha$6Ino
EtN-P-[M$\alpha$2][EtN-P]M$\alpha$2 M$\alpha$6 M$\alpha$4G$\alpha$6Ino
EtN-P-M$\alpha$2 M$\alpha$6 M$\alpha$4G
EtN-P-M$\alpha$2 M$\alpha$6 M
EtN-P-[M$\alpha$2][G]M$\alpha$2 M$\alpha$6 M$\alpha$4G
EtN-P-[M$\alpha$2][X]M$\alpha$2 M$\alpha$6 M$\alpha$4G
EtN-P-[M$\alpha$2][EtN-P]M$\alpha$2 M$\alpha$6 M$\alpha$4G
M$\alpha$2 [M$\alpha$2][G]M$\alpha$2 M$\alpha$6 M$\alpha$4G
M$\alpha$2 [M$\alpha$2][X]M$\alpha$2 M$\alpha$6 M$\alpha$4G
M$\alpha$2 [M$\alpha$2][EtN-P]M$\alpha$6 M$\alpha$4G
M$\alpha$6 M$\alpha$4G$\alpha$6Ino
M$\alpha$2 M$\alpha$6 M$\alpha$4G$\alpha$6Ino
M$\alpha$2 [M$\alpha$2]M$\alpha$6 M$\alpha$4G$\alpha$6Ino
M$\alpha$2 [M$\alpha$2][G]M$\alpha$6 M$\alpha$4G$\alpha$6Ino
M$\alpha$2 [M$\alpha$2][X]M$\alpha$2 M$\alpha$4G$\alpha$6Ino
EtN-P-[M$\alpha$2][G]M$\alpha$2 M$\alpha$6 M
EtN-P-[M$\alpha$2][X]M$\alpha$2 M$\alpha$6 M
EtN-P-[M$\alpha$2][EtN-P]M$\alpha$2 M$\alpha$6 M
M$\alpha$2 [M$\alpha$2][G]M$\alpha$2 M$\alpha$6 M
M$\alpha$2 [M$\alpha$2][X]M$\alpha$2 M$\alpha$6 M
M$\alpha$2 [M$\alpha$2][EtN-P]M$\alpha$6 M
M$\alpha$2 M$\alpha$6M
M$\alpha$6 M$\alpha$4G
EtN-P-[M$\alpha$2][G]M$\alpha$2 M
EtN-P-[M$\alpha$2][X]M$\alpha$2 M
EtN-P-[M$\alpha$2][EtN-P]M$\alpha$2 M
EtN-P-(Man$\alpha$1,2)-6M$\alpha$1, 2M$\alpha$1, 6Man$\alpha$1, 4GlcNH$_2\alpha$1-myo-inositol-1,2 cyclic-phosphate NH$_2$—CH$_2$—CH$_2$—PO$_4$-(Man$\alpha$1-2) 6Man$\alpha$1-2, Man$\alpha$1-6, Man$\alpha$1-4 GlcNH$_2$-6myo-inositol-1,2 cyclic-phosphate
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, $\alpha$ represents $\alpha$-linkages which may be substituted with $\beta$-linkages wherever required, and numeric values represent positional linkages which may be substituted with any other positional linkages as required.

A further aspect of the present invention contemplates a method of therapeutically or prophylactically treating a mammal for a microorganism infection said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with infection of said mammal by said microorganism.

Another further aspect of the present invention is directed to a method of therapeutically or prophylactically treating a mammal for a microorganism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with infection of said mammal by said microorganism.

In a related aspect, the present invention provides a method for the treatment and/or prophylaxis of a mammalian disease condition characterised by a microorganism infection, said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with said microorganism infection.

Still another further aspect of the present invention is directed to a method for the treatment and/or prophylaxis of a mammalian disease condition characterised by a microorganism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with said microorganism infection.

Still yet another aspect of the present invention relates to the use of a composition comprising a molecule capable of inducing an immune response directed to a microorganism GPI inositolglycan domain but substantially incapable of inducing an immune response directed to a lipidic domain of GPI in the manufacture of a medicament for the therapeutic and/or prophylactic treatment of a mammalian disease condition characterised by infection with said microorganism.

Still yet another hither aspect of the present invention relates to the use of an immunogenic composition comprising a *Plasmodium* GPI inositolglycan domain or derivative or equivalent thereof which inositolglycan domain comprises insufficient lipidic domain of a *Plasmodium* GPI to elicit or induce an immune response directed to a GPI lipidic domain in the manufacture of a medicament for the therapeutic and/or prophylactic treatment of a mammalian disease condition characterized by infection with said *Plasmodium*.

Another aspect of the present invention is directed to a composition capable of inducing an immune response directed to a microorganism, said composition comprising a molecule capable of inducing an immune response against a microorganism GPI inositolglycan domain but substantially incapable of inducing an immune response to a lipidic domain of a GPI.

Still another aspect of the present invention is directed to a composition capable of inducing an immune response directed to a microorganism said composition comprising a modified GPI molecule or derivative or equivalent thereof which modified GPI molecule comprises insufficient lipidic domain to induce or elicit an immune response directed to a GPI lipidic domain.

Another aspect of the present invention relates to a method of inhibiting, halting or delaying the onset of progression of a mammalian disease condition characterized by a microorganism infection said method comprising administering to said mammal an effective amount of an antibody has hereinbefore described.

Still yet another aspect of the present invention relates to a vaccine composition comprising as the active component a modified GPI molecule or derivative or equivalent thereof which modified GPI molecule or derivative or equivalent thereof which modified GPI molecule comprises insufficient lipidic domain to induce or elicit an immune response directed to a GPI lipidic domain.

Still another aspect of the present invention is directed to a pharmaceutical composition comprising a molecule capable of inducing an immune response directed to a microorganism GPI inositolglycan domain but substantially incapable of inducing an immune response directed to a lipidic domain of a GPI, as broadly described above, together with one or more pharmaceutically acceptable carriers and/or diluents.

A further aspect of the present invention is directed to antibodies to GPI inositolglycan domains but substantially incapable of interacting with the lipidic domain of a GPI.

Yet another aspect of the present invention relates to a pharmaceutical composition comprising an antibody directed to a GPI inositolglycan domain together with one or more pharmaceutically acceptable carriers or diluents as hereinbefore described.

A further aspect of the present invention relates to the use of the antibodies of the present invention in relation to disease conditions. For example, the present invention is particularly useful but in no way limited to use in treating parasitic infections, their symptoms and pathologies.

Another aspect of the present invention relates to a method of inhibiting, halting or delaying the onset of progression of a mammalian disease condition characterised by a microorganism infection said method comprising administering to said mammal an effective amount of an antibody has hereinbefore described.

Accordingly, another aspect of the present invention provides a method for detecting, in a biological sample, an immunointeractive molecule directed to a microorganism said method comprising contacting said biological sample with a molecule comprising said microorganism GPI inositolglycan domain or a derivative or equivalent thereof and qualitatively and/or quantitatively screening for said GPI inositolglycan domain-immunointeractive molecule complex formation.

In a related aspect, the present invention provides a method for detecting, monitoring or otherwise assessing an immune response directed to a microorganism in a subject said method comprising contacting a biological sample, from said subject, with a molecule comprising said microorganism GPI inositolglycan domain or a derivative or equivalent thereof and qualitatively and/or quantitatively screening for GPI inositolglycan domain-immunointeractive molecule complex formation.

In one aspect, the present invention therefore more preferably provides a method for detecting, in a biological sample, an immunointeractive molecule directed to *Plasmodium* said method comprising contacting said biological sample with the inositolglycan domain portion of a *Plasmodium* GPI or derivative or equivalent thereof and qualitatively and/or quantitatively screening for GPI inositolglycan domain-immunointeractive molecule complex formation.

In a related aspect, the present invention more preferably provides a method for detecting, monitoring or otherwise assessing an immune response directed to *Plasmodium* in a subject said method comprising contacting a biological sample, from said subject, with the inositolglycan domain portion of a *Plasmodium* GPI or derivative or equivalent thereof and qualitatively and/or quantitatively screening for GPI inositolglycan domain-immunointeractive molecule complex formation.

One aspect of the present invention therefore most preferably provides a method for detecting, in a biological sample, an antibody directed to *Plasmodium* said method comprising contacting said biological sample with the inositolglycan domain portion of a *Plasmodium* GPI or a derivative or equivalent thereof and qualitatively and/or quantitatively screening for GPI inositolglycan domain-antibody complex formation.

A related aspect of the present invention most preferably provides a method for detecting, monitoring, or otherwise assessing an immune response directed to *Plasmodium* in a subject said method comprising contacting a biological sample, from said subject, with the inositolglycan domain portion of a *Plasmodium* GPI or a derivative or equivalent thereof and qualitatively and/or quantitatively screening for GPI inositolglycan domain-antibody complex formation.

Accordingly, another aspect of the present invention is directed to a modular kit comprising one or more members wherein at least one member is a solid support comprising a GPI molecule as hereinbefore defined.

Accordingly, the present invention should also be understood to extend to a method for analyzing, designing and/or modifying an agent capable of interacting with an anti-GPI glycan immunointeractive molecule binding site, which immunointeractive molecule is identifiable utilizing the diagnostic methodology hereinbefore disclosed, said method comprising contacting said immunointeractive molecule or derivative thereof with a putative agent and assessing the degree of interactive complementarity of said agent with said binding site.

The present invention also extends to the use of the molecules generated in accordance with this aspect of the present invention in accordance with the therapeutic, prophylactic and diagnostic methods hereinbefore described.

c. Haemotoxylin-Eosin stained sections of brain tissue showing blood vessels from KLH-glycan immunized (left and center panels) and sham-immunized (right panel) mice sacrificed on day 6 post-infection. d. As an index of pulmonary oedema, the ratio of we weight to dry weight of lungs from KLH-glycan-immunized and sham-immunized animals at day 6 post-infection are expressed as a proportion of the lung wet:dry weight ratio of age/sex matched uninfected controls. e. pH of serum drawn at day 6 from uninfected and *P. berghei*-ANKA-infected immunized and sham-immunized donors. *, p>0.05.

Figure 16:
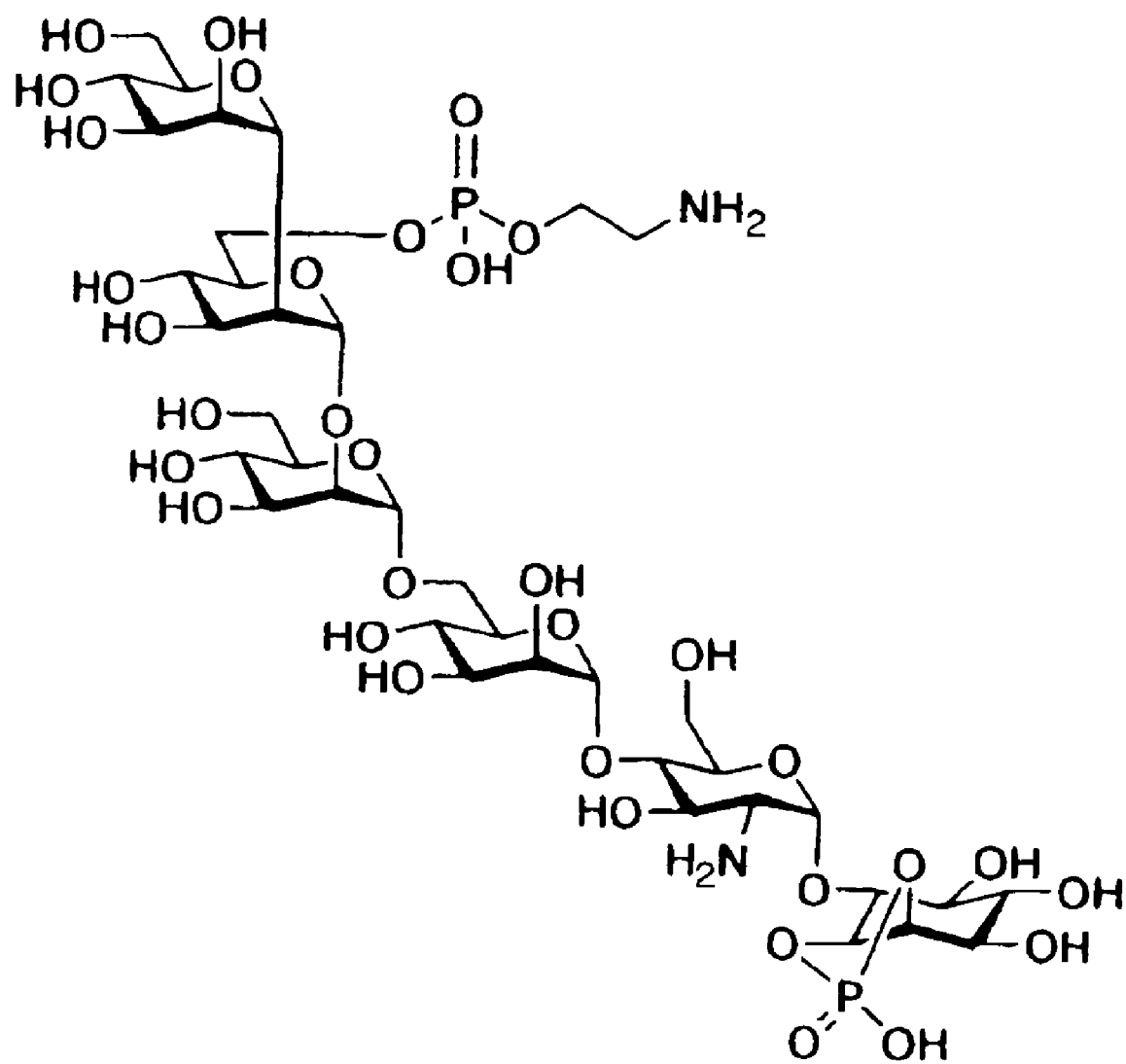

FIG. 16 is a schematic representation of the synthetic glycan core unit.

Figure 17:
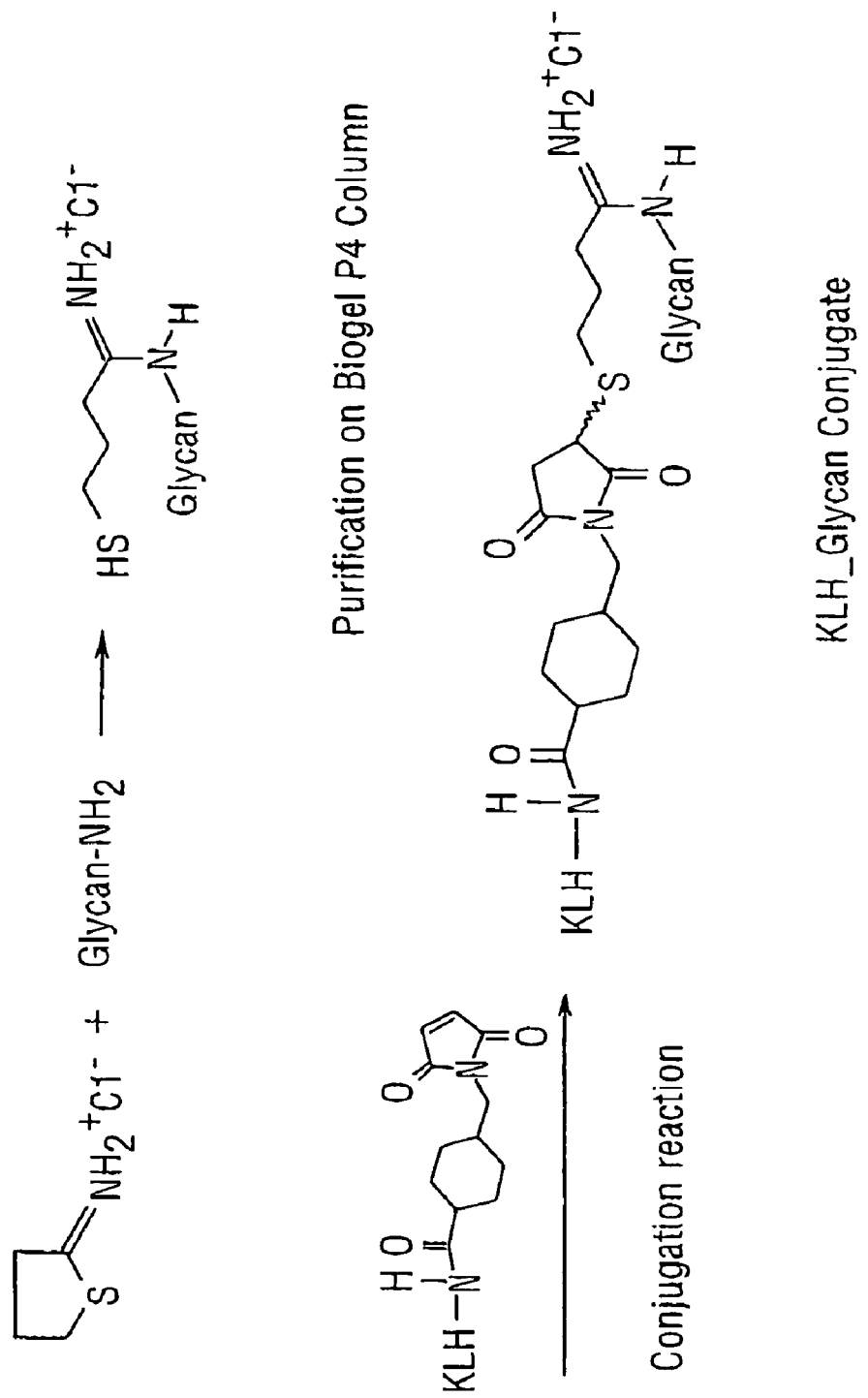

FIG. 17 is a schematic representation of the method used to conjugate the glycan to a carrier protein. Sham conjugation procedures were also followed substituting cysteine for glycan.

FIG. 18 is a representation of the conjugation ratios obtained with the various carrier proteins Ovalbumin (OVA), KeyHole Limpet Haemocyanin (KLH) and Bovine Serum Albumin (BSA). Conjugation efficiency was determined by GC/MS analysis of myo-inositol content of protein-glycan conjugate.

Figure 19:
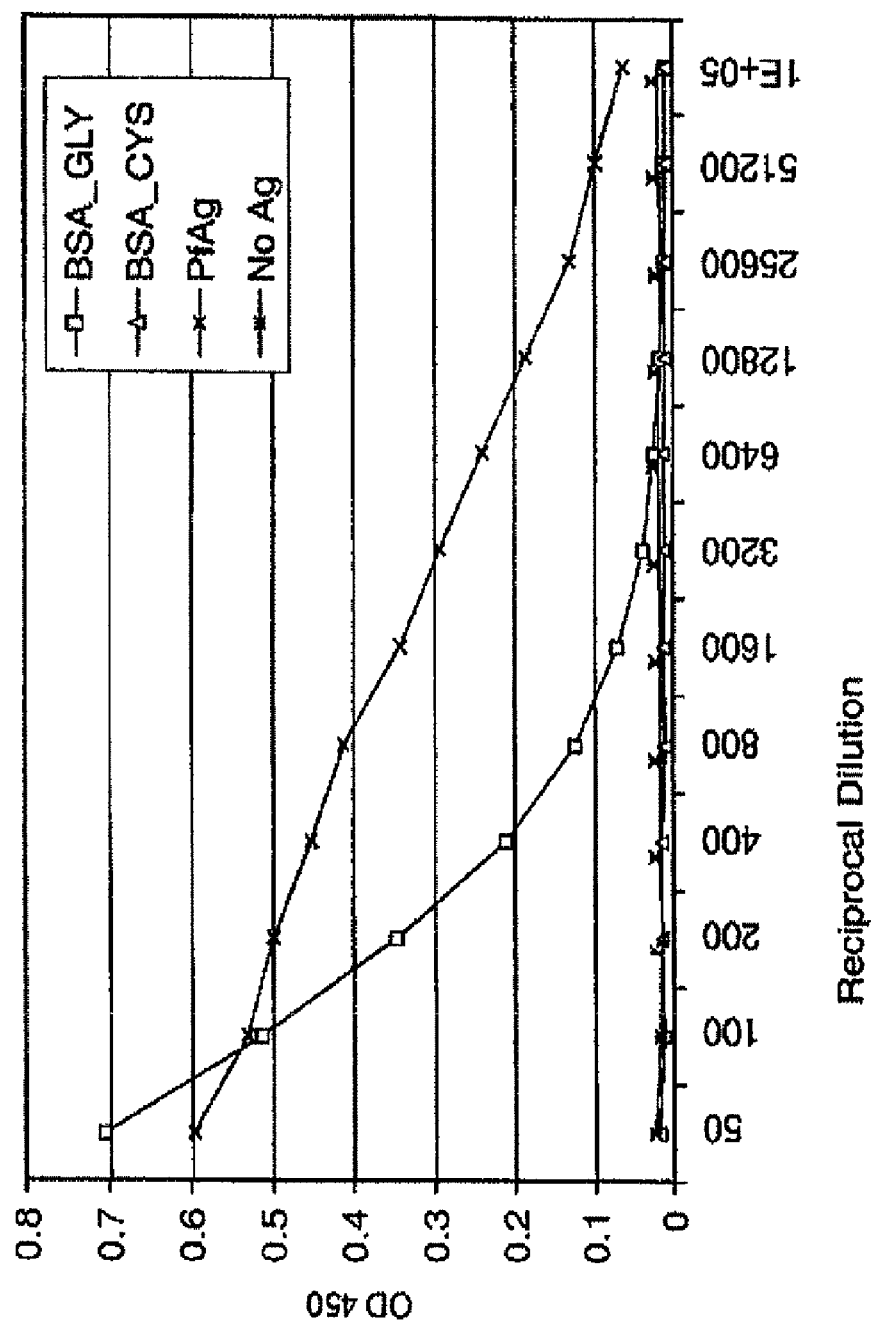

FIG. 19 is a graphical representation of the IgG response to synthetic glycan PNG sera 93. Specifically, this figure shows an ELISA test using human serum from a Papua New Guinean donor naturally exposed to malaria infection, reacted against a range of antigens including No Ag (No antigen at all), BSA-Cys (Sham conjugated BSA-Cysteine), BSA-GLY (BSA conjugated to synthetic GPI glycan) and PfAg (total *P. falciparum* malaria antigen. The data show that the synthetic GPI glycan is able specifically to detect anti-Glycan antibodies in human serum from an individual exposed to malaria.

Figure 20:
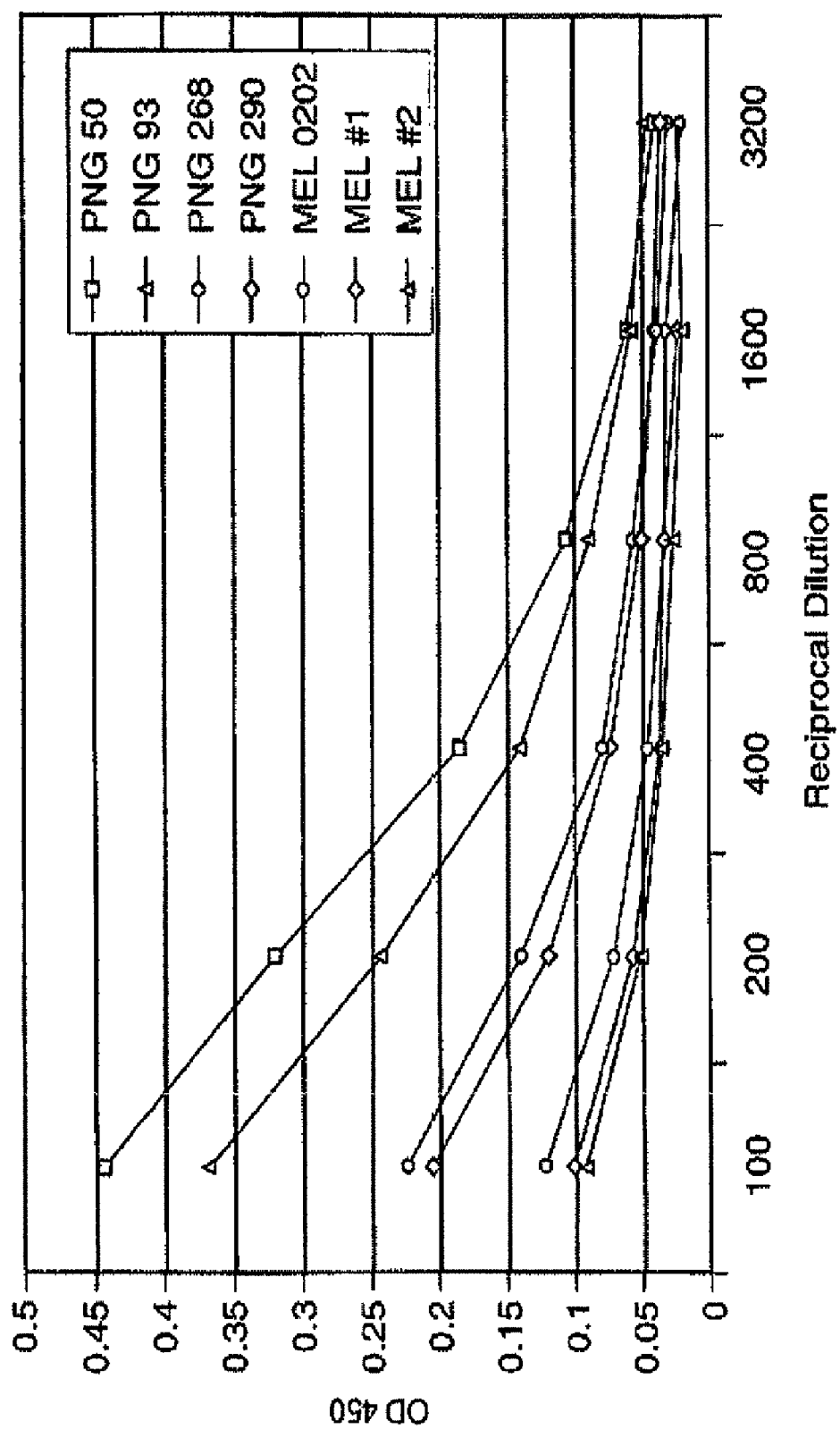

FIG. 20 is a graphical representation of the IgG response to synthetic glycan PNG and Melbourne individuals. Specifically, this figure shows that individuals from a malaria endemic part of Papua New Guinea have considerably higher titres than non-malaria exposed Melbourne donors when the synthetic glycan is used as a capture antigen.

Figure 21:
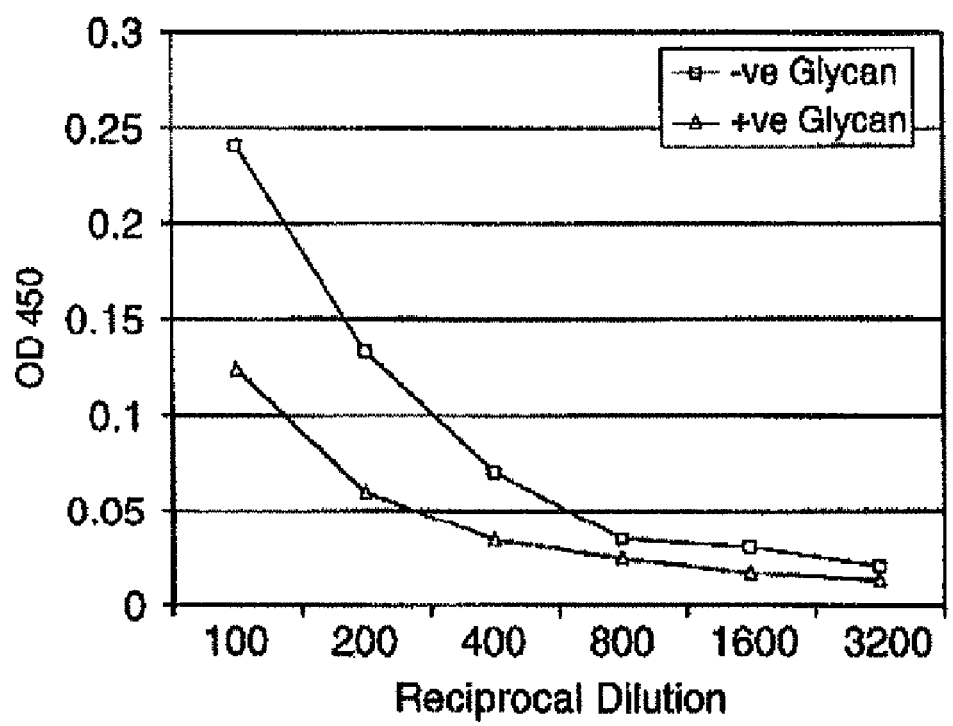

FIG. 21 is both a graphical and tabulated representation of competition ELISAS performed on synthetic glycan vs GPI. Specifically, this figure shows that synthetic GPI glycan is able to compete out the majority of human antibody responses to the native GPI toxin when used in molar excess as a competitor. This defines the fact that the synthetic material is an authentic antigenic match for the native material and also shows that the majority of anti-toxin serological reactivity is encompassed within the glycan region. These findings are at odds with others who claim that the majority of human anti-GPI serological reactivity is directed towards the lipidic domain (for example Naik, R. S. et al. (2000) Glycosylphosphatidylinositol anchors of *Plasmodium falciparum*: molecular characterization and naturally elicited antibody response that may provide immunity to malaria pathogenesis. *J. Exp. Med.* 192, 1563-1576).

DETAILED DESCRIPTION OF THE INVENTION

The present invention is predicated, in part, on the surprising determination that a *Plasmodium* GPI molecule which excludes the lipidic portion will induce protective immunity whereas a GPI molecule which comprises the lipidic domain will not. This determination has facilitated the development of compositions and methodology for application, inter alia, in the prophylactic or therapeutic treatment of microorganism infection.

It has still further been surprisingly determined that the subject GPI molecule, in particular the synthetic GPI molecule herein disclosed, facilitates a highly effective and informative antigen-based analysis of one or more qualitative and/or quantitative aspects of the immune response to a parasite, per se, or parasite pathology. The enablement of these analyses further facilitate, inter alia, the identification and/or isolation of unique specificities of antibodies, epitope specific screening or the rational design of immunogenic molecules and the generation of functionally effective immunointeractive molecules.

Accordingly, one aspect of the present invention is directed to a method of eliciting or inducing, in a mammal, an immune response directed to a microorganism said method comprising administering to said mammal an effective amount of an immunogenic composition which composition comprises a molecule capable of inducing an immune response directed to the inositolglycan domain of a GPI but which molecule is substantially incapable of inducing an immune response directed to a lipidic domain of said GPI.

The present invention is predicated on the surprising observation that mice immunized with purified, intact, free GPI mount an IgM dominated response directed predominantly to the lipidic domain of the molecule, which cross reacts with host GPI lipidic domains which are exposed at host cell surfaces. The antibodies are not protective clinically against subsequent parasite infection. In fact, passive transfer of these antibodies exacerbates disease severity. However, immunization with the glycan domain of malarial GPI results in IgG antibodies interactive with the glycan domain of GPI and mice thus immunized are substantially protected against pathology induced by subsequent malaria challenge. Passive transfer of these IgG antibodies is protective against pathology. The inventors have demonstrated, therefore, that IgM antibodies to the lipidic domain and IgG antibodies to the glycan domain of the malaria GPI differ in their effects, the former promoting disease and the latter preventing it. It should be understood that in preventing or minimizing the induction of an immune response directed to the GPI of a microorganism, the onset of an immune response directed to lipidic domain of the subject mammal (host) is thereby prevented or minimized by virtue of minimizing the production of antibodies to a microorganism GPI which would otherwise cross-react with the host GPI.

GPIs are ubiquitous among eukaryotes; described from *T. brucei, T. cruzi, Plasmodium, Leishmania,* and *Toxoplasma,* as well as yeast, insect, fish and numerous mammalian sources (for recent reviews see McConville, M. J. and Ferguson, M. A., (1993) *Biochem. J.* 294:305 and Stevens, V. L. (1995) *Biochem. J.* 310:361). GPIs consist of a conserved core glycan (Man$\alpha$1-2Man$\alpha$1-6Man$\alpha$1-4GlcNH$_2$) linked to the 6-position of the myo-inositol ring of phosphatidylinositol (PI). GPIs are built up on the cytoplasmic face of the endoplasmic reticulum (ER) by the sequential addition of sugar residues to PI by the action of glycosyltransferases. The maturing GPI is then translocated across the membrane to the luminal side of the ER, whence it may be exported to the cell surface, free or in covalent association with proteins. The tetrasaccharide core glycan may be further substituted with sugars, phosphates and ethanolamine groups in a species and tissue-specific manner. GPI fatty acid moieties can be either diacylglycerols, alkylacylglycerols, monoalkylglycerols or ceramides, with additional palmitoylations or myristoylations to the inositol ring. The overall picture is of a closely related family of glycolipids sharing certain core features but with a high level of variation in fatty acid composition and side-chain modifications to the conserved core glycan.

Accordingly, reference herein to "GPI inositolglycan domains" should be read as including reference to all forms of GPI inositolglycan domains and derivatives or equivalents thereof. The term "GPI inositolglycan" is used interchangeably with terms such as but not limited to "inositolglycan" (IG), "inositophosphoglycan" (IPG), "phosphoinositolglycan" (PIG), "phosphooligosaccharide" (POS) and the molecules described by these terms should be understood as "GPI inositolglycan" molecules. It should also be understood that reference to "GPI inositolglycan domain" includes reference to a GPI inositolglycan domain linked, bound or otherwise associated with non-inositolglycan molecules such as, but not limited to, the glycerol linker sequence which links the lipidic domain to the inositolglycan domain, a non-immunogenic portion of the lipidic domain or an amino acid peptide.

Preferably the molecule is a portion of GPI which comprises the inositolglycan domain or derivative or equivalent thereof but substantially does not contain a portion capable of inducing an immune response directed to a lipidic domain of said GPI.

Accordingly, the present invention more particularly provides a method of eliciting or inducing, in a mammal, an immune response directed to a microorganism said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain.

Preferably, said modified GPI molecule is the inositolglycan domain portion of GPI or derivative or equivalent thereof.

Still without limiting the present invention in any way, the administration of an immunogenic composition comprising an inositolglycan domain portion of GPI or derivative or equivalent thereof substantially lacking the lipidic domain, as hereinbefore defined, is also thought to benefit the subject mammal by minimizing certain unwanted responses which may otherwise occur incidentally to immune response induction, but which enhance disease severity, if the subject immunogenic molecule comprised a lipid domain. Specifically;
(i) the intact GPI is a toxin and may induce non-immunological physiological sensitization in recipients such that the response to the natural GPI toxin is exacerbated upon malaria challenge. The inventors have shown that the lipidic portion of the intact GPI is necessary for full toxic activity by virtue of its' ability to initiate lipid-dependent signaling in host cells, and act as a lipidic second messenger;
(ii) intact glycolipids may associate with host CD1 molecules for presentation to CD1-restricted NKT cells or other unusual T cell lineages. These T cells are known to produce high levels of cytokines such as interferon-γ and IL-4 very rapidly in response to stimulation and are likely to be crucial regulators of downstream TH1/TH2 differentiation. Immunization with purified, intact (i.e. lipidated), free GPI may result in priming of these T cells which subsequently respond with high levels of interferon-γ upon parasite challenge, thereby exacerbating the disease syndromes. That is, immunological sensitization of unusual T cells may contribute to the phenomenon of exacerbated disease severity.

"Derivatives" and "equivalents" should be understood to include fragments, parts, portions, chemical equivalents, mutants, homologs and analogs. Chemical equivalents of a GPI inositolglycan domain can act as a functional analog of the GPI inositolglycan domain. For example, a chemical equivalent of the GPI inositolglycan domain includes a GPI inositolglycan domain in which the phosphoglycerol component of the inositolglycan has been modified to increase hydrophobicity. This may be achieved by replacement with truncated, partial or modified fatty acids or other hydrophobic moieties and acts to improve the immunogenicity or stability of the molecule, without generating an undesirable antibody response. In another example, a chemical equivalent includes GPI glycan in which the terminal inositol-phosphoglycerol is replaced with inositol-1,2 cyclic-phosphate. Without limiting the present invention in any way, such a change will not substantially alter the functional properties of the derivatised GPI glycan relative to non-derivatised molecules. Rather, such a substitution is the inherent outcome of certain chemical synthesis procedures. Chemical equivalents may not necessarily be derived from a GPI inositolglycan domain but may share certain confirmational similarities. Alternatively, chemical equivalents may be specifically designed to mimic certain immunological and physiochemical properties of the GPI inositolglycan domain. Chemical equivalents may be chemically synthesized or may be detected following, for example, natural product screening. Chemical equivalents also include synthetic carbohydrates and peptide mimics. Homologs of GPI inositolglycan domains contemplated herein include, but are not limited to, GPI inositolglycan domains from different species including, for example, *Saccharomyces*. Fragments, include portions such as the glycan component of the inositolglycan domain, which portions are effective in achieving the object of the present invention.

GPI inositolglycan domains suitable for use in the present invention may be derived from any natural, recombinant or synthetic source. This includes, for example, GPI inositolglycan domains derived by genetic manipulation of expression systems, and by manipulations of the GPI post-translational modifications of proteins via recombinant DNA techniques such as glycosylation inhibitors. It also includes chemically synthetic or semi-synthetic inositolglycan domains and fragments thereof derived by any chemical process including the use of enzymes for the addition or removal of residues.

The term "microorganism" should be understood in its broadest sense and includes, for example, the parasitic and fungal taxa *Plasmodium, Trypanosoma, Leishmania, Toxoplasma* and *Candida*. "Microorganism" should also be understood to extend to molecules which are secreted by or shed from the subject organism. This would include for example, toxin molecules or molecules which are cleared from the surface of the microorganism. Preferably, the GPI inositolglycan domain suitable for use in the present invention is a parasite GPI inositolglycan domain and even more preferably a *Plasmodium* GPI inositolglycan domain.

Accordingly, the present invention is preferably directed to a method of eliciting or inducing, in a mammal, an immune response directed to a parasite said method comprising administering to said mammal an effective amount of an immunogenic composition which composition comprises the inositolglycan domain portion of a parasite GPI or derivative or equivalent thereof and which inositolglycan domain portion comprises insufficient lipidic domain of said parasite GPI to induce or elicit an immune response directed to said lipidic domain.

Even more preferably said parasite GPI inositolglycan domain is a *Plasmodium* GPI inositolglycan domain or derivative or equivalent thereof.

Most preferably, said *Plasmodium* is *P. falciparum*.

Yet even more preferably, the present invention contemplates a method of eliciting or inducing, in a mammal, an immune response directed to *P. falciparum* said method comprising administering to said mammal an effective amount of an immunogenic composition which composition comprises a GPI inositolglycan domain wherein said GPI inositolglycan domain comprises the structure
ethanolamine-phosphate-(Manα1,2)-Manα1,2Manα1,6Manα1,4GlcN-myo-inositol phosphoglycerol
or derivative or equivalent thereof.

In another most preferred embodiment the immunogenic composition comprises a GPI inositolglycan domain wherein said GPI inositolglycan domain comprises the structure
$X_1$—$X_2$—$X_3$—$X_4$-ethanolamine-phosphate-(Manα1,2)-Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another preferred embodiment the immunogenic composition comprises a GPI inositolglycan domain wherein said GPI inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
EtN-P-[42][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

Any of these structures may be further modified by substituents of positive, negative or neutral charge such as phosphates, phosphoglycerol, hexosamines, amino acids, thiols etc in any position and with any type of linkage. These structures may be further modified by addition of any number of amino acids for the purpose of providing a linkage sequence.

Reference to "derivative" herein should be understood to encompass, in one preferred embodiment, an immunogenic composition comprising a GPI inositolglycan domain derivative wherein the terminal inositol-phosphoglycerol is substituted with inositol-1,2 cyclic-phosphate. Without limiting the present invention in any way, such a substitution is a characteristic outcome where certain forms of chemical synthesis are utilized, such as that exemplified in Example 18.

Accordingly, in yet still another preferred embodiment, the immunogenic composition comprises a GPI inositolglycan domain wherein said GPI inositolglycan domain comprises the structure
EtN-P-(Manα1,2)-6Mα1, 2Mα1, 6Manα1, 4GlcNH$_2$α1-myo-inositol-1,2 cyclic-phosphate
or derivative or equivalent thereof wherein EtN is ethanolamine, P is phosphate and M is mannose.

Even more preferably, the immunogenic composition comprises a GPI inositolglycan domain wherein said GPI inositolglycan domain comprises the structure
$NH_2$—$CH_2$—$CH_2$—$PO_4$-(Manα1-2) 6Manα1-2 Manα1-6Manα1-4GlcNH$_2$-6myo-inositol-1,2 cyclic-phosphate
or derivative or equivalent thereof.

It should be understood that non-N-acetylated hexosamine includes glucosamine or any other nitrous-acid labile substituent. It should be further understood that any of these structures may be further modified by substituents including, but not limited to, of positive, negative or neutral charge such as phosphates, phosphoglycerol, hexosamines, amino acids or thiols in any position and with any type of linkage.

The GPI inositolglycan domain of the present invention may be conjugated to another molecule. Said conjugation may be performed for any one or more reasons such as, but not limited to:

(i) The GPI inositolglycan domain may be too small to be antigenic. Accordingly, conjugation to a carrier molecule, such as a protein, may be required such that said GPI inositolglycan domain, which forms part of the GPI inositolglycan domain-conjugate, acts as a hapten and immunity is induced to said GPI inositolglycan domain. The carrier protein may be selected from a range of antigenic proteins such as but not limited to recombinant proteins derived from *Plasmodium* gene sequences, tetanus toxoid, purified protein derivative, hepatitis B or Key Hole Limpet Haemocyanin and Diptheria toxoid.

(ii) The GPI inositolglycan domain when conjugated with specific anti-pathogen vaccine molecules (such as anti-malarial vaccine molecules) may result in the production of anti-inositolglycan domain antibodies which reverse the immune suppression that otherwise may occur in response to exposure to the native form of the vaccine molecule where said molecule is itself GPI-anchored. For example, the GPI inositolglycan domain may be coupled to a malarial recombinant protein which can act as both a carrier protein and a vaccine in its own right.

Without intending to limit this aspect of the present invention to any one theory or mode of action, primary and secondary T lymphocyte responses to some GPI-anchored surface protein antigens are inhibited by the GPI anchor. Examples of such protein antigens includes Circumsporozoite (CS) proteins of *P. falciparum* and *P. berghei* and the membrane-form of Variant Surface Glycoprotein of *F. brucei*. Since immunization against synthetic or recombinant peptides or proteins of GPI-anchored surface molecules such as the CS protein, MSP-1, MSP-2 or MSP-4, for example, may be insufficient to allow MHC Class II anamnestic boosting when the native antigens are encountered during natural parasitic challenge due to the induction of immunosuppression, immunization against the GPI moiety provides a means to alleviate this immunosuppression.

(iii) The GPI inositolglycan domain may comprise only part of the target epitope. For example, peptide sequences, other carbohydrates (and any associated post-translational modifications) corresponding to C-terminal domains of native GPI-anchored proteins or GPI-anchored glycoconjugates may also form part of the target GPI inositolglycan domain epitope. Removal of any part of the epitope (by removing the portion of the C-terminal domain which forms part of the GPI inositolglycan domain epitope) may lead to reduction or loss of binding of antibodies. Said peptide sequences or carbohydrates would therefore be conjugated to said GPI inositolglycan domain. For example, some antibodies to malarial GPI, while specifically neutralizing GPI function, recognise epitopes which predominantly include the inositolglycan but also include portions of the protein to which the GPIs are actually bound in nature, i.e. the adjacent C-terminal portions of GPI-anchored proteins. The presence of peptide domains can also improve the affinity of certain antibodies, for example by helping to stabilise the inositolglycan conformationally. Furthermore, such conjugation can render a relatively unimmunogenic inositolglycan domain sufficiently immunogenic. Specifically, the inclusion of a C-terminal peptide determinant, for example, may help increase the immunogenicity of the inositolglycan by forming a composite antigen which is more immunologically foreign than inositolglycan alone.

The resulting GPI inositolglycan domain-conjugate may be administered as a preparation formulated in or with an adjuvant. The adjuvant is selected from the range of adjuvants known to induce high levels of antibody, including water in oil emulsions, oil in water emulsions, water in oil in water double emulsions, saponin, Quil A extracts and other derivatives of saponin, DEAE-dextran, dextran sulphate, aluminium salts and nonionic block co-polymers. The adjuvant may include other immunomodulators, such as muramyl-dipeptide and derivatives, cytokines, and cell wall components from species of mycobacteria or corynebacteria. The adjuvant formulation may include a combination of two or more of the adjuvants listed. These lists are not to be taken as exhaustive. The selection of adjuvant is in part dependent on the species being targeted and is based on the level and duration of the immune response required and on the lack of reactogenicity (ie tissue compatibility). The level of active component and adjuvant are chosen to achieve the desired level and duration of immune response.

Host GPIs play a significant role in the normal physiological regulation of various cellular responses in higher eukaryotes. Foreign GPIs such as GPIs of parasite origin exert pathophysiological effects, and specifically regulate host cell function, by acting as a mimic of endogenous host GPI signalling pathways. Signal transduction induced in host cells by GPI's of *P. falciparum, T. brucei,* and *L. mexicana,* for example, activate the macrophage lineage-specific hck member of the src-family of protein tyrosine kinases within 30 seconds of addition to cells (Tachado et al (1997), supra). Protein tyrosine kinase (PTK) activation is required for downstream gene expression resulting in phosphorylation, cell signalling and TNF, IL-1, iNOS, ICAM-1 and VCAM expression (Schofield, L., Novakovic, S., Gerold, P., Schwarz, R. T., McConville, M. J. and Tachado S. D. (1996) *J. Immunol.* 156:1886-1896, Tachado, S. D., Gerold, P., McConville, M. J., Baldwin, T., Quilici, D., Schwarz, R. T., and Schofield, L. (1996) *Journal of Immunology* 156:1897-1907 and Tachado et al (1997), supra). PTK activation maps to the inositolglycan moiety of GPI and follows binding of the core glycan to a receptor on the surface of cells (Tachado et al (1997), supra). Parasite GPIs appear to activate similar kinases as those activated upon perturbation of endogenous GPI-anchored proteins at the cell surface.

The toxic nature of foreign GPIs such as parasite GPIs can be exemplified with respect to malarial GPIs. When inoculated in vivo, the malarial GPI induces pyrexia and symptoms of acute malaria and causes the death of the recipient in a standard assay of TNF driven lethality (Schofield and Hackett (1993), supra). In addition to inducing TNF and IL-1 expression in macrophages, the GPI exerts several other TNF independent effects on host tissues that may contribute to pathological processes in malaria infections. GPI directly increases expression of E-selectin, ICAM and VCAM in vascular endothelial cells (Schofield et al (1996), supra). GPI also induces de novo protein synthesis of inducable nitric oxide synthase and the production of NO in a time and dose dependent manner, from macrophages and synergises with interferon-γ in this activity (Tachado et al (1996) supra). In the hypoxic or ischaemic model, cerebral malaria is proposed to result from a blockage of the post capillary venules of the brain by sequestered parasite infected erythrocytes binding to the adhesion molecules ICAM, VCAM and E-selectin (Berendt. A. R., Turner, G. D. H. and Newbold, C. I. (1994) *Parasitol Today* 10:412, 1994). GPI can therefore be lethal in vivo and induce malarial symptomology encompassing both systemic inflammation and organ-specific pathology such as the cerebral syndrome.

Foreign GPIs may also induce immunosuppression. GPIs isolated from *P. falciparum* and *T. brucei*, for example, when added at low concentrations to cultures of CD4+ and CD8+ α/β TCR+ T cells block cell cycle progression and cellular proliferation, inhibiting the upregulation of IL-2 R/CD25 and CD28 expression and blocking expression of IL-2, interferon γ, and IL-4. The GPIs also inhibit the T cell proliferative response to IL-2. In vivo, GPI anchored surface proteins such as malaria CS protein, MSP-1, MSP-2, and the membrane form variant surface glycoprotein of *T. brucei* inhibit, via the covalently associated GPI anchor, primary and secondary T lymphocyte responses to said antigens.

While not intending to limit the present invention to any one theory or mode of action, immunisation with a GPI molecule lacking the lipid domain induces an IgG response to the inositolglycan domain which blocks subsequent parasitic GPI action. Both toxicity and immunosuppression, as described above, are significantly reduced.

A further aspect of the present invention relates to the use of the invention in relation to disease conditions. For example, the present invention is particularly useful, but in no way limited to use in therapeutically or prophylactically treating parasitic infections such as by immunizing a mammal against a parasitic infection. In this regard, it should be understood that the method of the present invention is directed to inducing an immune response for the purpose of alleviating or preventing the onset of symptoms associated with a parasitic infection (such as toxicity and immunosuppression) and/or where the GPI domain is conjugated to a suitable antipathogen molecule, reducing or preventing parasitic infection. Reference herein to "symptoms" associated with a microorganism infection should be understood to extend to both the infection itself as well as the physical and/or physiological consequences (such as toxicity or immunosuppression) of such an infection.

Accordingly, another aspect of the present invention contemplates a method of therapeutically or prophylactically treating a mammal for a microorganism infection said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with infection of said mammal by said microorganism.

More particularly, the present invention is directed to a method of therapeutically or prophylactically treating a mammal for a microorganism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with infection of said mammal by said microorganism.

Preferably, said microorganism is a parasite and even more preferably *Plasmodium falciparum*.

In accordance with this preferred aspect of the present invention, the immunogenic composition preferably comprises a GPI inositolglycan domain wherein said GPI inositolglycan domain comprises the structure
ethanolamine-phosphate-(Manα1,2)-Manα1,2Manα1, 6Manα1,4GlcN-myo-inositol phosphoglycerol
or derivative or equivalent thereof.

In another preferred embodiment, the subject inositolglycan domain comprises the structure
$X_1$—$X_2$—$X_3$—$X_4$-ethanolamine-phosphate-(Manα1,2)-Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα2 Mα4Gα6Ino
Mα2 [Mα2][G]Mα6 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In yet still another preferred embodiment, the immunogenic composition comprises a GPI inositolglycan domain wherein said GPI inositolglycan domain comprises the structure
EtN-P-(Manα1,2)-6Manα1, 2Mα1, 6Manα1, 4GlcNH$_2$α1-myo-inositol-1,2 cyclic-phosphate
or derivative or equivalent thereof wherein EtN is ethanolamine, P is phosphate and M is mannose.

Even more preferably, the immunogenic composition comprises a GPI inositolglycan domain wherein said GPI inositolglycan domain comprises the structure
NH$_2$—CH$_2$—CH$_2$—PO$_4$-(Manα1-2) 6Manα1-2 Manα1-6Manα1-4GlcNH$_2$-6myo-inositol-1,2 cyclic-phosphate
or derivative or equivalent thereof.

The term "mammal" includes humans, primates, livestock animals (eg. horses, cattle, sheep, pigs, donkeys), laboratory test animals (eg. mice, rats, rabbits, guinea pigs), companion animals (eg. dogs, cats) and captive wild animals (eg. kangaroos, deer, foxes). Preferably, the mammal is a human or laboratory test animal. Even more preferably, the mammal is a human.

The mammal undergoing treatment may be a human or animal in need of therapeutic or prophylactic treatment for a disease condition or a potential disease condition.

Without limiting this aspect of the present invention, administration of said immunogenic composition may act to result in production of antibodies which either prevent manifestation of symptoms such as toxicity and immunosuppression or which affect the parasite directly, for example, by killing the parasite via binding to its surface and inhibiting its growth, development or the onward progression of the overall infection.

An "effective amount" means an amount necessary at least partly to attain the desired immune response, or to prevent or to delay the onset or inhibit progression or halt altogether, the onset or progression of a particular condition being treated. This amount varies depending upon the health and physical condition of the individual to be treated, the taxonomic group of individual to be treated, the capacity of the individual's immune system to synthesize antibodies, the degree of protection desired, the formulation of the vaccine, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of onset of a particular condition. "Treatment" may also reduce the severity of an existing condition or the frequency of acute attacks (for example, reducing the severity of initial infection).

In accordance with these methods, the modulatory agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules, These molecules may be administered in any order.

In a related aspect, the present invention provides a method for the treatment and/or prophylaxis of a mammalian disease condition characterised by a microorganism infection, said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with said microorganism infection.

More particularly, the present invention is directed to a method for the treatment and/or prophylaxis of a mammalian disease condition characterised by a microorganism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with said microorganism infection.

Preferably, said disease condition is malaria and said microorganism is *Plasmodium falciparum*.

In accordance with this preferred aspect of the present invention, the immunogenic composition preferably comprises a GPI inositolglycan domain wherein said GPI inositolglycan domain comprises the structure
ethanolamine-phosphate-(Manα1,2)-Manα1,2Manα1,6Manα1,4GlcN-myo-inositol phosphoglycerol
or derivative or equivalent thereof.

In another preferred embodiment, the subject inositolglycan domain comprises the structure
$X_1$—$X_2$—$X_3$—$X_4$-ethanolamine-phosphate-(Manα1,2)-Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2]-[EtN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα6 Mα4Gα6Ino
Mα2 [Mα2][G]Mα2 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα6 Mα4G
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In yet another aspect the present invention relates to the use of a composition comprising a molecule capable of inducing an immune response directed to a microorganism GPI inositolglycan domain but substantially incapable of inducing an immune response directed to a lipidic domain of GPI in the manufacture of a medicament for the therapeutic and/or prophylactic treatment of a mammalian disease condition characterised by infection with said microorganism.

In yet still another preferred embodiment, the immunogenic composition comprises a GPI inositolglycan domain wherein said GPI inositolglycan domain comprises the structure
EtN-P-(Manα1,2)-6Manα1, 2Manα1, 6Manα1, 4GlcNH$_2$α1-myo-inositol-1,2 cyclic-phosphate
or derivative or equivalent thereof wherein EtN is ethanolamine, P is phosphate and M is mannose.

Even more preferably, the immunogenic composition comprises a GPI inositolglycan domain wherein said GPI inositolglycan domain comprises the structure
NH$_2$—CH$_2$—CH$_2$—PO$_4$-(Manα1-2) 6Manα1-2 Manα1-6Manα1-4GlcNH$_2$-6myo-inositol-1,2 cyclic-phosphate
or derivative or equivalent thereof.

Accordingly, another aspect the present invention relates to the use of an immunogenic composition comprising a *Plasmodium* GPI inositolglycan domain or derivative or equivalent thereof which inositolglycan domain comprises insufficient lipidic domain of a *Plasmodium* GPI to elicit or induce an immune response directed to a GPI lipidic domain in the manufacture of a medicament for the therapeutic and/or prophylactic treatment of a mammalian disease condition characterised by infection with said *Plasmodium*.

Preferably said disease condition is malaria.

The present invention should also be understood to extend to immunogenic compositions for use in the methods as hereinbefore defined.

Accordingly, in a related aspect, the present invention is directed to a composition capable of inducing an immune response directed to a microorganism, said composition comprising a molecule capable of inducing an immune response against a microorganism GPI inositolglycan domain but substantially incapable of inducing an immune response to a lipidic domain of a GPI.

More particularly, the present invention is directed to a composition capable of inducing an immune response directed to a microorganism said composition comprising a modified GPI molecule or derivative or equivalent thereof which modified GPI molecule comprises insufficient lipidic domain to induce or elicit an immune response directed to a GPI lipidic domain.

Preferably, said modified GPI molecule is the inositolglycan domain portion of GPI.

Even more preferably, said microorganism is a parasite and said parasite is *Plasmodium*.

In accordance with this preferred aspect of the present invention, the immunogenic composition preferably comprises a GPI inositolglycan domain wherein said GPI inositolglycan domain comprises the structure
ethanolamine-phosphate-(Manα1,2)-Manα1,2Manα1, 6Manα1,4GlcN-myo-inositol phosphoglycerol
or derivative or equivalent thereof.

In another preferred embodiment, the subject inositolglycan domain comprises the structure
$X_1$—$X_2$—$X_3$—$X_4$-ethanolamine-phosphate-(Manα1,2)-Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα2 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα2 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In yet still another preferred embodiment, the immunogenic composition comprises a GPI inositolglycan domain wherein said GPI inositolglycan domain comprises the structure
EtN-P-(Manα1,2)-6Mα1,2Manα1, 6Manα1, 4GlcNH$_2$α1-myo-inositol-1,2 cyclic-phosphate
or derivative or equivalent thereof wherein EtN is ethanolamine, P is phosphate and M is mannose.

Even more preferably, the immunogenic composition comprises a GPI inositolglycan domain wherein said GPI inositolglycan domain comprises the structure
NH$_2$—CH$_2$—CH$_2$—PO$_4$-(Manα1-2) 6Manα1-2 Manα1-6Manα1-4GlcNH$_2$-6myo-inositol-1,2 cyclic-phosphate
or derivative or equivalent thereof.

Yet another aspect of the present invention relates to a vaccine composition comprising as the active component a molecule capable of inducing an immune response directed to a microorganism GPI inositolglycan domain but substantially incapable of inducing an immune response directed to a lipidic domain of a GPI, as broadly described above, together with one or more pharmaceutically acceptable carriers and/or diluents.

More particularly, the present invention relates to a vaccine composition comprising as the active component a modified GPI molecule or derivative or equivalent thereof which modified GPI molecule or derivative or equivalent thereof which modified GPI molecule comprises insufficient lipidic domain to induce or elicit an immune response directed to a GPI lipidic domain.

Preferably said modified GPI molecule is a GPI inositoglycan domain.

More preferably, said GPI inositolglycan domain is a parasite GPI inositolglycan domain and even more preferably a *Plasmodium* GPI inositolglycan domain.

Most preferably, said *Plasmodium* is *P. falciparum*.

In a most preferred embodiment, said molecule is a GPI inositolglycan domain comprising the structure
ethanolamine-phosphate-(Manα1,2)-Manα1,2Manα1, 6Manα1,4GlcN-phosphatidyl-myo-inositol phosphoglycerol.

In another most preferred embodiment said molecule is a GPI inositolglycan domain comprising the structure
$X_1$—$X_2$—$X_3$—$X_4$-ethanolamine-phosphate-(Manα1,2)-Manα1,2Manα1,6Manα1,4GlcN-myo-inositol phosphoglycerol
wherein $X_1$, $X_2$, $X_3$, $X_4$, are any 4 amino acids.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα6 Mα4G
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In yet still another preferred embodiment, the immunogenic composition comprises a GPI inositolglycan domain wherein said GPI inositolglycan domain comprises the structure
EtN-P-(Man$\alpha$1,2)-6M$\alpha$1, 2Man$\alpha$1, 6Man$\alpha$1, 4GlcNH$_2$$\alpha$1-myo-inositol-1,2 cyclic-phosphate
or derivative or equivalent thereof wherein EtN is ethanolamine, P is phosphate and M is mannose.

Even more preferably, the immunogenic composition comprises a GPI inositolglycan domain wherein said GPI inositolglycan domain comprises the structure
NH$_2$—CH$_2$—CH$_2$—PO$_4$-(Man$\alpha$1-2) 6Man$\alpha$1-2 Man$\alpha$1-6Man$\alpha$1-4GlcNH$_2$-6myo-inositol-1,2 cyclic-phosphate
or derivative or equivalent thereof.

Still another aspect of the present invention is directed to a pharmaceutical composition comprising a molecule capable of inducing an immune response directed to a microorganism GPI inositolglycan domain but substantially incapable of inducing an immune response directed to a lipidic domain of a GPI, as broadly described above, together with one or more pharmaceutically acceptable carriers and/or diluents.

The pharmaceutical forms suitable for injectable use include sterile aqueous solutions (where water soluble) and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of expressing, for example, a functional equivalent to a GPI inositolglycan domain or derivative thereof. The vector may, for example, be a viral vector and it may be administered by any suitable method including, for example transfection directly into the cells of the mammal being treated or transfection into a host cell, such as a bacterium, yeast or attenuated parasite, which is then introduced into the mammal.

Administration of the immunogenic GPI inositolglycan domain of the present invention induces antibody production and in particular IgG production. Said antibodies are involved in inhibiting, halting or delaying the onset or progression of symptoms associated with microorganism infection such as, for example, pathological responses to a parasitic infection. Said antibodies function, for example, by neutralizing parasite induced TNF induction or by direct antiparasitic effect such as killing the parasite by binding to its surface and inhibiting its growth or development or otherwise inhibiting its onward progression. Antibodies directed to the GPI inositolglycan domain or derivatives thereof may therefore also be utilized in treating parasitic infections therapeutically or prophylactically.

Accordingly, another aspect of the present invention is directed to antibodies to GPI inositolglycan domains but substantially incapable of interacting with the lipidic domain of a GPI.

Such antibodies may be monoclonal or polyclonal, may be of any isotyope and may be selected from naturally occurring antibodies to endogenous or exogenous GPI inositolglycan domains or may be specifically raised to GPI inositolglycan domains. Antibodies may also have been raised against antigens other than the GPI inositolglycan domain but are cross-reactive with one or more epitopes of the GPI inositolglycan domain. In the case of antibodies raised to the GPI inositolglycan domain, a GPI inositolglycan may first need to be associated with a carrier molecule as hereinbefore described.

The antibodies and/or GPI inositolglycan domains of the present invention are particularly useful as therapeutic or diagnostic agents. For example, a GPI inositolglycan domain can be used to screen for naturally occurring antibodies to GPI inositolglycan domain. These may occur, for example in some infectious and autoimmune diseases. Alternatively, specific antibodies can be used to screen for GPI inositolglycan domains. Techniques for such assays are well known in the art and include, for example, sandwich assays, ELISA, Western blot and flow cytometry. Knowledge of GPI inositolglycan domain levels may be important for diagnosis of certain diseases, such as parasitic infections, autoimmune diseases (e.g. Type 1 diabetes), degenerative diseases (e.g. Type 2 diabetes) and somatically acquired genetic defects (e.g. Paroxysmal Nocturnal Haemoglobinurea) or for monitoring certain therapeutic protocols. Said antibodies would be useful as research tools or reagents for the detection of GPI inositolglycan domains. Said antibodies would also be important for example as a means for screening for levels of GPI inositolglycan domains in cell extract or other biological fluid or purifying a GPI made by recombinant means from culture supernatant fluids. Techniques for the assays contemplated herein and known in the art and include, for example, sandwich assays and ELISA, Western blot and affinity chromatography.

Antibodies to GPI inositolglycan domain of the present invention may be monoclonal or polyclonal. Alternatively, fragments of antibodies may be used such as Fab fragments. Furthermore, the present invention extends to recombinant and synthetic antibody, to antibody hybrid and to humanised antibody. A "synthetic antibody" is considered herein to include fragments and hybrids of antibodies. The antibodies of this aspect of the present invention are particularly useful for immunotherapy and immunoprophylaxis and may also be used as a diagnostic tool for assessing, for example, parasitic infection or for monitoring the program of therapeutic regimen.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of the GPI inositolglycan domain.

Both polyclonal and monoclonal antibodies are obtainable by immunization with the GPI inositolglycan domain and are utilizable for immunoassays. The methods of obtaining both types of sera are well known in the art. Polyclonal sera are less preferred but are relatively easily prepared by injection of a suitable laboratory animal with an effective amount of a GPI inositolglycan domain, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Yet another aspect of the present invention relates to a pharmaceutical composition comprising an antibody directed to a GPI inositolglycan domain together with one or more pharmaceutically acceptable carriers or diluents as hereinbefore described.

A further aspect of the present invention relates to the use of the antibodies of the present invention in relation to disease conditions. For example, the present invention is particularly useful but in no way limited to use in treating parasitic infections, their symptoms and pathologies.

Accordingly, another aspect of the present invention relates to a method of inhibiting, halting or delaying the onset of progression of a mammalian disease condition characterised by a microorganism infection said method comprising administering to said mammal an effective amount of an antibody has hereinbefore described.

Preferably said disease condition is a parasite infection and most preferably malaria.

In yet another aspect the present invention relates to the use of an antibody in the manufacture of a medicament for inhibiting, halting or delaying the onset or progression of a disease condition characterised by the infection of a mammal by a microorganism.

Preferably said disease condition is a parasite infection and most preferably malaria.

In yet another further aspect, the present invention envisages diagnostic, monitoring, screening or other qualitative or quantitative antigen based assessments of either an immune response or a population of immunointeractive molecules directed to a microorganism, such as a parasite, utilizing the GPI inositolglycan molecules hereinbefore disclosed, in particular the synthetic GPI inositolglycan molecule disclosed herein.

Accordingly, another aspect of the present invention provides a method for detecting, in a biological sample, an immunointeractive molecule directed to a microorganism said method comprising contacting said biological sample with a molecule comprising said microorganism GPI inositolglycan domain or a derivative or equivalent thereof and qualitatively and/or quantitatively screening for said GPI inositolglycan domain-immunointeractive molecule complex formation.

In a related aspect, the present invention provides a method for detecting, monitoring or otherwise assessing an immune response directed to a microorganism in a subject said method comprising contacting a biological sample, from said subject, with a molecule comprising said microorganism GPI inositolglycan domain or a derivative or equivalent thereof and qualitatively and/or quantitatively screening for GPI inositolglycan domain-immunointeractive molecule complex formation.

Reference to "GPI inositolglycan domain" should be understood to have the same meaning as hereinbefore provided.

More particularly, according to these aspects of the present invention said GPI inositolglycan domain substantially does not contain a portion capable of inducing an immune response directed to a lipidic domain of said GPI. Most preferably, said GPI molecule is the inositolglycan domain portion of GPI or derivative or equivalent thereof.

Reference to "derivatives" and "equivalents" should be understood to have the same meaning as hereinbefore provided.

The term "microorganism" should be understood in its broadest sense and includes, for example, the parasitic and fungal taxa *Plasmodium, Trypanosoma, Leishmania, Toxoplasma* and *Canidida*. "Microorganism" should also be understood to extend to molecules which are secreted by or shed from the subject organism. This would include for example, toxin molecules or molecules which are cleared from the surface of the microorganism. Preferably, the GPI inositolglycan domain suitable for use in the present invention is a parasite GPI inositolglycan domain and even more preferably a *Plasmodium* GPI inositolglycan domain.

In one aspect, the present invention therefore more preferably provides a method for detecting, in a biological sample, an immunointeractive molecule directed to *Plasmodium* said method comprising contacting said biological sample with the inositolglycan domain portion of a *Plasmodium* GPI or derivative or equivalent thereof and qualitatively and/or quantitatively screening for GPI inositolglycan domain-immunointeractive molecule complex formation.

In a related aspect, the present invention more preferably provides a method for detecting, monitoring or otherwise assessing an immune response directed to *Plasmodium* in a subject said method comprising contacting a biological sample, from said subject, with the inositolglycan domain portion of a *Plasmodium* GPI or derivative or equivalent thereof and qualitatively and/or quantitatively screening for GPI inositolglycan domain-immunointeractive molecule complex formation.

Even more preferably, said *Plasmodium* is *P. falciparum*.

In one embodiment of these preferred aspects, said GPI inositolglycan domain comprises the structure
ethanolamine-phosphate-(Manα1,2)-Manα1,2Manα1,6Manα1,4GlcN-myo-inositol phosphoglycerol
or derivative or equivalent thereof.

In another embodiment of these preferred aspects said GPI inositolglycan domain comprises the structure
$X_1$—$X_2$—$X_3$—$X_4$-ethanolamine-phosphate-(Manα1,2)-Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another embodiment of these preferred aspects said GPI inositolglycan domain comprises the structure
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

Any of these structures may be further modified by substituents of positive, negative or neutral charge such as phosphates, phosphoglycerol, hexosamines, amino acids, thiols etc in any position and with any type of linkage. These structures may be further modified by addition of any number of amino acids for the purpose of providing a linkage sequence.

Most preferably, said GPI inositolglycan domain is a synthetic molecule and comprises the structure
EtN-P-(Manα1,2)-6Manα1, 2Manα1, 6Manα1, 4GlcNH$_2$α1-myo-inositol-1,2 cyclic-phosphate
or derivative or equivalent thereof wherein EtN is ethanolamine, P is phosphate and M is mannose; or
NH$_2$—CH$_2$—CH$_2$—PO$_4$-(Manα1-2) 6Manα1-2 Manα1-6Manα1-4GlcNH$_2$-6myo-inositol-1,2 cyclic-phosphate
or derivative or equivalent thereof.

Reference to "biological sample" should be understood as a reference to any sample of biological material derived from an individual such, but not limited to, mucus, stool, urine, blood, serum, cell extract, biopsy specimens and fluid which has been introduced into the body of an individual and subsequently removed such as, for example, the saline solution extracted from the lung following lung lavage or the solution retrieved from an enema wash. The biological sample which is tested according to the method of the present invention may be tested directly or may require some form of treatment prior to testing. For example, a biopsy sample may require homogenisation or sectioning prior to testing. Alternatively, the sample may require some other form of treatment in order to render it suitable for analysis. Preferably, the subject sample is a blood sample.

The "immunointeractive molecule" is any molecule having specificity and binding affinity for the GPI inositolglycan domain or its antigenic parts. Although the preferred immunointeractive molecule is an immunglobulin molecule, the present invention extends to other immunointeractive molecules such as antibody fragments, single chain antibodies, deimmunized including humanized antibodies and T-cell associated antigen-binding molecules (TABMs). Most preferably, the immunointeractive molecule is an antibody such as a polyclonal or monoclonal antibody. It should be understood that the subject immunointeractive molecule may be linked, bound or otherwise associated to any other proteinaceous or non-proteinaceous molecule or cell. Most preferably, the antibody is a monoclonal antibody.

The immunointeractive molecule exhibits specificity for GPI or more particularly an antigenic determinant or epitope of the GPI inositolglycan domain. An antigenic determinant or epitope of the GPI inositolglycan domain includes that part of the molecule to which an immune response can be directed. The antigenic determinant or epitope is preferably a B-cell epitope but may be, where appropriate, a T-cell receptor binding peptide. The term "antigenic part" includes an antigenic determinant or epitope.

One aspect of the present invention therefore most preferably provides a method for detecting, in a biological sample, an antibody directed to *Plasmodium* said method comprising contacting said biological sample with the inositolglycan domain portion of a *Plasmodium* GPI or a derivative or equivalent thereof and qualitatively and/or quantitatively screening for GPI inositolglycan domain-antibody complex formation.

A related aspect of the present invention most preferably provides a method for detecting, monitoring, or otherwise assessing an immune response directed to *Plasmodium* in a subject said method comprising contacting a biological sample, from said subject, with the inositolglycan domain portion of a *Plasmodium* GPI or a derivative or equivalent thereof and qualitatively and/or quantitatively screening for GPI inositolglycan domain-antibody complex formation.

Most preferably, said *Plasmodium* is *P. falcimparum*.

Reference to "immune response" should be understood as a reference to any form of specific immune response. Preferably, the subject response is a B cell/antibody response. It should also be understood that the subject immune response may be at any stage of development. For example, in a most preferred embodiment, one screens for secreted anti-*Plasmodium* antibodies (i.e. the onset of the effector B cell response). However, one may also apply the method at a cellular level to screen for or otherwise analyse the expansion and/or maturity of the B cell sub-population which is directed to the *Plasmodium* GPI inositolglycan domain and will therefore provide protective immunity. Although the preferred method is to assess the onset of an immune response in a subject it should be understood that the present invention also encompasses the analysis of in vitro-based immune responses, such as those which occur in the context of generating or analysing B cell hybridomas.

Reference to "detecting, monitoring or otherwise assessing" an immune response or immunointeractive molecule should be understood as a reference to any form of analysis which one may seek to perform in the context of the subject immune response including, but not limited to:

(i) assessing the existence, onset or degree of clinical immunity of individuals. This extends to assessing the seroconversion of vaccinated individuals as well as determining the degree of naturally acquired anti-toxin antibodies. As shown in Example 18, the GPI glycan can be used to detect antibodies from glycan immunized mice. Identical glycan:protein coupling methods have also been used to generate glycan:protein constructs capable of detecting IgG in the sera of humans exposed to malaria. These antibodies confer protective clinical immunity to malaria and individuals may acquire such immunity after exposure to malaria infection. The detection of such antibodies may be useful to indicate the clinical immune status of individuals. For example, following mass vaccination campaigns it is desirable to assess the seroconversion of target groups and the GPI glycan will have utility as an indicator of such seroconversion.

(ii) determining whether an immune response is of a primary (e.g. IgM) or secondary (IgG) type. This can have particular relevance to postulating whether an individual's parasitic infection status is acute or chronic.

(iii) monitoring disease progression, for example in the context of assessing the effectiveness of a therapeutic response (iv) detecting, and thereby potentially facilitating the isolation and analysis of, antibodies which neutralise parasite derived toxins, such as the malaria toxin.

(v) detecting, and thereby potentially facilitating the isolation and analysis of, monoclonal or polyclonal antibodies of animal or human origin which are directed towards the parasite GPI inositolglycan domain and which would therefore exhibit utility in the treating of disease.

The present invention is therefore useful as a one off test or as an ongoing monitor in either in vitro or in vivo contexts. Accordingly, the method of the present invention should be understood to extend to monitoring for increases or decreases in levels of GPI antibody complex formation relative either to normal levels (as hereinafter defined) or relative to one or more earlier levels as determined for a given situation. In this regard, "qualitatively and/or quantitatively screening for" GPI-antibody complex formation should be understood to encompass both screening for the presence or absence of complex formation or screening for the level of complex formation either for the purpose of obtaining an absolute quantitative value or for the purpose of correlation with normal levels or earlier obtained levels. The "normal" level is the level of complex in a biological sample corresponding to an individual who either is not infected or has not yet developed an immune response. This "normal" level may be a standard result which reflects individual or collective results obtained from healthy individuals, other than the patient in issue. Said "normal level" may be a discrete level or a range of levels. Individuals exhibiting complex levels higher than the normal range are generally regarded as having undergone the onset or expansion of an immune response directed to a parasite infection.

The method of the present invention has widespread applications as detailed hereinbefore. Also detailed hereinbefore is the fact that the screening methodology may be performed either qualitatively or quantitatively. Although it is likely that quantitative analyses will be preferred since it provides information in relation to the occurrence of, or not, of an immune response or the presence of a particular population of immunointeractive molecules, qualitative analyses may also be of value. In particular, since antibodies to parasite derived cell molecules are not normally found in the blood of uninfected individuals, a test directed to assessing the presence or not of the subject immunointeractive molecules will provide useful information. It will also provide scope for establishing extremely simple and inexpensive screening procedures.

Methods of designing and performing such diagnostic screening assays would be well known to the person of suitable skill in the art and include, but are not limited to:

(i) In vivo detection of complex formation. Molecular Imaging may be used following administration of imaging reagents capable of disclosing altered levels of immunointeractive molecule expression product in the subject.

Molecular imaging (Moore, A., Basilion, J., Chiocca, E., and Weissleder, R., *BBA*, 1402:239-249, 1988; Weissleder, R., Moore, A., Ph.D., Mahmood-Bhorade, U., Benveniste, H., Chiocca, E. A., Basilion, J. P. *Nature Medicine*, 6:351-355, 2000) is the in vivo imaging of molecular expression that correlates with the macro-features currently visualized using "classical" diagnostic imaging techniques such as X-Ray, computed tomography (CT), MRI or Positron Emission Tomography (PET).

(ii) Measurement of altered complex levels in a suitable biological sample, either qualitatively or quantitatively, for example by immunoassay. For example, a secondary antibody having a reporter molecule associated therewith, may be utilised in immunoassays to detect complex formation. Such immunoassays include but are not limited to radioimmunoassays (RIAs), enzyme-linked immunosorbent assays (ELISAs) and immunochromatographic techniques (ICTs), Western blotting which are well known to those of skill in the art. For example, reference may be made to "Current Protocols in Immunology", 1994 which discloses a variety of immunoassays which may be used in accordance with the present invention. Immunoassays may include competitive assays. It will be understood that the present invention encompasses qualitative and quantitative immunoassays.

Suitable immunoassay techniques are described, for example, in U.S. Pat. Nos. 4,016,043, 4,424,279 and 4,018,653. These include both single-site and two-site assays of the non-competitive types, as well as the traditional competitive binding assays.

Two-site assays are particularly favoured for use in the present invention. A number of variations of these assays exist, all of which are intended to be encompassed by the present invention. Briefly, in a typical forward assay, an unlabelled antigen molecule (i.e. GPI) is immobilized on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of primary antibody. Variations on the forward assay include a simultaneous assay, in which both sample and labelled antibody are added simultaneously to the bound antigen. These techniques are well known to those skilled in the art, including minor variations as will be readily apparent.

In the typical forward assay, the GPI molecule having specificity for the immune response effector immunointeractive molecule is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antibody present to the GPI antibody. Following the incubation period, the antigen-antibody complex is washed and dried and incubated with a second antibody specific for a portion of the antibody. The second antibody has generally a reporter molecule associated therewith that is used to indicate the binding of the second antibody to the first antibody. The amount of labelled antibody that binds, as determined by the associated reporter molecule, is proportional to the amount of first antibody bound to the immobilized antigen.

From the foregoing, it will be appreciated that the reporter molecule associated with the antigen-binding molecule may include the following:—

(a) direct attachment of the reporter molecule to the antibody;
(b) indirect attachment of the reporter molecule to the antibody; i.e., attachment of the reporter molecule to another assay reagent which subsequently binds to the antibody; and
(c) attachment to a subsequent reaction product of the antibody.

The reporter molecule may be selected from a group including a chromogen, a catalyst, an enzyme, a fluorochrome, a chemiluminescent molecule, a paramagnetic ion, a lanthanide ion such as Europium ($Eu^{34}$), a radioisotope including other nuclear tags and a direct visual label. In the case of a direct visual label, use may be made of a colloidal metallic or nonmetallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. No. 5,573,909 (Singer et al), U.S. Pat. No. 5,326,692 (Brinkley et al). Alternatively, reference may be made to the fluorochromes described in U.S. Pat. Nos. 5,227,487, 5,274,113, 5,405,975, 5,433, 896, 5,442,045, 5,451,663, 5,453,517, 5,459,276, 5,516, 864, 5,648,270 and 5,723,218.

In the case of an enzyme immunoassay, an enzyme is conjugated to the second antibody, generally by means of glutaraldehyde or periodate. As will be readily recognized, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

(iii) Determining altered antibody production on any suitable functional test, enzymatic test or immunological test in addition to those detailed in point (iii)-above.

As detailed above, any suitable technique may be utilised to detect the anti-parasite antibody. The nature of the technique which is selected for use will largely determine the type of biological sample which is required for analysis. Such determinations are well within the scope of the person of skill in the art. A typical sample which one may seek to analyse is a blood sample.

The present invention further provides a kit for detecting an immune response to a parasitic infection. The kit may be in any convenient form but generally comprises a solid support such as described herein adapted to receive or comprise the GPI molecule hereinbefore defined. The kit may also comprise reagents, reporter molecules capable of providing detectable signals and optionally instructions for use. The kit may be in modular form wherein individual components may be separately purchased.

Accordingly, another aspect of the present invention is directed to a modular kit comprising one or more members wherein at least one member is a solid support comprising a GPI molecule as hereinbefore defined.

In an alternative embodiment, the solid support comprises an array of binding partners for said GPI molecule.

The kit may optionally be adapted to be analyzed electronically or spectrophotometrically or fluorometrically and may further be adapted for high throughput screening.

In another related aspect, the determination that the GPI inositolglycan domain, in particular the synthetic form of this molecule, facilitates the highly valuable analysis of the onset and monitoring of the crucial aspects of the parasite specific effector immune response still further facilitates rationalizing the design of anti-toxic vaccines. Human IgG directed towards the GPI glycan exhibits epitopic specificity for smaller partial structures within the glycan. Mapping these epitopes using synthetic GPIs enables reduction of the number of residues required for incorporation into a final vaccine. Furthermore to the extent that some epitopes are "self" and others "non-self", the use of GPI glycan and fragments thereof to map these specificities enhances immunogenicity and safety of the final product. Accordingly, the detection of human IgG by the glycan is crucial for downstream "medicinal chemistry" rationalization of vaccine structure.

Preferably said immunointeractive molecule is an antibody.

Accordingly, the present invention should also be understood to extend to a method for analysing, designing and/or modifying an agent capable of interacting with an anti-GPI glycan immunointeractive molecule binding site, which immunointeractive molecule is identifiable utilising the diagnostic methodology hereinbefore disclosed, said method comprising contacting said immunointeractive molecule or derivative thereof with a putative agent and assessing the degree of interactive complementarity of said agent with said binding site.

It should be understood that the immunointeractive molecule, for example an antibody, which is contacted with the putative agent, for example a synthetic GPI glycan molecule, for evaluation of interactive complementarity may be recombinantly produced subsequently to its identification. However, it should also be understood that the subject molecule may take the form of an image based on the binding site structure which has been elucidated, such as an electron density map, molecular models (including, but not limited to, stick, ball and stick, space filling or surface representation models) or other digital or non-digital surface representation models or image, which facilitates the analysis of molecule site: agent interactions utilising techniques and software which would be known to those of skill in the art. For example, interaction analyses can be performed utilising techniques such as Biacore real-time analysis of on and off-rates and dissociation constants for binding of ligands (Gardsvoll, H., Dano, K., and Ploug, M., (1999), *J Biol Chem*, 274(53):37995-38003; Hoyer-Hansen, G., Behrendt, N., Ploug, M., Dano, K., and Preissner, K. T., (1997), *FEBS Lett*, 420(1):79-85; Ploug, M., (1998), *Biochemistry*, 37(47): 16494-16505; Ploug, M., Ostergaard, S., Hansen, L. B., Holm, A., and Dano, K., (1998), *Biochemistry*, 37(11):3612-3622; Ploug, M., Rahbek-Nielsen, H., Ellis, V., Roepstorff, P., and Dano, K., (1995), *Biochemistry*, 34(39):12524-12534; Ploug, M., Ellis, V., and Dano, K., (1994), *Biochemistry*, 33(30):8991-8997) and NMR perturbation studies (Stephens, R. W., Boklman, A. M., Myohanen, H. T., Reisberg, T., Tapiovaara, H., Pedersen, N., Grondahl-Hansen, J., Llinas, M., and Vaheri, A., (1992), *Biochemistry*, 31:7572-7579).

Reference to "assessing the degree of interactive complementarity" of an agent with the subject molecule should be understood as a reference to elucidating any feature of interest including, but not limited to, the nature and/or degree of interaction between the subject molecule and an agent of interest. As detailed above, any suitable technique can be utilised. Such techniques would be known to the person of skill in the art and can be utilised in this regard. In terms of the nature of the subject interaction, it may be desirable to assess the types of interactive mechanisms which occur between specific residues of any given agent and those of the molecule (for example, peptide bonding or formation of hydrogen bonds, ionic bonds, van der Waals forces, etc.) and/or their relative strengths. It may also be desirable to assess the degree of interaction which occurs between an agent of interest and the subject molecule. For example, by analysing the location of actual sites of interaction between the subject agent and molecule it is possible to determine the quality of fit of the agent into a region of the molecule and the relative strength and stability of that binding interaction. The form of association which occurs may not necessarily involve the formation of any chemical interactive bonding mechanism, as this is traditionally understood, but may involve a non-bonding mechanism such as the proximal location of a region of the agent relative to a binding region of the molecule, for example, to effect steric hindrance with respect to the binding of an activating molecule. Where the interaction takes the form of hindrance or the creation of other repulsive forces, this should nevertheless be understood as a form of "interaction" despite the lack of formation of any of the traditional forms of bonding mechanisms.

It should also be understood that the molecule which is utilised either in a physical form or as an image, as hereinbefore discussed, to assess the interactive complementarity of a putative agent may be a naturally occurring form of the molecule or it may be a derivative, homologue, analogue, mutant, fragment or equivalent thereof. The derivative, homologue, analogue, mutant, fragment or equivalent thereof may take either a physical or non-physical (such as an image) form.

The development of methodology for screening for GPI glycan immunointeractive molecules in the context of the diagnostic applications hereinbefore described facilitates determination of the three dimensional structure of the immunointeractive molecule's binding site and the identification and/or rational modification and design of agents which can interact with this site, for example, in the context of anti-toxic vaccine development.

Without limiting the application of the present invention in any way, the method of the present invention facilitates the analysis, design and/or modification of agents capable of interacting with these immunointeractive molecules. In this regard, reference to "analysis, design and/or modification" of an agent should be understood in its broadest sense to include:

(i) Randomly screening (for example, utilising routine high-throughput screening technology) to identify agents which interact with the subject molecule. In this regard, crystals could be soaked with said agents or co-crystalisation could be performed. Such agents are often commonly referred to as "lead" agents in terms of the random screening of proteinaceous or non-proteinaceous molecules for their capacity to function in a desired manner. Further, for example, binding affinity and specificity could be enhanced by modifying lead agents to maximise interactions with the molecule. Such analyses would facilitate the selection of agents which are the most suitable for a given purpose. In this way, the selection step is based not only on in vitro data but also on a technical analysis of sites of agent: molecule interaction in terms of their frequency, stability and suitability for a given purpose. For example, such analysis may reveal that what appears to be an acceptable in vitro activity in respect of a randomly identified agent is in fact induced by a highly unstable interaction due to the presence of proximally located agent: molecule sites which exhibit significant repulsive forces thereby de-stabilising the overall interaction between the agent and the molecule. This would then facilitate the selection of another prospective lead compound, exhibiting an equivalent degree of in vitro activity, but which agent does not, upon further analysis, involve the existence of such de-stabilising repulsive forces.

Screening for the agents herein defined can be achieved by any one of several suitable methods, including in silico methods, which would be well known to those of skill in the art and which are, for example, routinely used to randomly screen proteinaceous and non-proteinaceous molecules for the purpose of identifying lead compounds.

These methods provide a mechanism for performing high throughput screening of putative modulatory agents such as the proteinaceous or non-proteinaceous agents comprising synthetic, recombinant, chemical and natural libraries.

(ii) The candidate or lead agent (for example, the agent identified in accordance with the methodology described in relation to point (i)) could be modified in order to maximise desired interactions (for example, binding affinity to specificity) with the molecule and to minimise undesirable interactions (such as repulsive or otherwise de-stabilising interactions).

Methods of modification of a candidate or lead agent in accordance with the purpose as defined herein would be well known to those of skill in the art. For example, a molecular replacement program such as Amore (Navaza, J., (1994), *Acta Cryst, A*50:157-163) may be utilised in this regard. The method of the present invention also facilitates the mutagenesis of known signal inducing agents in order to ablate or improve signalling activity.

(iii) In addition to analysing fit and/or structurally modifying existing molecules, the method of the present invention also facilitates the rational design and synthesis of an agent, based on theoretically modelling an agent exhibiting the desired interactive structural features followed by the synthesis and testing of the subject agent.

It should be understood that any one or more of applications (i)-(iii) above, may be utilised in identifying a particular agent.

The present invention also extends to the use of the molecules generated in accordance with this aspect of the present invention in accordance with the therapeutic, prophylactic and diagnostic methods hereinbefore described.

The present invention is further described by the following non-limiting Examples.

Example 1

Reagents, Animals and Preparation of Parasites

Pronase was obtained from Boehringer Mannheim. Phosphatidylinositol-specific phospholipase C was from Calbiochem. Octyl-Sepharose, Protein-G Sepharose, n-octylthioglucopyranoside (n-otg), phenylmethylsulfonylfluoride (PMSF), p-tosyl-L-lysine-chloromethylketone (TLCK), N-tosyl-L-phenylalaninechloromethylketone (TLCK), p-chloro-mercuriphenylsulphonic acid (p-CMPS), aprotinin, leupeptin, pepstatin, iodoacetamide, n-ethyl-maleimide (NEM), and Concanavalin-A were obtained from Sigma Chemical Co. Sephadex was from Pharmacia. Biogel P4 was from Biorad. Analytical or HPLC grade, acetic acid, butanol, chloroform, diethyl ether, ethanol, methanol and water were obtained from BDH and Waters. Silica G60 TLC plates were from Merck Darmstadt. Tritiated mannose, glucosamine, myristic and palmitic acids were from Amersham.

Adult female C57BL/6 and C3H/HeJ mice were bred and maintained in the Walter and Eliza Hall Institute specific pathogen free animal facility.

The FCB-1 line of *Plasmodium falciparum* were grown in vitro by standard methods, and confirmed free of *Mycoplasma* contamination. For the biosynthetic labelling of parasite proteins, 3H-palmitic acid conjugated to defatted bovine serum albumin in molar ratio 1:1, 3H-glucosamine or 3H-mannose were added at a final specific activity of 10 µCurie/ml, to RPMI 1640 cultures of $2 \times 10^{10}$ parasites at the late trophozoite/early schizont stage for 2 hours (for labelling of GPI precursors) or 8 hours (for labelling of protein-bound GPI). Parasites were harvested by 0.05% Saponin lysis and centrifugation in the cold at 15,000 g for 20 minutes, followed by two washes in PBS and storage at −70° C.

Example 2

Purification of the 195 KD MSP-1 and 56 KD MSP-2 Antigens

The GPI-anchored MSP-1 and MSP-2 merozoite surface proteins were purified to homogeneity as described previously (Schofield and Hackett (1993), supra). Biosynthetically labelled malaria parasites at the late schizont stage were lysed in 0.05% Saponin and centrifuged at 15,000 g for 20 minutes, and washed as above. The pellet was extracted in 25 mM n-octyl-thioglucopyranoside (n-otg), 1% BSA, 1 mM EDTA, 0.1M EGTA, 1 mM PMSF, 1 mM TLCK, 0.1 mM TLCK, 5 mM pCMPS, 1 µg/ml pepstatin, 1 µg/ml leupeptin, 1 mM NEM, 5 mM iodoacetamide, 150 mM NaCl, 25 mM Tris/HCl pH 7.4 by sonication on ice. The extract was clarified by centrifugation at 20,000 g for 30 minutes in the cold, and the supernatant decanted and loaded onto two immunoaffinity columns arranged in sequence, containing approximately 10 mg monoclonal antibody 111.4 or monoclonal antibody 113.1, each cross-linked to Protein G-Sepharose by gluteraldehyde (all procedures on ice). The protein extract was passed through the column at a rate of 0.3 ml/min. The columns were washed first with 100 ml 10 mM n-otg, 1% BSA, 300 mM NaCl, followed by 100 ml 10 mM n-otg, 300 mM NaCl. Antigen was eluted from each column with four column volumes of 10 mM n-otg, 200 mM glycine pH 2.8. The pH of the eluate was neutralized with 2M Tris. Aliquots of protein were analysed for purity by SDS-PAGE followed by staining with Coomassie brilliant blue. The remaining purified proteins were dialysed exhaustively against 100 mM NH$_4$HCO$_3$ using dialysis membrane previously boiled exhaustively in 10 mM EDTA followed by boiling in 10 changes of double distilled water. Protein concentration was determined by standard methods.

The remaining detergent soluble extract was made up to 1 mM CaCl$_2$, 1 mM MgCl$_2$, and 1 mM MnCl$_2$, and passed over a Con-A sepharose column, followed by washing with 10 column volumes of extraction buffer. The column was first eluted with detergent buffer containing 0.5M α-methyl-mannopyranoside and 0.5M α-glucopyranoside, followed by 25 mM n-otg in 8M urea. Aliquots were subject to SDS-PAGE and fluorography or staining with Coomassie blue.

Example 3

Purification of the C-Terminal GPI Anchors of Defined Parasite Antigens

To purify the intact C-terminal GPIs free of detergent, non-covalently bound lipids, glycolipids, phospholipids and protein or peptide fragments, affinity purified MSP-1 and MSP-2 were first scrubbed with organic solvents. 10 mg/ml GPI-anchored proteins were placed in 150 µl aliquots in clean glass tubes. 600 µl MeOH was added and vortexed, followed by 150 µl 1 Chloroform and 450 µl water and further vortexing. The samples were centrifuged at 14000 rpm for 3 min, the supernatant discarded, and the interphase and lower phase mixed with 450 µl MeOH and re-centrifuged at 14000 rpm for 3 min. The protein pellet was extracted 5 times with C/M/W 10:10:3, and finally extracted with acetone over night at −20° C. The acetone was removed completely and the proteins taken up with sonication in 6M Urea, 1 mM DTT, 1 mM iodoacetic acid. After 15 minutes at room temperature, the sample was diluted 6 fold and made to 5 mM CaCl$_2$. 2.5% pre-digested Pronase B was added for 72 h at 37° C. with 2 additions of 0.3% pronase. The digested sample was phase separated between water and water-saturated butanol, and the organic phase back extracted with water. The butanol phase was spotted onto TLC plates (Si-60) and run in the solvent system C/M/HAc/W 25:15:4:2. The pronase-digested GPI fragment free of contaminants remains close to the origin, and was detected by Berthold Digital Autoradiograph. The appropriate region was scraped and the material eluted twice with C/M/W 10:10:3 followed by 40% 1-propanol in water. The material was dried under nitrogen gas, and once more separated between water and water-saturated butanol.

Example 4

Purification of GIPLs and GPI Biosynthetic Precursors by TLC

GPI biosynthetic intermediates and non-protein bound mature GPI species were purified by TLC. $2 \times 10^{10}$ *P. falciparum* schizonts were labelled with 1 mCi $^3$[H]-mannose or $^3$[H]-palmitic acid in 250 ml glucose deficient RPMI 1640 supplemented with 40 mM fructose and 0.5% Albumax (GIBCO) for 2 hours. Parasites were harvested by saponin lysis and washed twice in PBS. They were extracted three times in chloroform/methanol (2:1) and three times in chloroform/methanol/water (1:1:0.3). The chloroform/methanol extracts were subject to repeated Folch washing and the chloroform phase dried in a Speedvac. The chloroform/methanol/water extracts were dried down and partitioned between water and water-saturated butanol. The butanol phase was washed with water and dried in a Speedvac. Both residues were then separated by TLC and the plates scanned by Bertold Digital Autoradiograph TLC scanner. The radiolabelled peaks were identified and removed by scraping and re-extraction followed by drying. Areas lying between and outside the identifiable peaks were treated in the same way, as were sham plates. In some experiments, the GPIs were further purified over Octyl-Sepharose. Samples were taken up in 5% 1-propanol in 100 mM Ammonium acetate and loaded at a flow rate of 0.1 ml/min onto an Octyl-Sepharose column, and the column washed with 100 mM Ammonium acetate, 5% 1-propanol. The column was eluted in a gradient running from 10 mM Ammonium acetate, 5% 1-propanol to 60% 1-propanol in water. GPI containing fractions were lyophilised and flash evaporated in methanol.

Example 5

Generation of Chemical and Enzymatic Hydrolysis Fragments of GPIs

Purified, glucosamine-labelled *P. falciparum* GPIs, in which all dpms were detected in the organic phase following butanol/water partitioning, were subject to base hydrolysis by suspension in methanol/ammonia 1:1 for 6 hours at 50° C., followed by partitioning between water and water saturated butanol. Essentially 100% of label was then recovered from the aqueous phase. The aqueous phase was twice extracted with water-saturated butanol, lyophilized, and flash evaporated with methanol.

Example 6

DEAE Anion Exchange Chromatography

GPIs were loaded onto a A DEAE column in 99% methanol, 1% water and washed with ten column volumes of solvent. They were subsequently eluted in 100 mM Ammonium Acetate in 99% methanol, 1% water and dried under Nitrogen.

Example 7

Biogel P4 Size-Exclusion Chromatography

Ease-hydrolysed GPI glycans were spiked with phenol red and blue dextran in 10 mM Ammonium Acetate and further size-fractionated by passage through a 1 cm×1.2 meter Biogel P4 column equilibrated in 100 mM Ammonium acetate in water. The column had previously been exhaustively calibrated by repeated analytical runs with GPI mixed with acid hydrolyzed dextran markers to yield the relative elution position of glucose units detected by staining with orcinol in concentrated sulfuric acid. The column runs proved to be highly reproducible. For preparative purposes the dextran markers were omitted. The GPI peak was detected by scintillation counting of aliquots.

Example 8

Compositional Analysis by GC/MS

Glycan concentration and compositional purity was determined by GC-MS, following acid methanolysis and trimethylsilyl (TMS) derivatization. myo-Inositol content was measured following acid hydrolysis (6N HCl, 110° C., 16 h) and TMS derivatization, with selected ion monitoring for m/z 305 and 318. scyllo-Inositol was used as internal standard throughout.

Example 9

Coupling of GPI Glycan to Maleimide-Activated KLH

The GPI glycan was exposed to 1 mM Traut's reagent (2-iminothiolane) in 60 mM triethanolamine, 7 mM potassium phosphate, 100 mM NaCl, 1 mM EDTA, pH 8.0 in the cold for 90 minutes under nitrogen. The sample was then desalted by gel filtration at 4° C. through a small Biogel P4 column equilibrated in 7 mM potassium phosphate, 100M NaCl, 1 mM EDTA, pH 7.2 and added to maleimide-activated KeyHole Limpet Haemocyanin (KLH) or Ovalbumin (OVA) in coupling buffer (7 mM potassium phosphate, 100 mM NaCl, 1 mM EDTA, pH 7.2) overnight. The degree of conjugation was estimated by comparison of cpms before and after dialysis of the sample against PBS, or by use of Ellman's reagent for the quantitation of sulfhydryl groups. Excess reactive sites were blocked with cysteine.

Example 10

Epitope Mapping of Anti-GPI Antibodies

Coupling of the purified GPI glycan to proteins was undertaken as above. To measure anti-lipid reactivities, we utilized commercially available phosphatidylinositol from Sigma with identical composition to the malarial GPI, namely dipalmitoyl-PI. 2 mg PI was coupled to defatted BSA according to published protocols (Bate, C. A. W., Taverne, J., Kwiatkowski, D., and Playfair, J. H. L. (1993) Immunology 79:138-145).

Example 11

ELISA Assay

Antigen (GPI-OVA, Glycan-OVA, BSA-PI, OVA or BSA alone) at 20 µg/ml in phosphate binding buffer was incubated overnight in 50 µl volumes in flat-bottomed Immunlon 96-well plates, followed by extensive washing with buffer. The plates were blocked with 1% BSA, 1% OVA in PBS for several hours. From a 1/32 dilution, sera were titrated two-fold in 1% BSA, 1% OVA in PBS, and 50 l aliquots incubated in triplicate for 2 hours at room temperature, followed by extensive washing with 1% BSA, 1% OVA 0.05% Tween-20 in PBS. An aliquot of affinity purified, biotin-labelled isotype specific goat anti-mouse second antibody was incubated as above, followed by further washing and the addition of streptavidin-alkaline phosphatase. After 30 minutes the plates were washed again and colourimetric development initiated by the addition of p-Nitrophenylphosphate in diethanolamine buffer. Background binding to BSA/OVA-coated plates was determined in parallel. The end-titres derived are the last point giving values statistically different by two-way analysis of variance from non-specific binding by the same serum to the BSA/OVA-coated plates.

Example 12

Competition ELISA

From a 1/32 dilution, sera or mAbs were titrated two-fold in 1% BSA in PBS, 0.05% Tween-20, and pre-incubated for 4 hours at room temperature with a molar excess of competitior (20 µg/ml PI, or phosphatidylserine (PS), or diluent alone). Antigen (BSA-PI or BSA alone) at 20 µg/ml in phosphate binding buffer was incubated overnight in 50 µl volumes in flat-bottomed Immunlon 96-well plates, followed by extensive washing with buffer. The plates were blocked with 1% BSA in PBS for several hours. 50 µl aliquots of titrated antibody with or without competitor were incubated in triplicate for 2 hours at room temperature, followed by extensive washing with 1% BSA 0.05% Tween-20 in PBS. An aliquot of affinity purified, biotin-labelled isotype specific goat anti-mouse second antibody was incubated as above, followed by further washing and the addition of streptavidin-alkaline phosphatase. After 30 minutes the plates were washed again and colourimetric development initiated by the addition of p-Nitrophenylphosphate in diethanolamine buffer. Background binding to BSA-coated plates was determined in parallel. The end-titres derived are the last point giving values statistically different by two-way analysis of variance from non-specific binding by the same serum to the BSA-coated plates.

Example 13

Production of Monoclonal Antibodies

Monoclonal antibodies to the lipid domain of the GPI were produced as previously described (Tachado et al (1996) supra). Monoclonal antibodies to the glycan were generated by immunization of OVA-TCR transgenic mice on a Balb/c background with OVA-glycan, followed by fusion and screening of hybridoma culture supernatants against BSA vs. BSA-glycan.

Example 14

Macrophage Culture and TNF Output

LPS-nonresponsive C3H/HeJ macrophages were obtained as previously described (Schofield and Hackett (1993), supra and Tachado et al (1996) supra). $2 \times 10^5$ adherent cells/well were given medium alone or test agents. 3 hrs after incubation TNF-α levels in the supernatant and standard curve were determined by capture ELISA (Pharmingen).
Tyrosine Phosphorylation.

Rapid onset tyrosylphosphorylation was determined as previously described (Tachado et al (1997), supra).

Example 15

PI-PLC Treatment and FACS Analysis $2 \times 10^5$ cells were exposed to 1 U/ml PI-PLC at 37° C. for 2 hours, followed by washing. They were then incubated in ice cold murine tonicity RPMI 1640 with 0.05% Sodium azide and 1% BSA with monoclonal antibodies or murine sera followed by washing and a further incubation with isotype-specific FITC-conjugated antibody to mouse immunoglobulins. After washing in the same medium the cells were counter-stained with 0.5 μg/ml propidium iodide and analysed by FACSscan.

Example 16

Immunization of Mice with Free GPI

Figure 1:
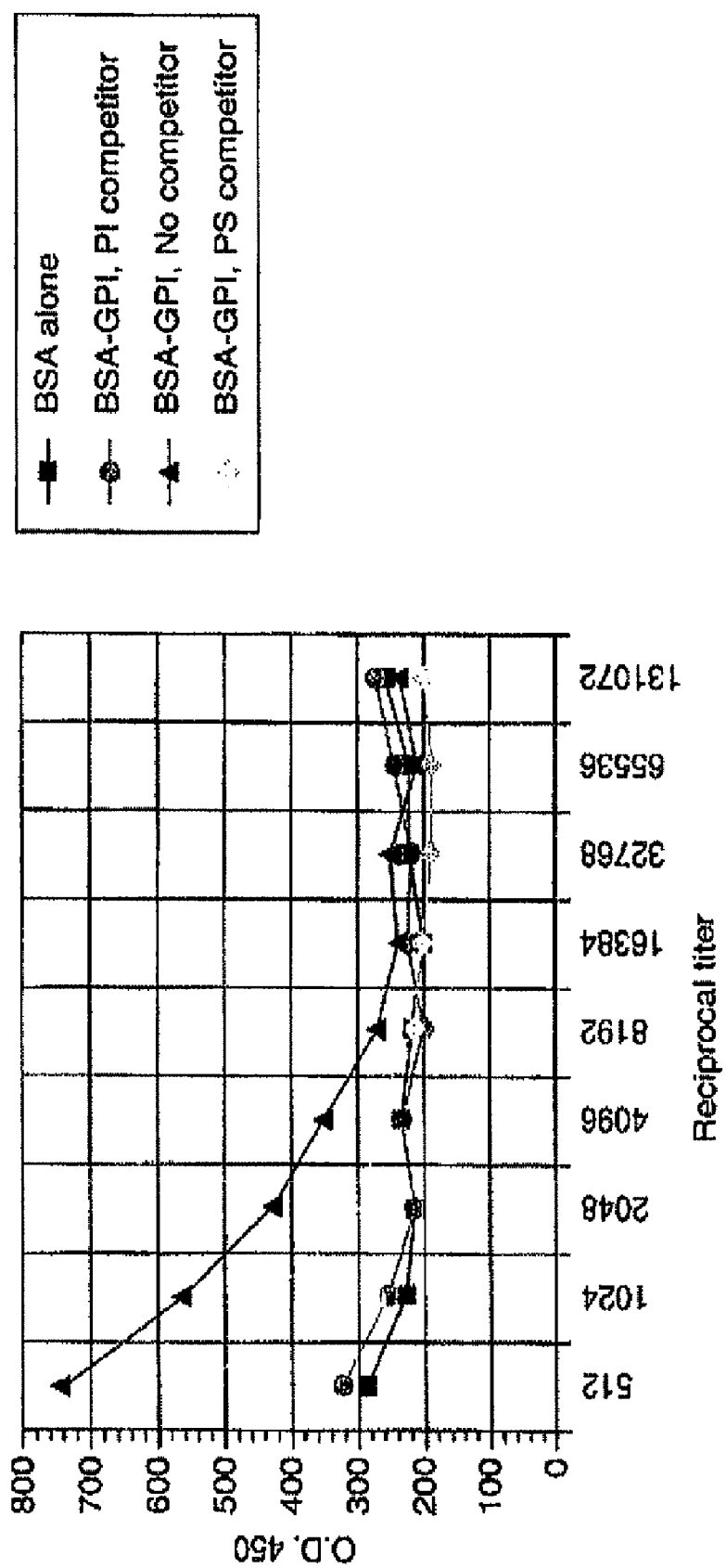
FIG. 1 is a graphical representation of the epitope specificity of anti-GPI antibodies determined by competition ELISA. Sera from mice immunized with free GPI were screened for reactivity to malarial GPI in the presence or absence of defined competitors (Phosphatidylinositol or phosphatidylserine).
Figure 2:
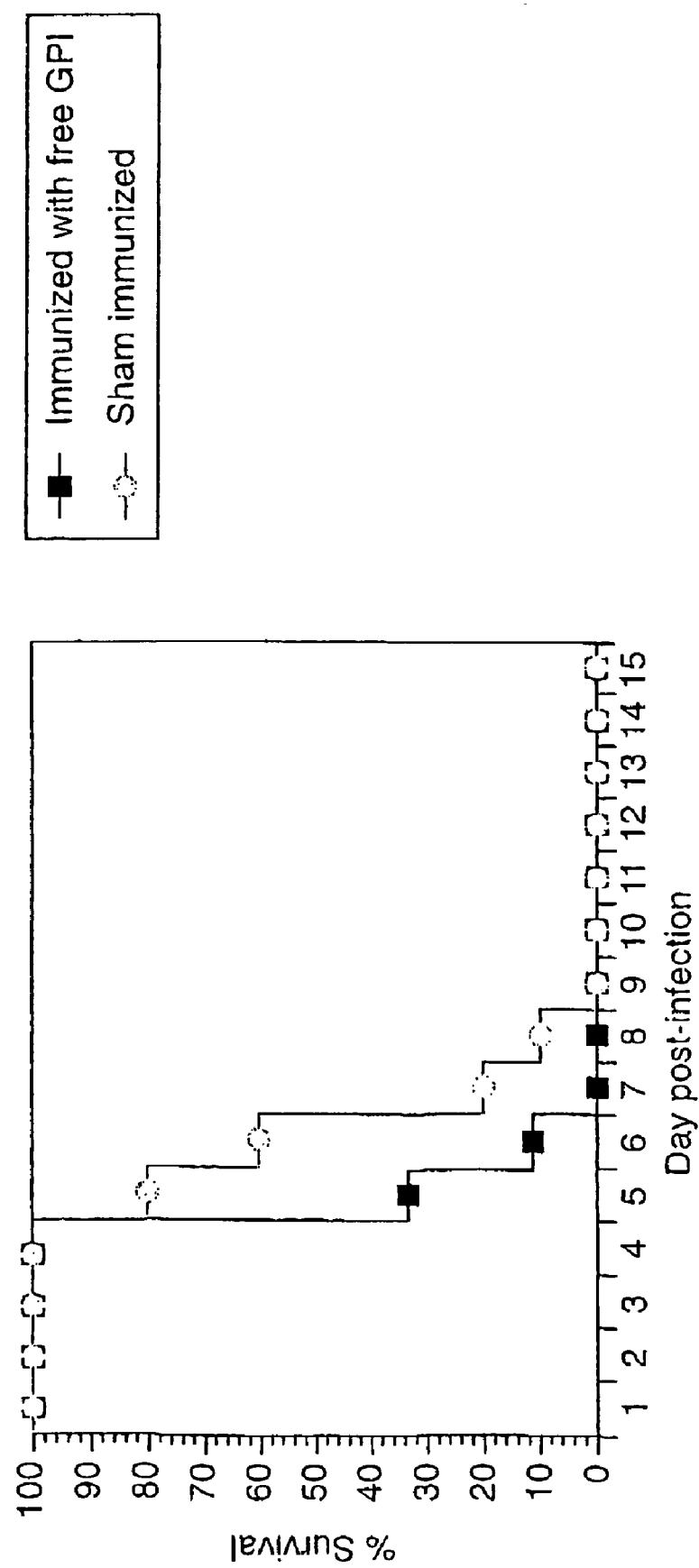
FIG. 2 is a graphical representation of the results of C57Bl/6 mice immunized with free GPI in IFA and sham-immunized mice (IFA alone) which were challenged with *P. berghei* ANKA and survival assessed over 15 days.

Mice were immunized by three successive boosts of free intact malarial GPI emulsified in Incomplete Freund's Adjuvant spaced two weeks apart. Control mice received an equal amount of IFA alone. After immunization, sera were bled and the titres of anti-GPI antibodies determined by ELISA. All animals immunized with GPI developed broadly similar levels of anti-GPI antibodies (range 1/1024-1/4096) among individual animals. The anti-GPI response was predominantly IgM, and epitope mapping studies by competition ELISA revealed that the antibody response was directed predominantly towards the lipidic (phosphatidylinositol, PI) domain of the molecule, with some cross-reactivity to other phospholipid determinants (FIG. 1). Two weeks after the final boost mice were challenged with P. berghei ANKA. Parasitaemia, the development of neurological complications, and mortality were recorded daily. No difference in parasitaemia was observed. In the control group, 100% of animal manifested between day 5 and 9 an aggressive cerebral syndrome with neurological signs proceeding to rapid death with 12 hours. In animals immunized with intact free GPI, however, deaths occurred at a noticeable faster rate (FIG. 2).

Figure 3:
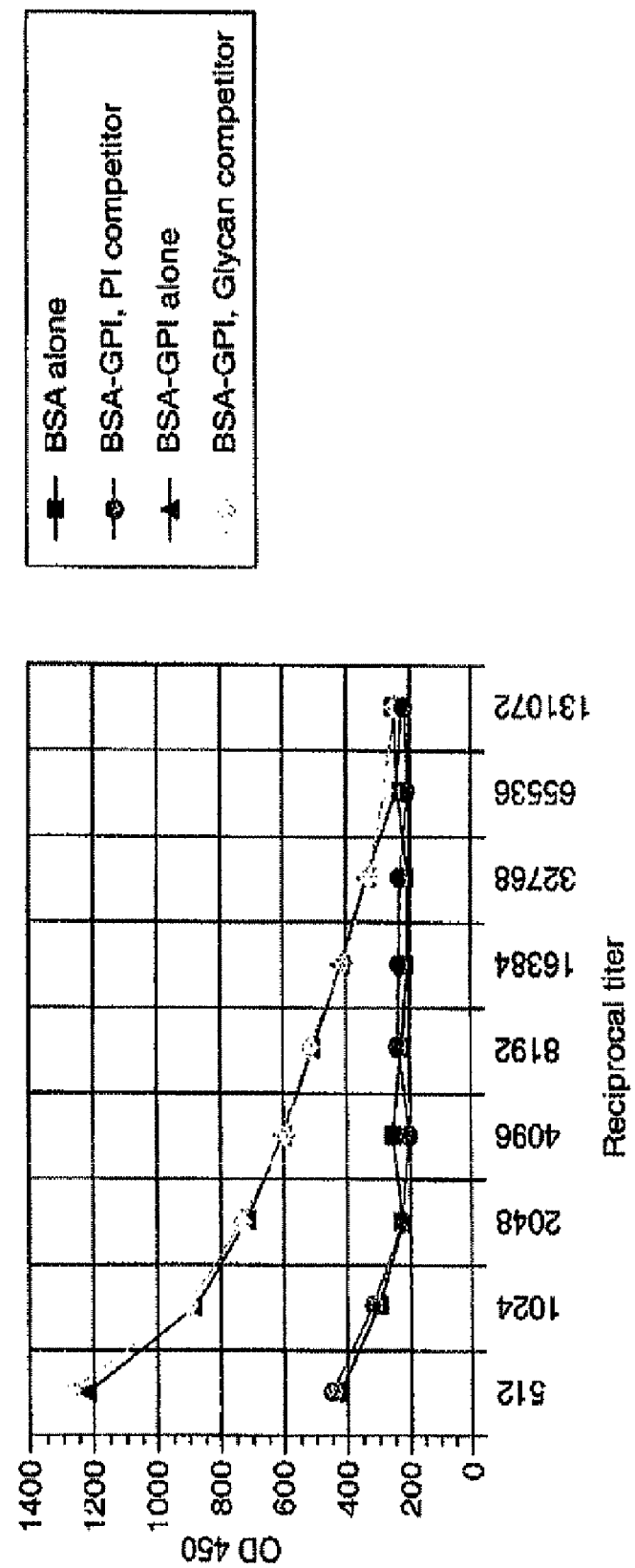
FIG. 3 is a graphical representation of the epitope mapping of anti-lipid monoclonal antibodies. Monoclonal antibody 1C7 to GPI derived from mice immunized with free GPI were screened by competition ELISA for reactivity with GPI in the presence or absence of PI and GPI glycan competitors.
Figure 4:
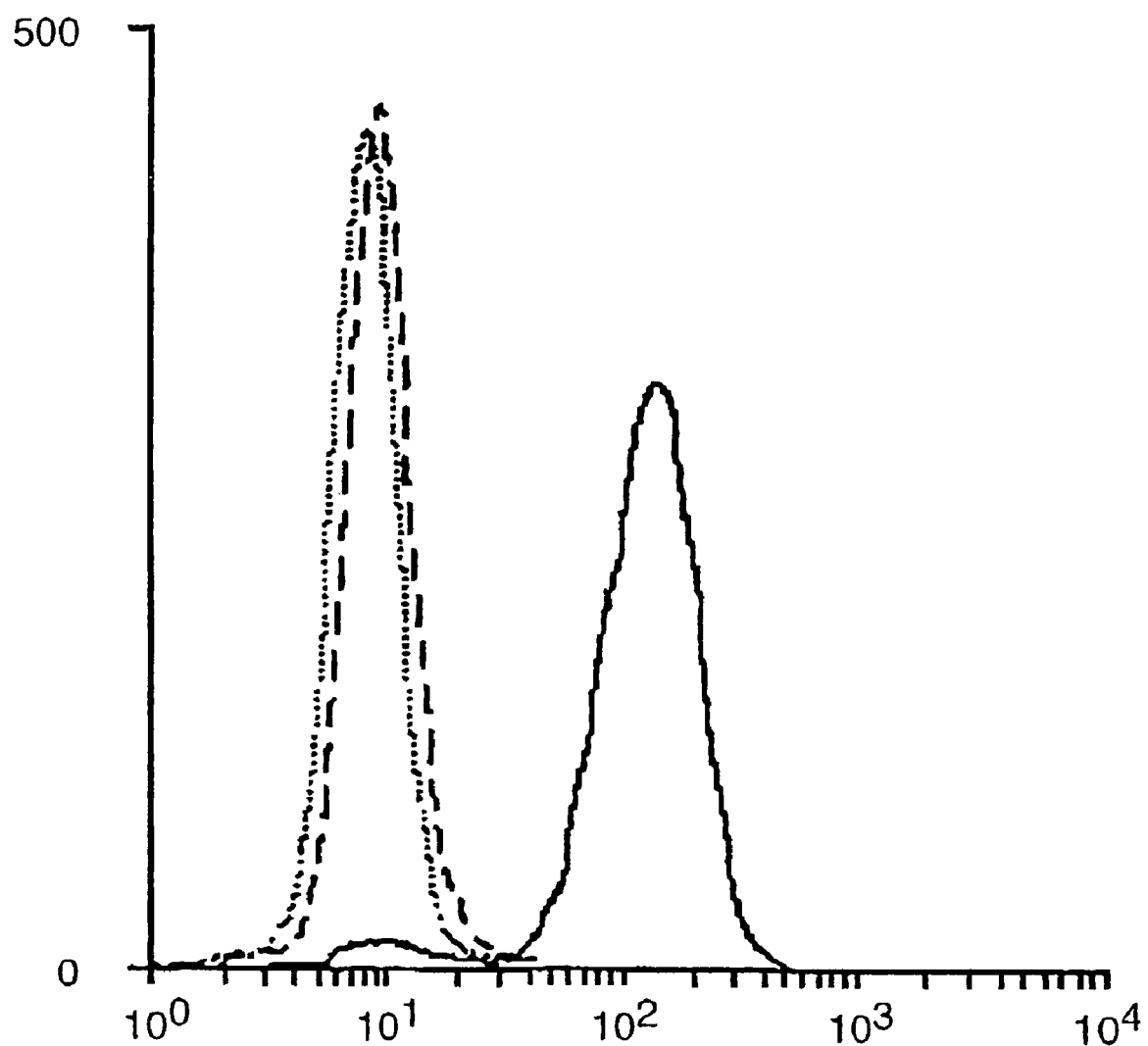
FIG. 4 is a graphical representation of monoclonal antibody 1C7, to malarial GP lipid domains, recognition of mammalian GPIs at the cell surface as determined by FACS analysis. Solid line, binding of 1C7 to macrophages; dotted line, no antibody; dashed line, binding of 1C7 following PI-PLC treatment of macrophages.
Figure 5:
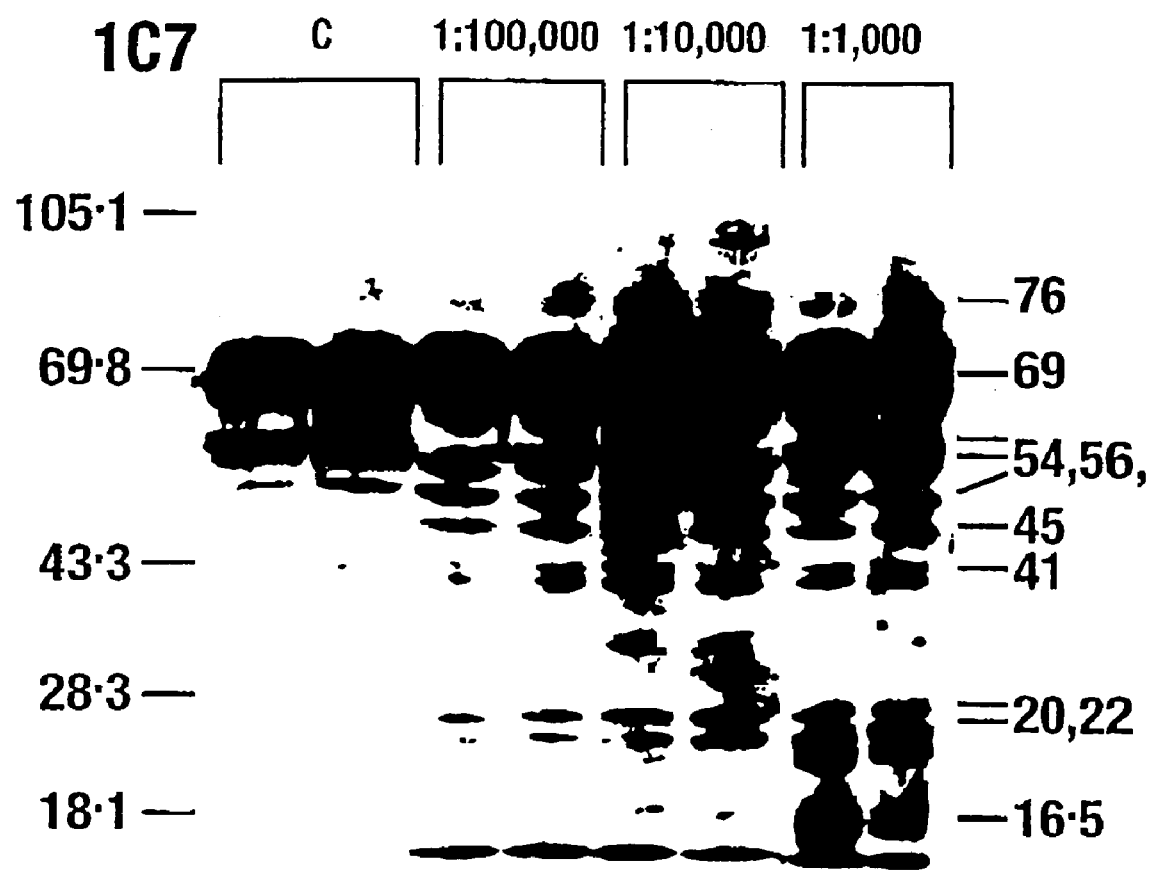
FIG. 5 is a photographic representation of monoclonal 1C7, to lipid domain of the GPI, induction of rapid onset tyrosylphosphorylation in host cells.
Figure 6:
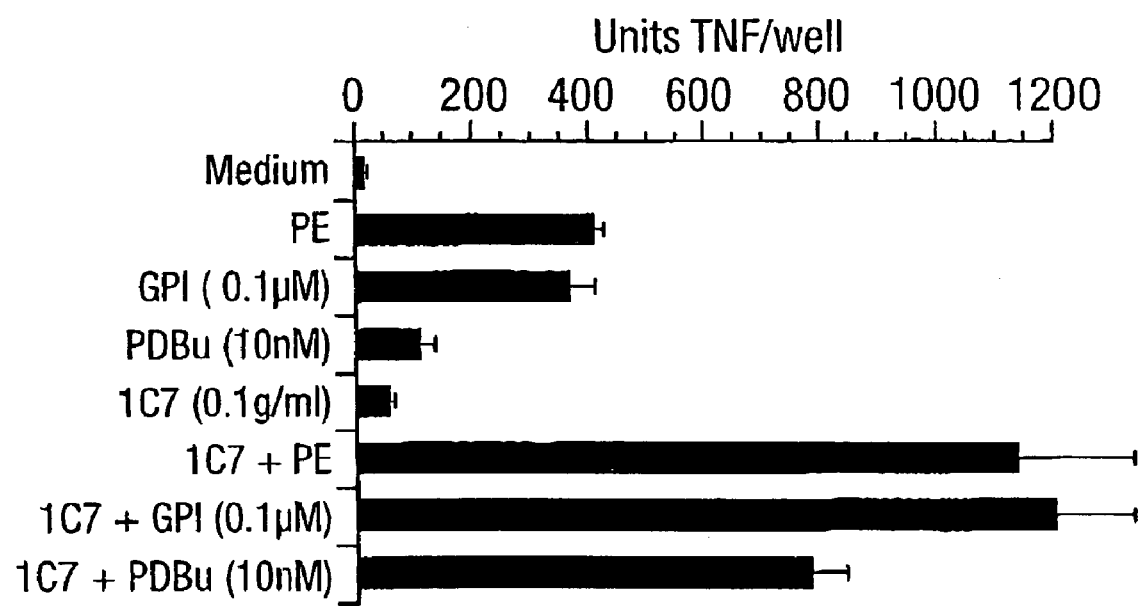
FIG. 6 is a graphical representation of monoclonal 1C7 synergize with GPI, phorbol esters and parasite extracts in the induction of TNF output from murine C3H/HeJ macrophages.
Figure 7:
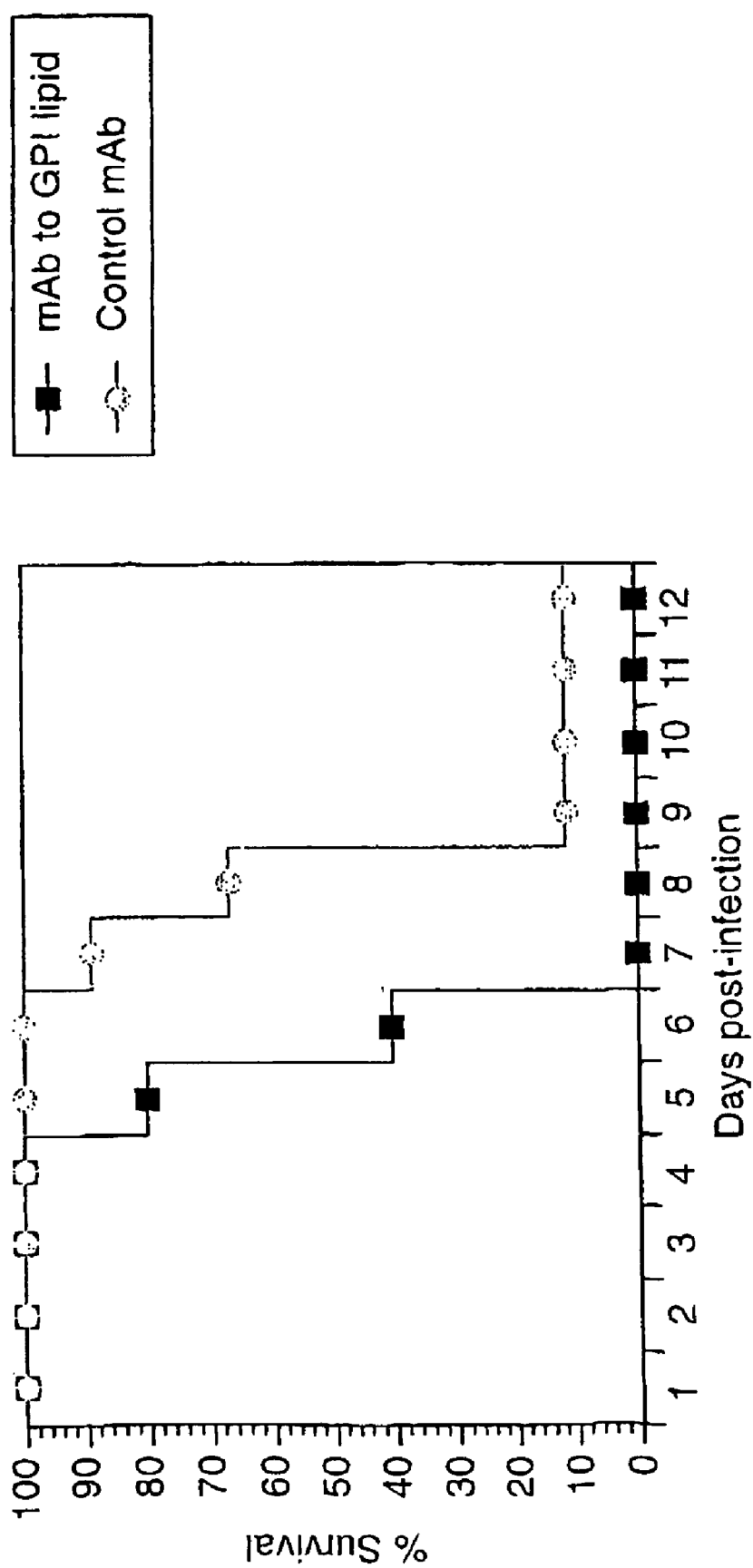
FIG. 7 is a graphical representation of monoclonal 1C7 exacerbation of the *P. berghei* ANKA cerebral malaria syndrome in C57Bl/6 mice.

The increased death rate in animals immunized with free GPI and subsequently challenged with malaria may result from unanticipated autoreactivity of anti-GPI antibodies. A panel of IgM monoclonal antibodies was derived from mice immunized with free GPIs. mAbs selected at random from this panel were shown by PI-specific ELISA to be reactive with PI domain of the molecule (FIG. 3), as was expected given the established serological specificity of the polyclonal sera of the donor immunized mice (FIG. 1). In addition, these mAbs and the polyclonal antisera of GPI-immunized mice were shown by FACS analysis to react with host GPI molecules expressed at the cell surface. Although surprising, the recognition of GPI-associated lipidic determinants at the cells surface is not without precedence (Xia, M.-Q., Hale, G., Lifely, M. R., Ferguson, M. A. J., Campbell, D., Packman, L., and Waldmann, H. (1993) Biochemical Journal 293:633-640). Pre-treatment of host cells with phosphatidylinositol-specific phospholipase C resulted in loss of binding of these mAbs, demonstrating formally that a lipidic moiety of GPI molecules is exposed at the cell surface and is accessible for binding by autoreactive antibodies generated in response to exposure to free malarial GPI (FIG. 4). The binding was also shown to cause massive rapid onset intracellular tyrosine phosphorylation (FIG. 5), a well-known and predictable consequence of cross-linking host GPIs at the cell surface (Shenoy-Scaria, A. M., Kwong, J., Fujita, T., Olszowy, M. S., Shaw, A. S., and Lublin, D. M. (1992) Journal of Immunology 149:3535-3541 and Stefanova, I., Corcoran, M. L., Horak, E. M., Wahl, L. M., Bolen, J. B., and Horak, I. D. (1993) Journal of Biological Chemistry 268:20725-20728). Following binding of these antibodies to macrophages, the cells responded more vigorously to stimulation with GPI, phorbol esters or malaria parasite extracts (FIG. 6). Upon passive transfer into mice, these mAbs were sufficient to cause an increased rate of death as compared with control IgM mAbs (FIG. 7).

Thus to summarize: (i) immunization of mice with the free P. falciparum GPI generates IgM reacting predominantly with the PI domain of the GPI; (ii) this immunization appears to exacerbate the P. berghei cerebral malaria syndrome; (iii) exacerbated pathogenicity as detected by increased death rate was also observed upon passive transfer of IgM monoclonals with the same reactivity; (iv) the mAbs were shown to cross-react with host GPIs by FACS analysis, thereby causing massive intracellular tyrosylphosphorylation and sensitization of macrophages resulting in increased TNF output in response to addition agonists. Therefore it is proposed that a novel mechanism exists by which the acquisition of certain autoreactive immunological specificities results in increased physiological sensitization to malarial toxins.

Example 17

Immunization of Mice with the GPI Glycan Conjugated to KLH

Figure 8:
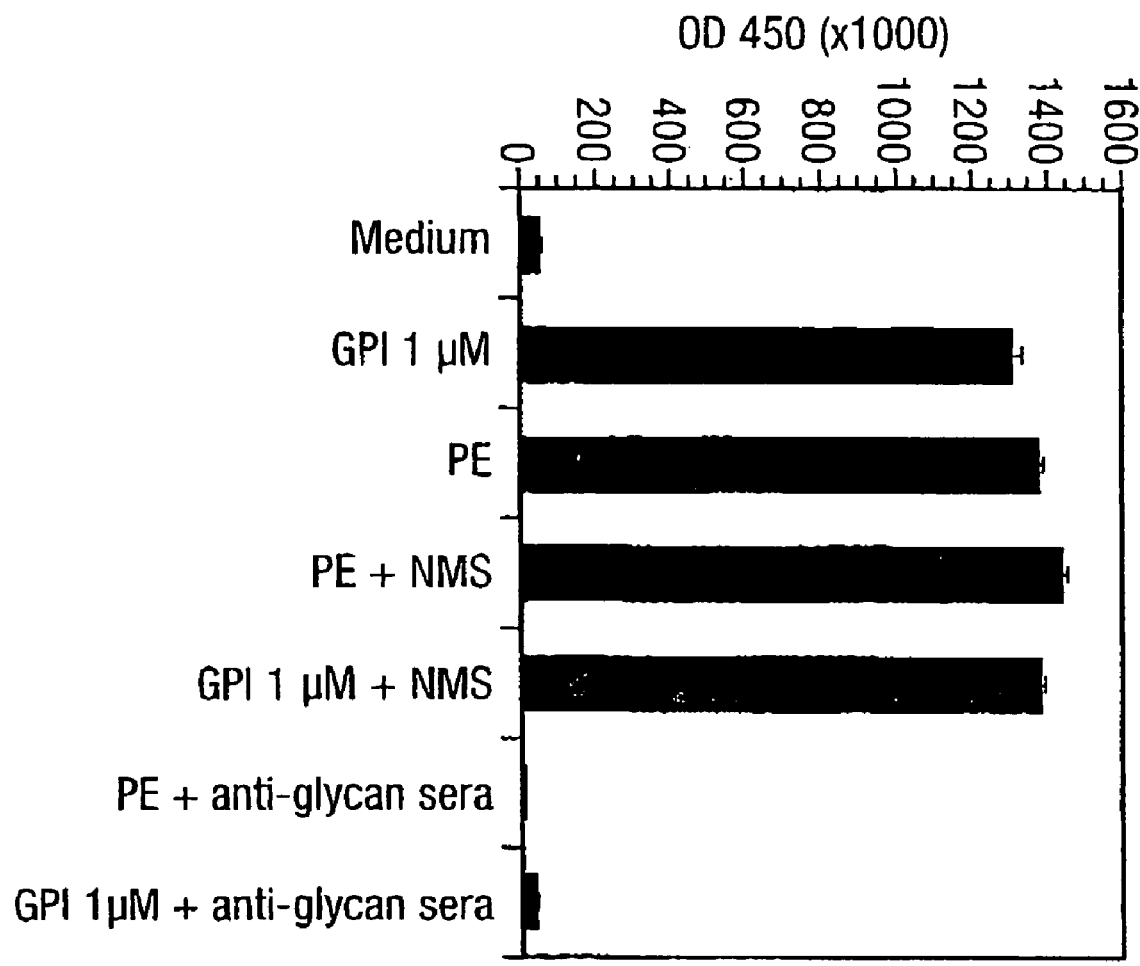
FIG. 8 is a graphical representation of polyclonal antisera from mice immunized with the purified *P. falciparum* GPI glycan covalently conjugated to a protein carrier inhibiting TNF output from macrophages in response to GPI or total parasite extracts. Values show absorbance at 450 mM by anti-TNF ELISA (Pharmingen) and are proportional to mass TNF.

Previous publications dealing with the prospect of anti-disease vaccines against malaria have proposed immunizing against a phospholipid domain within the putative toxin (Bate, C. A. W., Taverne, J., and Playfair, J. H. L. (1992c) Infection and Immunity 60:1894-1901, Bate, C. A., Taverne, J., Roman, E., Moreno, C., and Playfair, J. H. L. (1992a) Immunology 75:129-135, Bate, C. A. W., Taverne, J., Bootsma, H. J., Mason, R. C. S. H., Skalko, N., Gregoriadis, G., and Playfair, J. H. L. (1992b) Immunology 76:35-41, Bate et al (1993) supra, Jakobsen, P. H., Morris-Jones, S. D., Hviid, L., Theander, T. G., Hoier-Madsen, M., Bayoumni, R., and Greenwood, B. M. (1993b) Immunology 79:653-657, Bate, C. A. W. and Kwiatkowski, D. (1994) Infection and Immunity 62:5261-5266 and Playfair, J. H. L. (1994) Immunology Letters 43:83-86). The present data indicate strongly that this may be deleterious and should be avoided. It was sought to develop a novel approach, namely to detoxify and deacylate the GPI and to determine whether immunization against the glycan domain of the molecule would exacerbate disease or be sufficient to protect mice against malarial pathology. Mice (n=7) were immunized by three successive boosts of 50 µg KLH-glycan emulsified in Incomplete Freund's Adjuvant spaced two weeks apart. Two separate control groups (n=8 each) comprised animals receiving an equal amount of sham conjugated KLH in IFA, or those left untreated. After immunization, sera were bled and the titres of anti-GPI antibodies determined by ELISA. All animals immunized with KLH-glycan developed detectable anti-GPI glycan IgG antibodies, although there were differences in end-titre (range 1/128-1/4096) among individual animals. The sera from vaccine recipients (but not sham-KLH controls) were able to inhibit TNF output from macrophages stimulated with crude *P. falciparum* extracts, providing convincing proof-of-principle for the neutralization of pathogenicity (FIG. 8). In contrast to the host-reactive antibodies to the GPI lipid domain, pre-exposure of macrophages to these sera did not result in increased TNF output in response to additional agonists. With these sera it was not possible to detect significant cross-reactivity with host GPIs at the cell surface as judged by FACS analysis of antibody binding to host cells.

Figure 9:
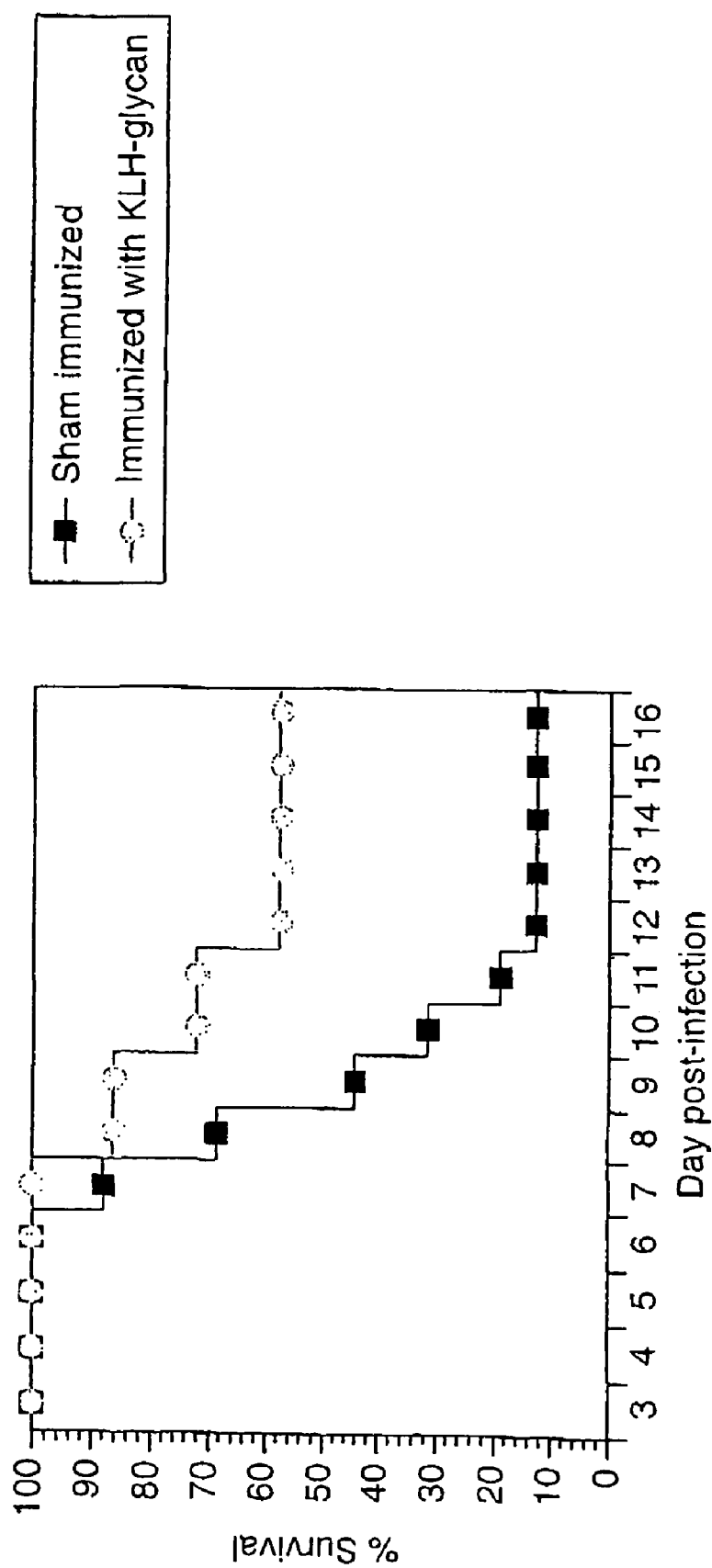
FIG. 9 is a graphical representation of immunization of C57Bl/6 mice with the purified *P. falciparum* GPI glycan covalently coupled to KLH providing a significant level of protection against the cerebral malaria syndrome induced by *P. berghei* ANKA.

The *P. berghei* ANKA murine cerebral malaria model has many features in common with the human cerebral malaria syndrome. It is a TNF-α and interferon-γ (IFN-γ) dependent encephalitis associated with upregulation of ICAM-1 on the cerebral microvascular endothelium, an increase in both parasite and macrophage/neutrophil adherence to these target cells, and attendant neurological complications. Unlike human cerebral malaria, there is a breakdown of the blood-brain barrier in the terminal stages of the murine syndrome. However, in the proximal stages the murine disease reflects more accurately the inflammatory cascade leading to cerebral involvement in humans. To determine whether anti-GPI immunization prevents cerebral pathogenesis in vivo, mice were immunized with *P. falciparum* IPG conjugated to KLH. Two weeks after the final boost mice were challenged with *P. berghei* ANKA. Parasitaemia, the development of neurological complications, and mortality were recorded daily. No difference in parasitaemia was observed among groups. In both control groups, 87.5% of animal manifested between day 7 and 12 an aggressive cerebral syndrome with neurological signs proceeding to rapid death with 12 hours, and 12.5% did not develop the syndrome. As there were no significant differences between sham-immunized and untreated groups, the data from these two control groups are pooled (FIG. 9). In recipients of KLH-glycan, one animal (14.2%) died with similar kinetics, two animals (28.5%) developed the cerebral syndrome with substantially delayed kinetics (on days 10 and 11, and showing prolonged course of syndrome before succumbing), and four animals (57.2%) were completely protected, failing to develop the cerebral syndrome at any stage (FIG. 9). Thus immunization of mice with the *P. falciparum* GPI glycan covalently linked to a carrier protein affords substantial protection against the *P. berghei* cerebral malaria syndrome.

Figure 10:
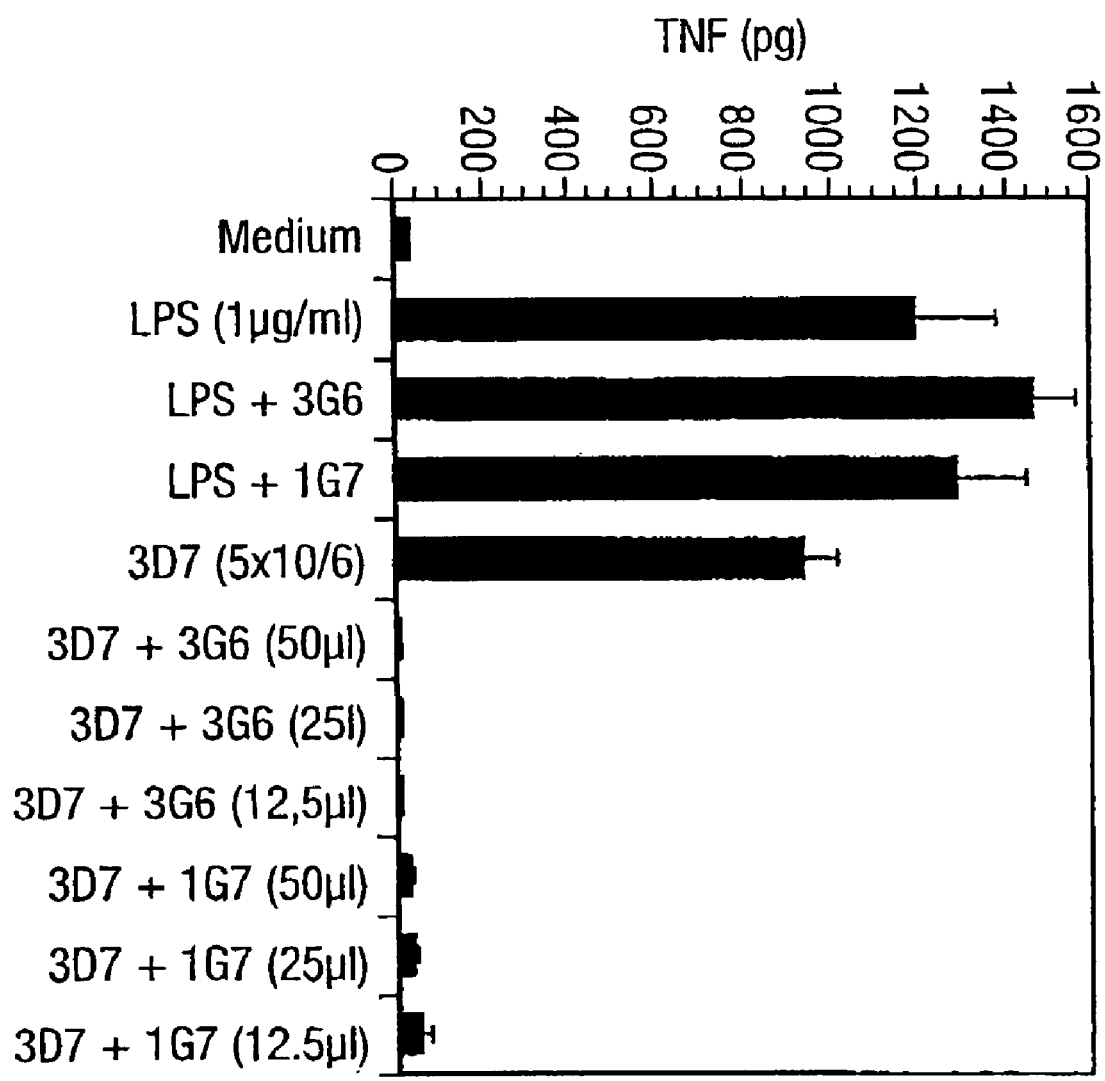
FIG. 10 is a graphical representation of GPI being the dominant TNF-inducing toxin of *P. falciparum*. Monoclonal antibodies 1G7 and 3G6 specific for the GPI glycan derived from OVA-TCR mice immunized with OVA-glycan inhibiting TNF output from macrophages in response to total parasite extracts.
Figure 11:
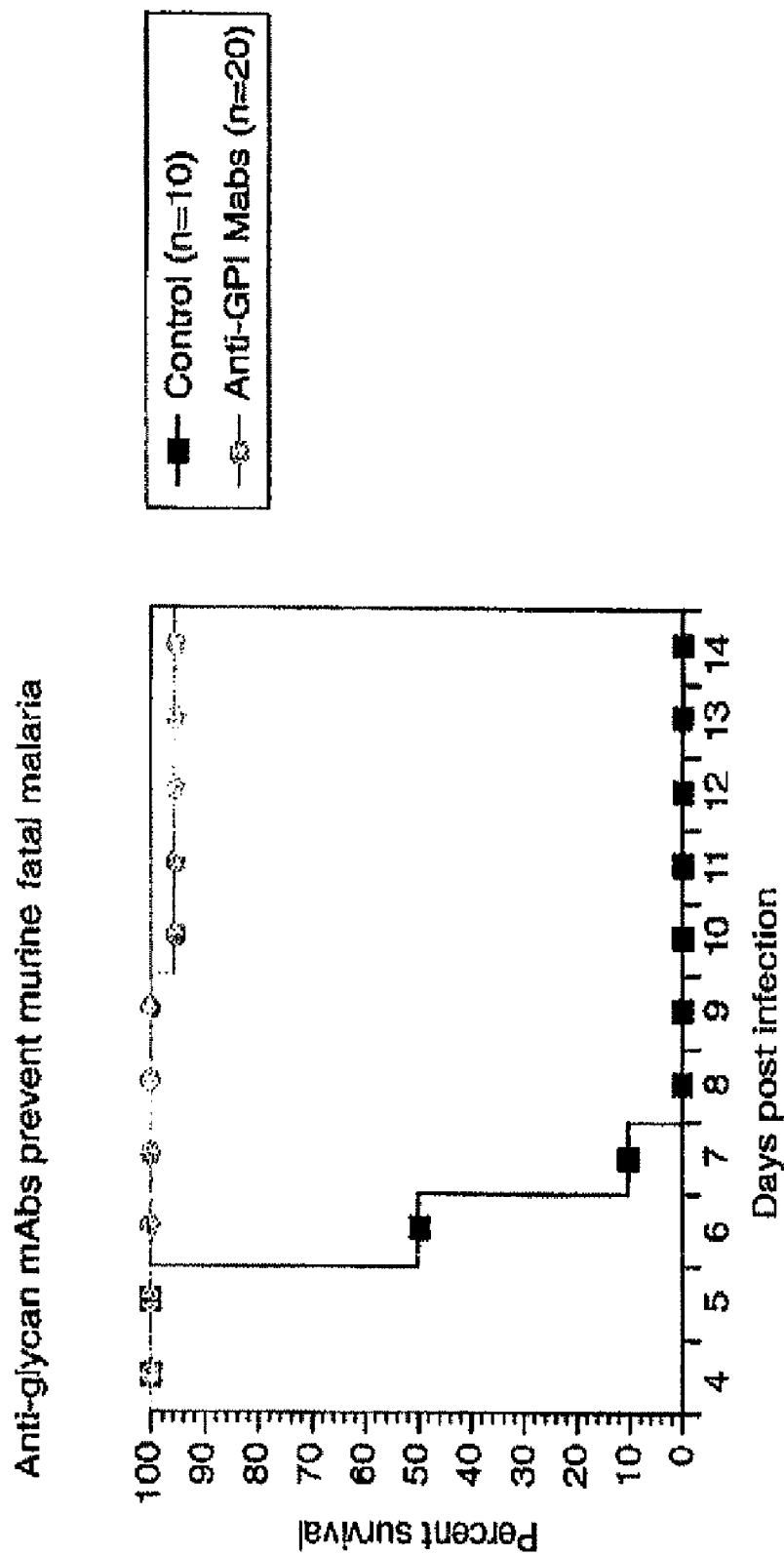
FIG. 11 is a graphical representation of monoclonal antibodies to the *P. falciparum* GPI inositolglycan, upon passive transfer, substantially protecting mice against cerebral malaria.

A panel of monoclonal antibodies was made from mice immunized with purified GPI glycan conjugated to OVA (OVA-glycan). The hybridoma fusion products were initially screened for binding to BSA-glycan as compared to BSA alone. Over 80 glycan-reactive IgG monoclonal antibodies were detected. Of these, many were reactive with parasites but not host erythrocytes as judged by the Indirect Fluorescent Antibody Test. Purified monoclonal antibodies 1G7 and 3G6 were sufficient to block the induction of TNF by 100% when added at low concentration to total crude parasite extracts (FIG. 10). To determine whether anti-GPI antibodies alone are sufficient to prevent severe malarial pathology, mice were infected with $10^6$ *P. berghei* ANKA i.p. On day 4 they were divided at random into 10 controls receiving an irrelevant IgG and groups of 5 receiving mAbs 1D12, 2C4, 3G5 and 4C3 raised against the *P. falciparum* GPI inositolphosphoglycan. All mice received 100 µg antibody/day i.p. for 7 days. Mice were monitored for parasitaemia daily and clinical signs every 6 hours. 100% of controls died of the cerebral malaria syndrome between days 6 and 8 post-infection. Throughout this period, no animals receiving either of the 4 anti-GPI monoclonal antibodies showed signs of illness, despite being equally parasitized as controls. On day 10 one of the 5 animals receiving monoclonal 3G5 died. Other than this individual, no others showed cerebral signs and none died (FIG. 11). Thus 19/20 (95%) of the 20 animals receiving anti-GPI mAbs survived, vs. zero survival in controls (n=30 total). Parasitaemias were identical in test and control groups throughout the experiment. For visual clarity, the figure shows the 4 treatment groups in aggregate. In addition, 5 mice received antibodies alone without parasite challenge. There were no detectable acute or toxic reactions in these mice receiving antibodies alone.

Figure 12:
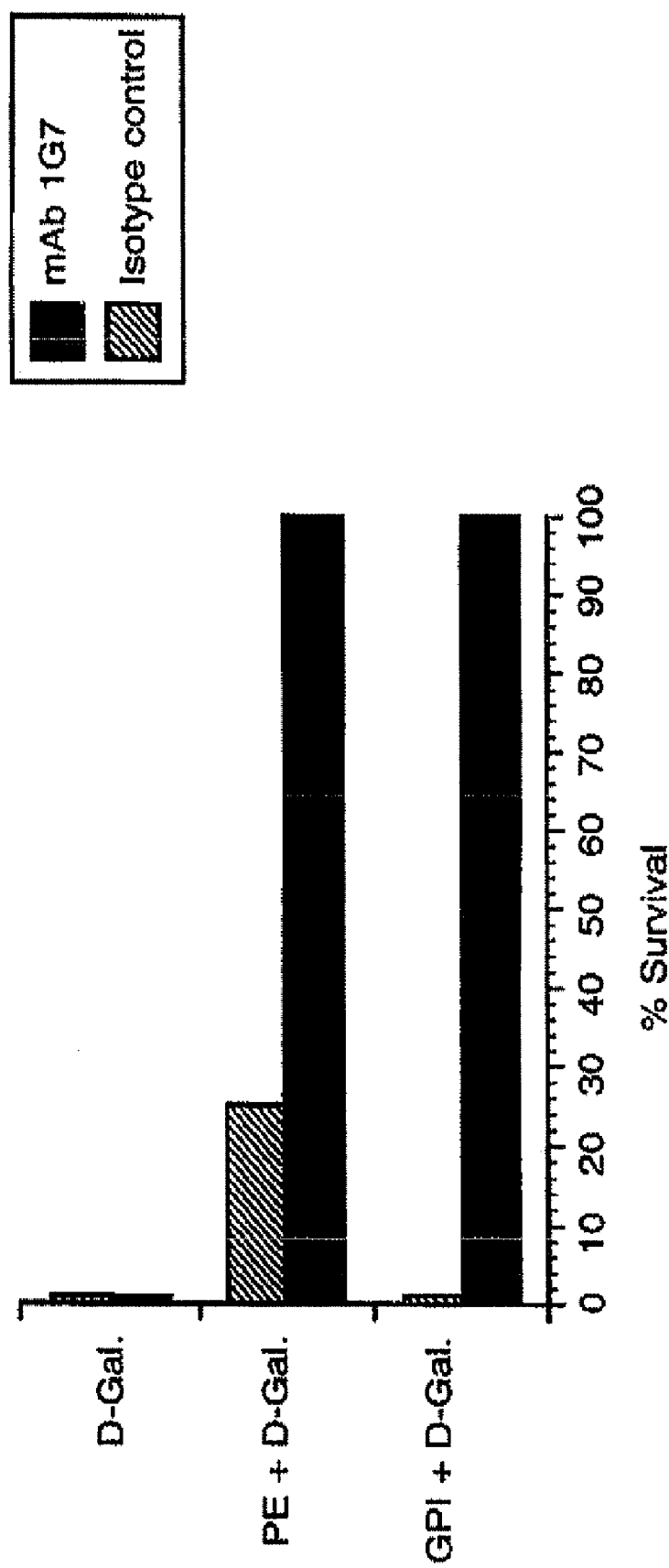
FIG. 12 is a graphical representation of monoclonal antibodies to the *P. falciparum* inositolglycan, upon passive transfer, protecting mice against parasite-induced lethal toxic shock.

In addition a standard murine model of TNF-driven lethality was used to determine whether GPI mediates parasite-induced acute toxic shock. This model manifests disseminated intravascular coagulation, peripheral vascular failure and shock, and thus has clinical features in common with the human "algid malaria" syndrome. LPS-non-responsive C3H/HeJ and C57B16 mice were primed with 20 mg D-galactosamine followed after 1 hour by purified GPI, PE or PBS alone. Mice receiving D-galactosamine followed by vehicle alone showed 100% survival. Both PE and purified GPI induced lethal shock in 100% of D-galactosamine-primed C3H/HeJ and C57B16 recipients. mAbs to the GPI glycan substantially prevented TNF-driven lethality in vivo (FIG. 12).

Example 18

Synthetic GPI as a Candidate Anti-Toxic Vaccine Against Malaria

Methods
Protein/Glycan Conjugation

Synthetic GPI glycan 1 was reacted with 10-fold molar excess of Traut's reagent (2-iminothiolane) in 60 mM triethanolamine, 7 mM potassium phosphate, 100 mM NaCl, 1 mM EDTA, pH 8.0 in the cold for 90 minutes under nitrogen, to introduce a sulfhydryl onto the free primary amine (ethanolamine). The sample was desalted by Giogel P4 filtration in coupling buffer at 4° C., and the sample added to maleimide-activated KLH or OVA (Pierce) overnight. After exhaustive dialysis against water, conjugation efficiency was estimated by Gas Chromatography/Mass Spectroscopy. Samples were hydrolysed in 6N HCl and the trimethylsilyl derivatives quantified for myo-inositol content by selective ion monitoring, using scyllo-inositol as internal standard. For the generation of sham-conjugated carrier proteins, maleimide-activated KLH or OVA (Pierce) were subjected to identical procedures except cysteine was substituted for sulfhydryl-modified glycan.

Infections

All experiments were in accordance with local Animal Ethics Committee regulations. Young adult C57BL6 mice from Jackson Laboratories were pre-bled and inoculated with 6.5 µg KLH-glycan (0.176 µg glycan, n=16) or KLH-cysteine (sham-immunized, n=24) emulsified in Freund's Complete Adjuvant, and boosted with equal amounts of immunogen in Incomplete Freund's Adjuvant at 2 weekly intervals. After two boosts they were rested and injected i.p with $1\times10^6$ P. berghei ANKA-infected erythrocytes. Naïve mice (n=12) served as unimmunized controls. Parasitemias were assessed from Giemsa-stained thin films. Mortality was checked twice daily. Mice were judged as developing cerebral malaria if displaying neurological signs such as loss of reflex or ataxia, and dying between days 5 to 12 post-infection with relatively low parasitemia levels (below 15%). Differences in survival curves of P. berghei infected mice across this time-period were assessed by Cox-Mantel logrank transformation on Kaplan-Meier plots. Deaths from day 14 onwards with high parasitaemia (>60%) and low rates of cerebral vascular occlusion were ascribed to hyperparasitaema/haemolysis, and all animals failing to develop cerebral malaria eventually succumbed to this syndrome.

Pathology

For histological analysis of cerebral pathology brains were taken into 10% neutral-buffered formalin, sectioned (5µ) and stained with Haemotoxylin/Eosin. In other experiments, groups of 6 naïve, sham-immunized and KLH-glycan immunized mice were challenged as above. All mice were sacrificed at day 6, along with age/sex matched uninfected controls, their serum collected for determination of pH, and lungs removed. The wet weight was determined immediately after removal of the organ, and the dry weight after overnight incubation at 80° C. (25). Brains were taken for histological examination as above.

TNF Output

Mycoplasma-free P. falciparum schizonts (3D7 strain) were prepared by gelatin flotation followed either by extraction with sample buffer (for SDS-PAGE and Western blots) or by saponin lysis and three washes in isotonic buffer. Parasites were taken up by sonication in complete medium and aliquots of $5\times10^6$ cell equivalents in 100 µl volumes pre-incubated for 1 hour with the indicated concentration of test or control sera, followed by addition to $4\times10^5$ target RAW264.7 cells for 16 hours in a 96-well plate. Levels of TNFα in culture supernatants were determined by capture ELISA according to manufacturer's protocol (Pharmingen, San Diego, USA) and quantified by interpolation against a recombinant protein standard curves.

Immunofluoresence

Thin films of mature P. falciparum cultures at 10% parasitaemia were fixed in acetone at −20° C. and exposed to test and control antisera (1/80) followed after washing in PBS by 1/200 dilution of fluorochrome-conjugated goat anti-mouse IgG (γ-chain specific). Slides were photographed under appropriate illumination.

Statistics

Statistical comparison between test and control groups was by Student's t-test except for Kaplan-Meier survival plots, tested by Cox-Mantel logrank transformation.

Results

Figure 13:
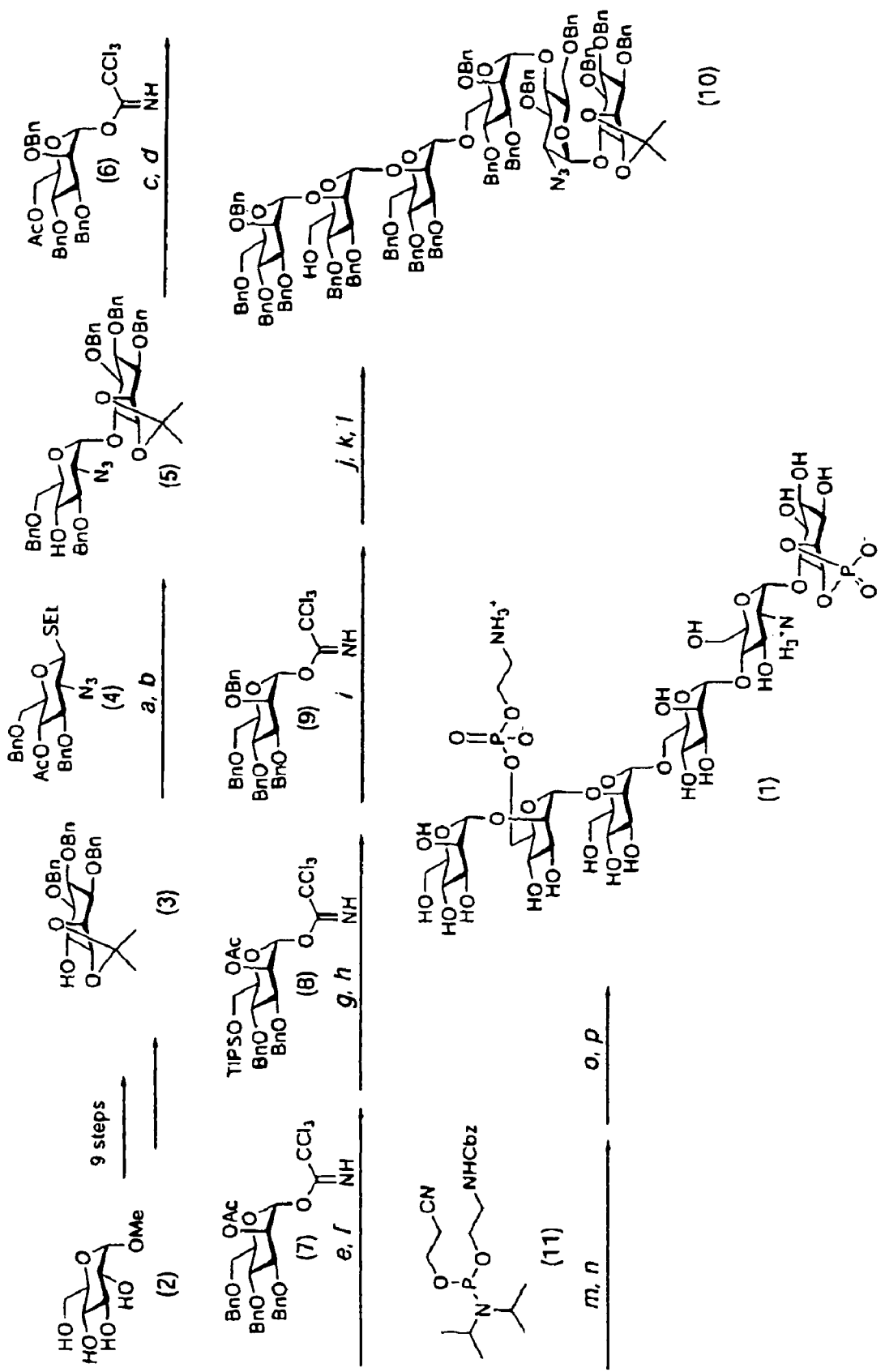
FIG. 13 is a schematic representation of the synthesis of glycan. 1. Reagents: a. 4, AgOTf, NIS, $CH_2Cl_2/Et_2O$ (38% a); b. NaOMe, $CH_2Cl_2$/MeOH (83%); c. 6, TMSOTf, $CH_2Cl_2$ (75%); d. NaOMe, $CH_2Cl_2$/MeOH (71%); e. 7, TMSOTf, $CH_2Cl_2$ (92%); f. NaOMe (69%); g. 8, TBSOTf, $CH_2Cl_2$ (98%); h. NaOMe (83%); i 9, TMSOTF, $CH_2Cl_2$ (84%); j. $(CH_2OH)_2$, CSA, $CH_3CN$ (81%); k. $Cl_2P(O)OMe$, Pyr. (88%); l, TBAF, THF (61%); m, 11, tetrazole, $CH_3CN$; n. t-BuOOH, $CH_3CN$ (84%, 2 steps); o. DBU, $CH_2Cl_2$; P. Na, $NH_3$, THF (75%, 2 steps). (AgOTf, silver trifluoromethanesulfonate; NIS, N-iodosuccinimide; $CH_2Cl_2$, dichloromethane, $Et_2O$, diethyl ether; NaOMe, sodium methoxide; MeOH, methanol; TMEOTf, trimethylsilyltrifluoromethane sulfonate; TBSOTf, tert-butyldimethylsilyl trifluoromethanesulfonate; CSA, camphorsulfonic acid; $CH_3CN$, acetonitrile; Cbz, carbobenzyloxy; Pyr, pyridine; TBAF, tetrabutylammonium fluoride; THF, tetrahydrofuran; DBU, 1,8-diazabicyclo[5,4,0]undec-7-ene; Obn, O-benzyl).

P. falciparum shows uniquely low levels of N- and O-linked glycosylation (Dieckmann-Schuppert, A., Bender, S., Odenthal-Schnittler, M., Bause, E. and Schwarz, R. T. (1992) Eur. J. Biochem. 205:815-825; Dieckmann-Schuppert, A., Bause, E. and Schwarz, R. T. (1993) Eur. J. Biochem. 216:779-788), and GPI accordingly represents at least 95% of the post-translational carbohydrate modification of parasite proteins (Gowda, D. C., Gupta, P. and Davidson, E. A. (1997) J. Biol. Chem. 272:6428-6439). GPI structure is conserved across all parasite isolates examined to date (Berhe, S., Schofield, L., Schwarz, R. T. and Gerold, P. (1999) Mol. Biochem. Parasitol. 103:273-278). The bioactivity of GPIs against target host tissues requires the contribution of both lipid and carbohydrate domains, and deacylation of GPIs by enzymatic or chemical hydrolysis renders the carbohydrate moiety non-toxic (Schofield et al. (1993), supra; Tachado, S. D., and Schofield, L. (1994) Biochem. Biophys. Res. Commun. 205:984-991; Schofield et al. (1996), supra; Tachado et al. (1996), supra; Tachado et al. (1997), supra). Based on the sequence of the non-toxic P. falciparum GPI glycan (Gerold, P., Dieckmann-Schuppert, A. and Schwarz, R. T. (1994) J. Biol. Chem. 269:2597-2606), the structure $NH_2$—$CH_2$—$CH_2$—$PO_4$-(Manα1-2)6Manα1-2Manα1-6Manα1-4GlcNH$_2$α1-6myo-Insositol-1,2 cyclic phosphate was chemically synthesised (FIG. 13). Confirmation of structure was by MALDI-TOF mass spectrometry and $^{31}$P-NMR ($D_2O$). To prepare an immunogen, the synthetic GPI glycan was treated with 2-iminothiolane to introduce a sulfhydryl at the primary amine within the ethanolamine phosphate, desalted, and conjugated to maleimide-activated Ovalbumin (OVA, in molar ratio 3.2:1) or Key-Hole Limpet Haemocyanin (KLH, in molar ratio 191:1). This material was used to immunize mice.

Figure 14A:
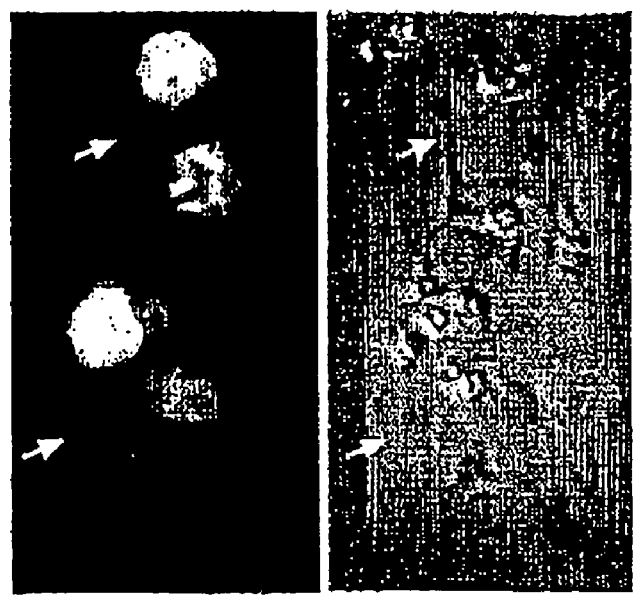
FIG. 14 is an image of antibodies raised against synthetic GPI glycan recognizing native GPI and neutralize toxin activity in vitro. a. Left panel, reactivity of anti-glycan IgG antibodies with *P. falciparum* trophozoites and schizonts and lack of reactivity to uninfected erythrocytes detected by immunofluorescence assay. Right panel, the same field under white light illumination. b. Left panel, Western blot of anti-glycan IgG antibodies (1/200) against parasite-infected (lane 1) and uninfected erythrocytes (lane 2). Right panel, comparison of reactivity against parasites by two sera from KLH-glycan-immunized mice (lanes 3,4), pre-immune sera from lane 3 donor (lane 5) and sham KLH-immunized mouse (lane 6). All sera were used at 1/400 dilution. The detection antibody was peroxidase-conjugated goat anti-mouse IgG (γ-chain specific). DF, dye front. c. Levels of TNFα in culture supernatants of RAW264.7 cells exposed to medium alone (open square), parasites alone (triangle), or parasites in the presence of various dilutions of sera from pre-immune (closed circle), sham-immunized (closed square) or glycan immunized mice (open circles).
Figure 14B:
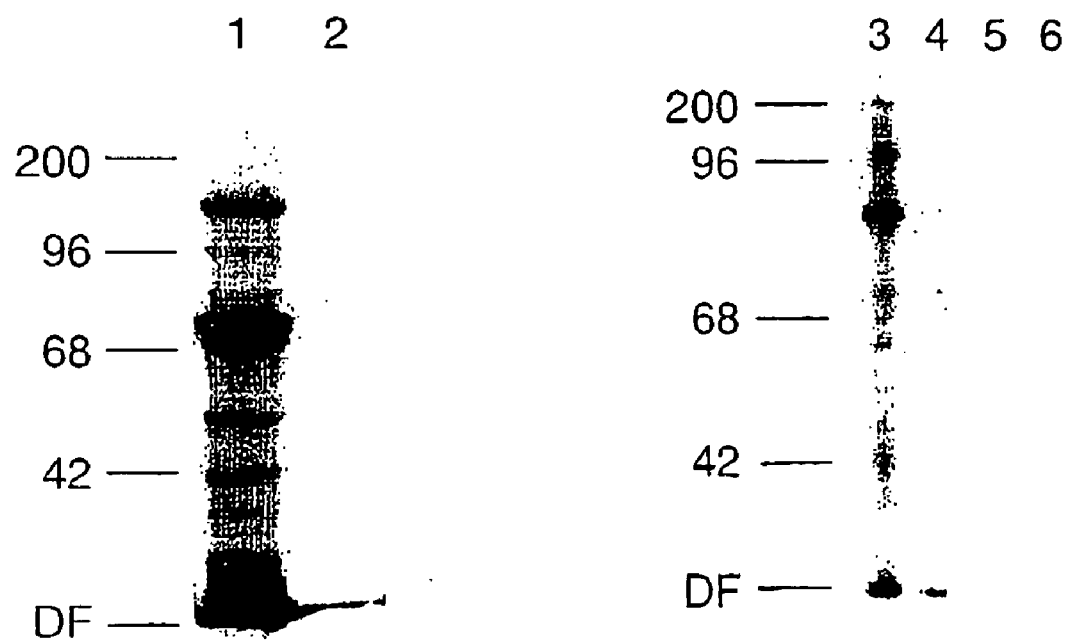

The synthetic malarial GPI glycan was immunogenic in rodents. Antibodies from KLH-glycan immunized animals gave positive IgG titres against OVA-glycan but no sham-conjugated OVA-cysteine containing identical carrier and sulfhydryl bridging groups. No reactivity to GPI glycan was detected in pre-immune sera or in animals receiving sham-conjugated KLH. More significantly, antibodies raised against synthetic P. falciparum GPI glycan bound to native GPI as judged by several methods. These IgG antibodies recognized intact trophozoites and schizonts by immunofluorescence (FIG. 14a), with a subcellular distribution suggestive of exclusion from merozoite nuclei. Pre-immune and sham-immunized sera failed to react. Anti-GPI failed to bind to uninfected erythrocytes, despite these cells expressing endogenous GPIs of host origin (FIG. 14a). However, in contrast to malaria GPI, all mammalian GPIs characterized to date show amino-sugar or phosphoethanolamine modifications to the core glycan structure (McConville et al. (1993), supra) and these epitopic differences may account for the lack of cross-reactivity. As expected, anti-GPI glycan IgG detected multiple molecular species in Western blotting against P. falciparum-infected erythrocytes but not uninfected erythrocytes (FIG. 14b), consistent with the presence in mature schizonts of multiple GPI-modified proteins such as MSP-1, MSP-2, MSP4, MSP-5 as well as their processing products. These results indicate that protein-specific features do not greatly influence the binding of anti-glycan antibodies to native GPI anchors. Structurally identical, non-protein linked free GPIs occur in molar ratio 4:1 to protein-linked forms, and a frequent observation was strong reactivity with these moieties running at the dye-front (FIG. 14b). Pre-immune and sham-immunized sera failed to react in Western blots (FIG. 14b).

Figure 14C:
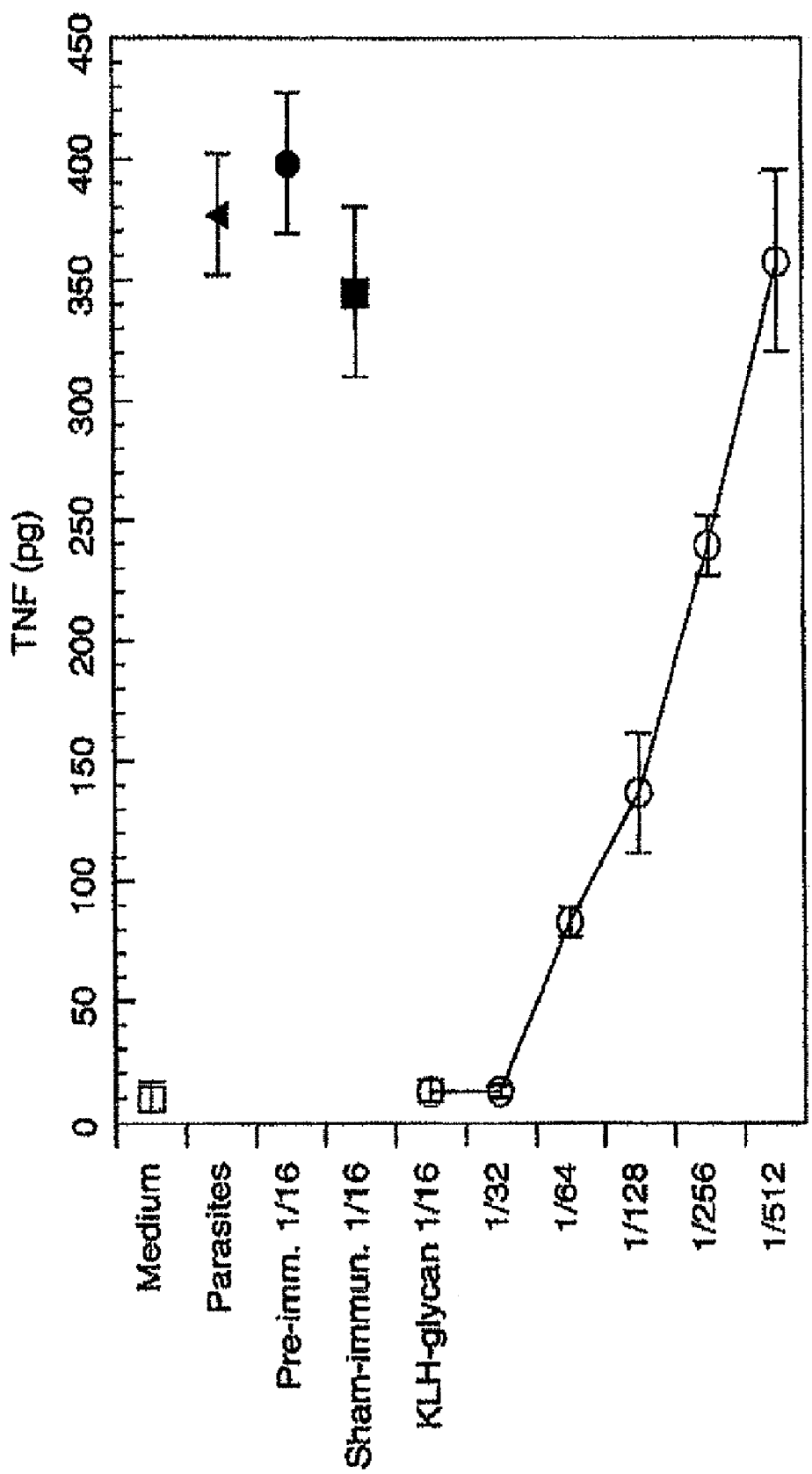

TNFα production by macrophages is widely used as a biochemical marker of malaria endotoxin activity in vitro. Purified malarial GPI is sufficient for TNF production (Schofield et al. (1993) supra; Tachado et al. (1994) supra; Schofield et al. (1996) supra; Tachado et al. (1996) supra; Tachado et al. (1997), supra), but it remains unclear whether this agent is predominantly responsible for this activity in parasites. It was sought to determine whether antibodies specific for the *P. falciparum* GPI could neutralize parasite endotoxic activity in vitro, and to quantify the contribution of GPI to the total endotoxic activity of malaria. In contrast to pre-immune sera or those drawn from sham-conjugated KLH-immunized controls, antibodies from mice immunized with KLH-glycan specifically neutralized TNFα output from macrophages induced by crude total extracts of *P. falciparum* (FIG. 14c). These antibodies have no effect on macrophage viability or production of TNFα in response to unrelated agonists such as lipopolysaccharide. Thus GPI is required for the induction by malaria parasites of host pro-inflammatory responses in vitro.

Figure 15A:
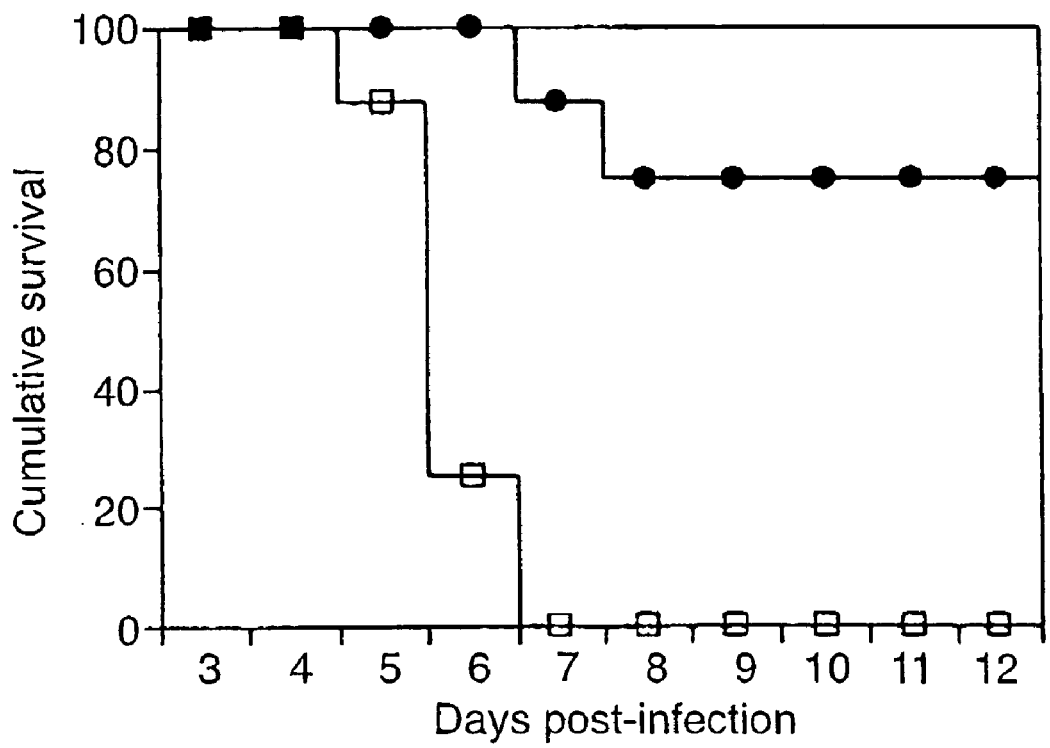
FIG. 15 is an image of immunization against the synthetic GPI glycan substantially protecting against murine cerebral malaria, pulmonary oedema and acidosis. a. Kaplan-Meier survival plots, and b. parasitaemias, to 15 days post infection, of KLH-glycan-immunized (closed circles) and sham-immunized (open squares) mice challenged with *P. berghei* ANKA.
Figure 15B:
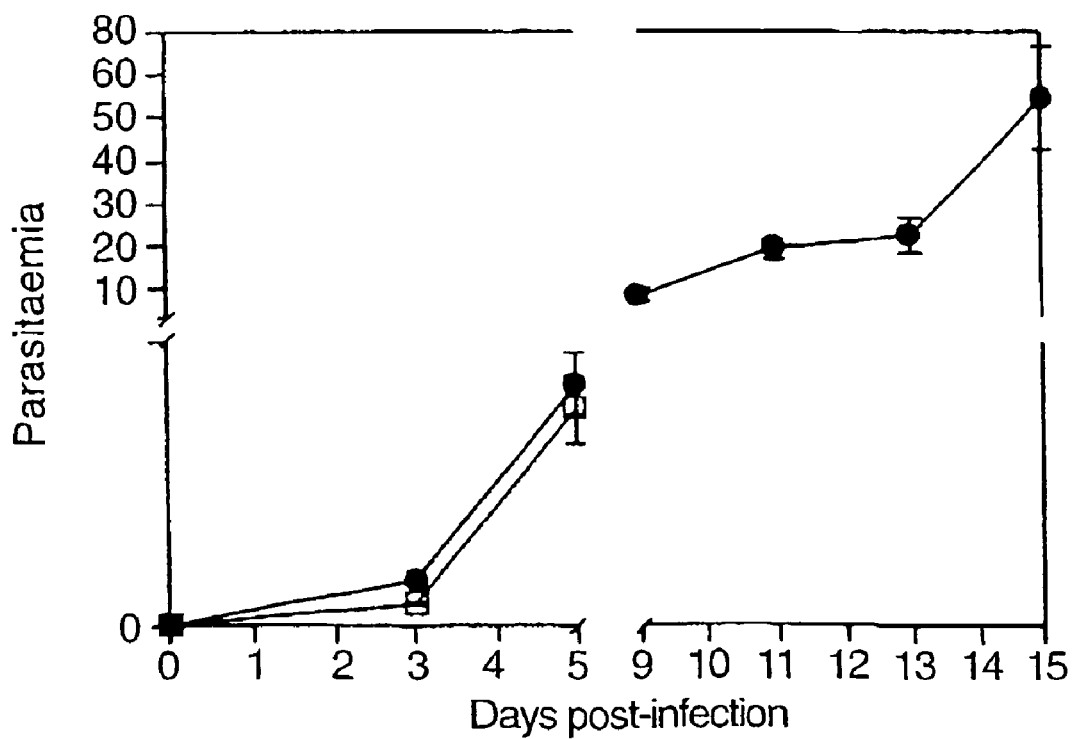
Figure 15C:
Figure 15:
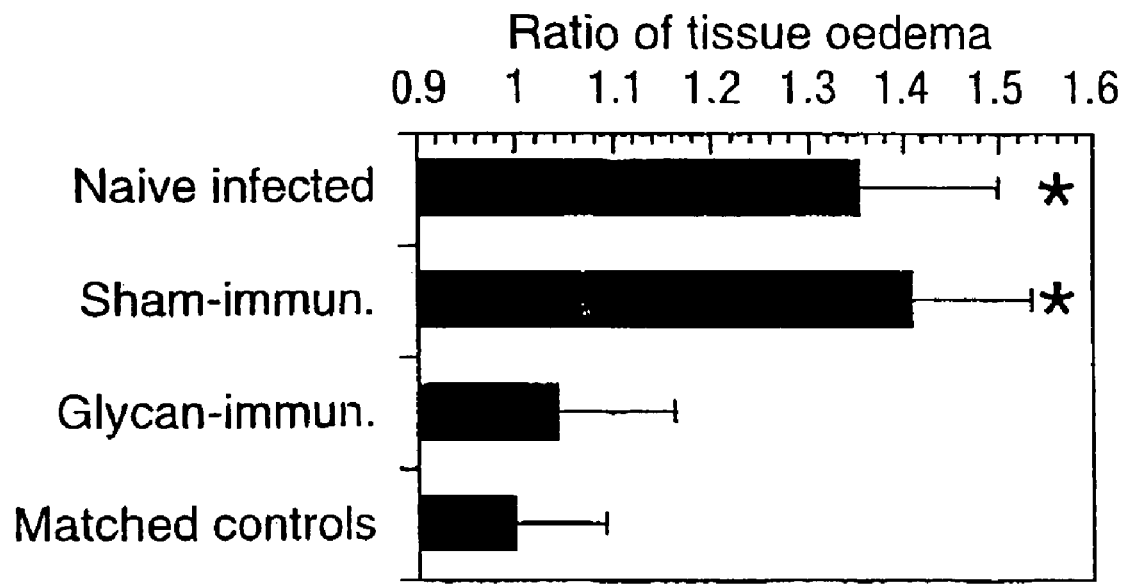
Figure 15:
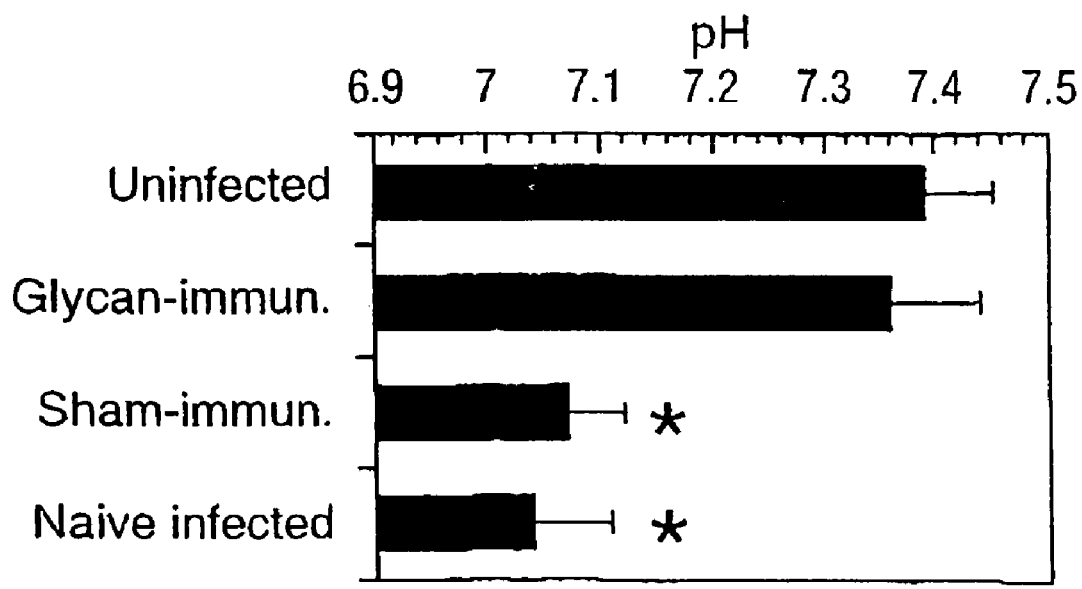

The murine *P. berghei* ANKA severe malaria model has salient features in common with the human severe and cerebral malaria syndromes. It is a TNFα-dependent encephalopathy associated with upregulation of ICAM-1 on the cerebral microvascular endothelium and attendant neurological complications (Grau, G. E., (1987) *Science* 237:1210-1212; Grau, G. E. et al. (1989) *Proc. Natl. Acad. Sci. USA* 86:5572-5574; Grau, G. E. et al. (1991) *Eur. J. Immunol.* 21:2265-2267; Jennings, V. M., Actor, J. K., Lai, A. A. & Hunter, R. L. (1997) *Infect. Immun.* 65:4883-4887). Pulmonary oedema and lactic acidosis are also observed. Unlike most, but not all, human cerebral malaria cases, the blood-brain barrier is compromised in the terminal or agonal stages of the murine syndrome. In the proximal or developmental stages however the murine disease reflects more accurately the cytokine-dependent inflammatory cascade leading to cerebral involvement in humans. Thus early stage *P. berghei* ANKA infection appears the best available small animal model of clinically severe malaria. To determine whether anti-GPI immunization prevents systemic and cerebral pathogenesis in this pre-clinical model, C57B16 mice primed and twice boosted with 6.5 µg KLH-glycan (0.18 µg glycan) or KLH-cysteine in Freund's Adjuvant were challenged with *Plasmodium berghei* ANKA, and the course of disease monitored. 100% of both sham-immunized and naïve control mice died with the cerebral syndrome, showing severe neurological signs including loss of self-righting reflex, ataxia, and hemiplegia, with pronounced hypothermia and occasional haematouria (FIG. 15a). These fatalities were evident early during infection (day 5-8) with relatively low parasitaemias. There were no differences between naïve and sham-immunized mice indicating exposure to carrier protein alone in Freund's Adjuvant does not influence disease rates. In contrast, mice immunized with chemically synthetic *P. falciparum* GPI glycan coupled to KLH were substantially protected against cerebral malaria, with significantly reduced death rates (75% survival, p<0.02, FIG. 15a). In four separate additional experiments, results over the range of 58.3-75% survival over this time period in vaccine recipients (n=50 total) vs. 0-8.7% survival in sham-immunized controls (n=85) were obtained. Parasitaemias were not significantly different between test and control groups in these experiments, demonstrating that prevention of fatality by anti-GPI vaccination does not operate through effects on parasite replication (FIG. 15b). The diagnoses of cerebral malaria, or absence of this condition, were confirmed by histological examination of brains taken at day 6 post-infection. Sham-immunized mice showed typical pathology including high levels of vascular occlusion with both parasitized RBCs and host leukocytes (FIG. 15c). Immunized animals in contrast showed absent or much reduced vascular occlusion despite similar parasite burdens (FIG. 15c).

Severe malaria in both humans and rodents may be associated with additional organ-specific and systemic derangements, including pulmonary oedema and serum acidosis. Acidosis may be a prime pathophysiological process and is the strongest single prognostic indicator of outcome. The biochemical aetiology of acidosis is unclear, and may result from several causes including a metabolic consequence of cytokine excess, lactate production by parasites, decrease hepatic clearance of lactate, tissue hypoxia and respiratory insufficiency. The relationship to human malarial acidosis of that in the rodent model also remains to be elucidated. Nonetheless, it was sought to determine whether anti-GPI vaccination protects against these additional non-cerebral disease syndromes in mice. Both sham-immunized and naïve individuals developed pronounced pulmonary oedema by day 6 post-infection, as measured by lung dry:wet weight ratios, and this was markedly reduced in vaccine recipients (FIG. 15d). Similarly, whereas sham-immunized and unimmunized mice developed significant acidosis as shown by reduced blood pH at day 6 post-infection, in vaccinated mice blood pH was maintained at physiological levels (FIG. 15e). As parasite burdens were similar in test and control groups, production of lactic acid by parasite biomass, and any mild haemolytic anaemia consequence upon parasitaemia at this stage, are not major contributors to acidosis in this model. Clearly however, immunizing against GPI prevents the development of pulmonary oedema and acidosis as well as cerebral malaria in *P. berghei* infection.

The experiments undertaken for this study were designed to test the hypothesis that GPI is implicated in the malarial inflammatory cascade and in metabolic derangement, and to determine whether vaccination against this target affords clinical protection in the best small animal model available. Mice were primed and boosted with 176 ng glycan per dose, which may be a sub-optimal quantity. Systematic optimization with respect to formulation, carrier/hapten ratios, adjuvants, dosage or timing of the immunization regimen would be a matter of routine procedure to the person of skill in the art. Therefore it is possible that the degree of protection against disease observed here may be improved further pursuant to such routine optimisation. Similarly, anti-GPI vaccination may conceivably be beneficial in other malarial disease syndromes not sufficiently modeled by acute *P. berghei* ANKA infection.

In areas of high transmission, immunity to malaria is acquired in two stages: after two to three years of susceptibility to severe and lethal disease, children developed an acquired clinical immunity which protects against life-threatening pathology despite persistent high parasitaemias (Christophers, S. R. (1924) *Ind. J. Med. Res.* 12:273-294; Sinton, J. A. (1939) *Journal of the Malaria Institute of India* 2:71-83; McGregor, I. A., Gilles, H. M., Walters, J. H., Davies, A. H. and Pearson, F. A. (1956) *Br. Med. J* 2:686-692). The chemical synthesis of GPI fragments reported here should aid in serological investigations and the epitope mapping of human anti-GPI antibodies.

In contrast to acquired clinical immunity, anti-parasite immunity takes many more years to develop (McGregor et al (1956), supra) and is easily lost, reflecting the problems of antigenic diversity, antigenic variation, redundancy in invasion pathways, immune evasion strategies and problems of MHC-linked genetic restriction in the immune response to parasite antigens. Current approaches to anti-malarial vaccines seek to induce anti-parasite immunity through parasiticidal mechanisms targeted to parasite protein antigens. The public health potential of anti-disease vaccines is demonstrated by the highly effective tetanus and diphtheria toxoid vaccines which protect against the most injurious consequences of infection by targeting bacterial toxins (Schofield, F. (1986) *Rev. Infect. Dis.* 8:144-156). The findings of this study demonstrate that GPI is the dominant endotoxin of malaria parasite origin. A non-toxic GPI oligosaccharide coupled to carrier protein is immunogenic and provides significant protection against malarial pathogenesis and fatalities in a preclinical rodent model. It is therefore possible that GPI contributes to life-threatening disease in human malaria. These data suggest that an anti-toxic vaccine against malaria might be feasible and that synthetic fragments of the *P. falciparum* GPI may be developed further to that end.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more said steps or features.

BIBLIOGRAPHY

Bate, C. A. W., and Kwiatkowski, D. (1994) *Infection and Immunity* 62:5261-5266.
Bate, C. A. W., Taverne, J., and Playfair, J. H. L. (1992c) *Infection and Immunity* 60:1894-1901.
Bate, C. A., Taverne, J., and Playfair, J. H. (1989) *Immunology* 66:600.
Bate, C. A., Taverne, J., and Playfair, J. H. (1988) *Immunology* 64:227.
Bate, C. A., Taverne, J., Roman, E., Moreno, C., and Playfair, J. H. L. (1992a) *Immunology* 75:129-135.
Bate, C. A. W., Taverne, J., Kwiatkowski, D., and Playfair, J. H. L. (1993) *Immunology* 79:138-145.
Bate, C. A. W., Taverne, J., Bootsma, H. J., Mason, R. C. S. H., Skalko, N., Gregoriadis, G., and Playfair, J. H. L. (1992b) *Immunology* 76:3541.
Berendt, A. R., Turner, G. D. H. and Newbold, C. I. (1994) *Parasitol Today* 10:412.
Berhe, S., Schofield, L., Schwarz, R. T. & Gerold, P. (1999) *Mol. Biochem. Parasitol.* 103:273-278.
Christophers, S. R. (1924) *Ind. J. Med. Res.* 12:273-294.
Clark, I. A. (1978) *Lancet* 2:75.
Clark, I. A., Virelizier, J.-L., Carswell, B. A., and Wood, P. R. (1981) *Infect. Immun.* 32:1058.
Dieckmann-Schuppert, A., Bender, S., Odenthal-Schnittler, M., Bause, E. & Schwarz, R. T. (1992) *Eur. J. Biochem.* 205:815-825.
Dieckmann-Schuppert, A., Bause, E. & Schwarz, R. T. (1993) *Eur. J. Biochem.* 216:779-788.
Gardsvoll, H., Dano, K., and Ploug, M., (1999), *J Biol Chem*, 274(53):37995-38003
Gerold, P., Schofield, L., Brackman M., Holder, A. A., Schwarz, R. T. (1996) *Mol. Biochem. Parasitol* 75:131.
Gerold, P., Dieckman-Schuppert A. and Schwarz, R. T. (1992) *Bio. Soc. Trans.* 29:297.
Gerold, P., Dieckmann-Schuppert, A. & Schwarz, R. T. (1994) *J. Biol. Chem.* 269:2597-2606.
Golgi, C. (1886) *Arch. Sci. med. (Torino)* 10:109.
Gowda, D. C., Gupta, P. & Davidson, E. A. (1997) *J. Biol. Chem.* 272:6428-6439.
Grau, G. E. et al. (1987) *Science* 237:1210-1212.
Grau, G. E. et al. (1989) *Proc. Natl. Acad. Sci. USA* 86:5572-5574.
Grau, G. E. et al. (1991) *Eur. J. Immunol.* 21:2265-2267.
Hoyer-Hansen, G., Behrendt, N., Ploug, M., Dano, K., and Preissner, K. T., (1997), *FEBS Lett*, 420(1):79-85
Jakobsen, P. H., Morris-Jones, S. D., Hviid, L., Theander, T. G., Hoier-Madsen, M., Bayoumi, R., and Greenwood, B. M. (1993b) *Immunology* 79:653-657.
Jennings, V. M., Actor, J. K. Lai, A. A. & Hunter, R. L. (1997) *Infect. Immun.* 65:4883-4887.
McConville, M. J. and Ferguson M. A. (1993), *Biochem. J.* 294:305.
McGregor, I. A., Gilles, H. M., Walters, J. H., Davies, A. H. & Pearson, F. A. (1956) *Br. Med. J.* 2:686-692.
Moore, A., Basilion, J., Chiocca, E., and Weissleder, R., (1988) *BBA*, 1402:239-249.
Naik, R. S. et al. (2000) *J. Exp. Med.* 192:1563-1576.
Navaza, J., (1994), *Acta Cryst, A*50:157-163.
Playfair, J. H. L. (1994) *Immunology Letters* 43:83-86.
Ploug, M., (1998), *Biochemistry*, 37(47):16494-16505
Ploug, M., Ostergaard, S., Hansen, L. B., Holm, A., and Dano, K., (1998), *Biochemistry*, 37(11):3612-3622
Ploug, M., Rahbek-Nielsen, H., Ellis, V., Roepstorff, P., and Dano, K., (1995), *Biochemistry*, 34(39):12524-12534
Ploug, M., Ellis, V., and Dano, K., (1994), *Biochemistry*, 33(30):8991-8997
Schofield, F. (1986) *Rev. Infect. Dis.* 8:144-156.
Schofield, L., Novakovic, S., Gerold, P., Schwarz, R. T., McConville, M. J. and Tachado, S. D. (1996) *J. Immunol.* 156:1886-1896.
Schofield, L., and Hackett, F. (1993) *Journal of Experimental Medicine* 177:145-153.
Shenoy-Scaria, A. M., Kwong, J., Fujita, T., Olszowy, M. W., Shaw, A. S., and Lublin, D. M. (1992) *Journal of Immunology* 149:3535-3541.
Sinton, J. A. (1939) *Journal of the Malaria Institute of India* 2:71-83.
Stefanova, I., Corcoran, M. L., Horak, E. M., Wahl, L. M., Bolen, J. B., and Horak, I. D. (1993) *Journal of Biological Chemistry* 268:20725-20728.
Stephens, R. W., Bokman, A. M., Myohanen, H. T., Reisberg, T., Tapiovaara, H., Pedersen, N., Grondahl-Hansen, J., Llinas, M., and Vaheri, A., (1992), *Biochemistry*, 31:7572-7579
Stevens, V. L. (1995) *Biochem. J.* 310:361.
Tachado, S. D. & Schofield. L. (1994) *Biochem. Biosphys. Res. commun.* 205:984-991.
Tachado, S. D., Gerold, P., McConville, M. J., Baldwin, T., Quilici, D., Schwarz, R. T., and Schofield, L. (1996) *Journal of Immunology* 156:1897-1907.
Tachado, S. D., Gerold, P., Schwarz, R., Novakovic, S., McConville, M., and Schofield, L. (1997) *Proceedings of the National Academy of Sciences USA* 94:4022-4027.
Weissleder, R., Moore, A., Ph.D., Mahmood-Bhorade, U., Benveniste, H., Chiocca, E. A., Basilion, (2000) J. P. *Nature Medicine,* 6:351-355.
Xia, M.-Q., Hale, G., Lifely, M. R., Ferguson, M. A. J., Campbell, D., Packman, L., and Waldmann, H. (1993) *Biochemical Journal* 293:633-640.

The invention claimed is:

1. A method of eliciting or inducing, in a mammal, an immune response directed to a parasite said method comprising administering to said mammal an effective amount of an immunogenic composition, which composition comprises the inositolglycan domain portion of GPI, which inositolglycan domain portion comprises insufficient lipidic domain to induce or elicit an immune response directed to said lipidic domain and which has a terminal inositol-phosphoglycerol substituted with a positively or negatively charged moiety.

2. A method of therapeutically or prophylactically treating a mammal for a parasite infection said method comprising administering to said mammal an effective amount of an immunogenic composition which composition comprises the inositolglycan domain portion of GPI, which inositolglycan domain portion comprises insufficient lipidic domain to induce or elicit an immune response directed to a GPI lipidic domain and which has a terminal inositol-phosphoglycerol substituted with a positively or negatively charged moiety.

3. A method for the treatment and/or prophylaxis of a mammalian disease condition caused by a parasite infection, said method comprising administering to said mammal an effective amount of an immunogenic composition which composition comprises the inositolglycan domain portion of GPI, which inositolglycan domain portion comprises insufficient lipidic domain to induce or elicit an immune response directed to said lipidic domain and which has a terminal inositol-phosphoglycerol substituted with a positively or negatively charged moiety.

4. The method according to claim 1, 2 or 3 wherein said parasite is *Plasmodium*.

5. The method according to claim 4 wherein said *Plasmodium* is *Plasmodium falciparum*.

6. The method according to claim 5 wherein said GPI molecule is a *Plasmodium falciparum* GPI inositolglycan domain.

7. The method according to claim 6 wherein said GPI inositolglycan domain is synthetically generated.

8. The method according to claim 7 wherein said GPI inositolglycan domain comprises the structure EtN-P-(Man$\alpha$1,2)-6Man$\alpha$1, 2Man$\alpha$1, 6Man$\alpha$1, 4GlcNH$_2$$\alpha$1-myo-inositol-1,2 cyclic-phosphate wherein EtN is ethanolamine, P is phosphate and M is mannose.

9. The method according to claim 7 wherein said GPI inositolglycan domain comprises the structure NH$_2$—CH$_2$—CH$_2$—PO$_4$-(Man$\alpha$1-2) 6Man$\alpha$1-2 Man$\alpha$1-6Man$\alpha$1-4GlcNH$_2$-6myo-inositol-1,2 cyclic-phosphate.

10. The method according to claim 3 wherein said disease condition is malaria.

11. A composition capable of inducing an immune response directed to a parasite said composition comprising a parasite GPI inositolglycan domain portion but which portion is incapable of inducing an immune response to a lipidic domain of a GPI and which has a terminal inositol-phosphoglycerol substituted with a positively or negatively charged moiety.

12. A vaccine composition for inducing an immune response to a parasite, said composition comprising as the active component the parasite inositolglycan domain portion of GPI, which inositolglycan portion is incapable of inducing an immune response directed to a lipidic domain of a GPI and which has a terminal inositol-phosphoglycerol substituted with a positively or negatively charged moiety, together with one or more pharmaceutically acceptable carriers and/or diluents.

13. A pharmaceutical composition comprising a parasite GPI inositolglycan domain portion but which portion is incapable of inducing an immune response directed to a lipidic domain of a GPI and which has a terminal inositol-phosphoglycerol substituted with a positively or negatively charged moiety, together with one or more pharmaceutically acceptable carriers and/or diluents.

14. The composition according to claim 11, 12 or 13 wherein said parasite is *Plasmodium*.

15. The composition according to claim 14 wherein said GPI inositolglycan domain is synthetically generated.

16. The composition according to claim 15 wherein said synthetic GPI inositolglycan domain comprises the structure EtN-P-(Man$\alpha$1,2)-6M$\alpha$1, 2M$\alpha$1, 6Man$\alpha$1, 4GlcNH$_2$$\alpha$1-myo-inositol-1,2 cyclic-phosphate, wherein EtN is ethanolamine, P is phosphate and M is mannose.

17. The composition according to claim 16 wherein said GPI inositolglycan domain comprises the structure NH$_2$—CH$_2$—CH$_2$—PO$_4$-(Man$\alpha$1-2) 6Man$\alpha$1-2Man$\alpha$1-6Man$\alpha$1-4GlcNH$_2$-6myo-inositol-1,2 cyclic-phosphate.

18. A method for detecting, in a biological sample, an immunointeractive molecule directed to a microorganism, said method comprising contacting said biological sample with a molecule comprising a modified GPI inositolglycan domain and qualitatively and/or quantitatively screening for said GPI inositolglycan domain-immunointeractive molecule complex formation.

19. A method for detecting or monitoring an immune response directed to a microorganism in a subject said method comprising contacting a biological sample, from said subject, with a molecule comprising a modified GPI inositolglycan domain which comprises insufficient lipidic domain to induce or elicit an immune response directed to a GPI lipidic domain and which a terminal inositol phosphoglycerol substituted with a positively or negatively charged moiety and qualitatively and/or quantitatively screening for GPI inositolglycan domain-immunointeractive molecule complex formation.

20. The method according to claim 18 or 19 wherein said modified GPI molecule is the inositolglycan domain portion of GPI.

21. The method according to claim 20 wherein said modified GPI molecule is a modified parasite GPI molecule.

22. The method according to claim 21 wherein said parasite is *Plasmodium*.

23. The method according to claim 22 wherein said *Plasmodium* is *Plasmodium falciparum*.

24. The method according to claim 23 wherein said modified *Plasmodium falciparum* GPI molecule is a *Plasmodium falciparum* GPI inositolglycan domain.

25. The method according to claim 24 wherein said GPI inositolglycan domain is synthetically generated.

26. The method according to claim 25 wherein said synthetic GPI inositolglycan domain comprises the structure EtN-P-(Man$\alpha$1,2)-6M$\alpha$1, 2M$\alpha$1, 6Man$\alpha$1, 4GlcNH$_2$$\alpha$1-myo-inositol-1,2 cyclic-phosphate, wherein EtN is ethanolamine, P is phosphate and M is mannose.

27. The method according to claim 26 wherein said synthetic GPI inositolglycan domain comprises the structure NH$_2$—CH$_2$—CH$_2$—PO$_4$-(Man$\alpha$1,2)6M$\alpha$1, 2M$\alpha$1, 6Man$\alpha$1, 4GlcNH$_2$$\alpha$1-myo-inositol-1,2 cyclic-phosphate.

28. The method or composition according to any one of claims 1, 2, 3, 11, 12 or 13 wherein the positively or negatively charged moiety is a hydrophilic moiety.

29. The method according to any one of claims 1, 2, 3, 11, 12 or 13 wherein the positively or negatively moiety comprises a phosphate moiety.

30. The method according to any one of claims 1, 2, 3, 11, 12 or 13 wherein the positively or negatively moiety is inositol-1,2-cyclic phosphate.

31. The method according to claim 18 or 19 wherein the positively or negatively charged moiety is a hydrophilic moiety.

32. The method according to claim 18 or 19 wherein the positively or negatively charged moiety comprises a phosphate moiety.

33. The method according to claim 18 or 19 wherein the positively or negatively charged moiety is inositol-1,2-cyclic phosphate.

34. A modular kit comprising one or more members, wherein at least one member is a solid support comprising a GPI molecule which consists of the *Plasmodium falciparum* GPI inositolglycan domain.

35. A modular kit comprising one or more members, wherein at least one member is a solid support comprising the inositolglycan domain portion of GPI, which inositolglycan domain portion comprises insufficient lipidic domain to induce or elicit an immune response directed to said lipidic domain and which has a terminal inositol-phosphoglycerol substituted with a positively or negatively charged moiety.

36. The modular kit of claim 35, wherein the positively or negatively charged moiety is a hydrophilic moiety.

37. The modular kit of claim 35, wherein the positively or negatively moiety comprises a phosphate moiety.

38. The modular kit of claim 35, wherein the positively or negatively moiety is inositol-1,2-cyclic phosphate.

39. The method of claim 1, wherein said parasite is *Plasmodium*.

40. The method of claim 2, wherein said parasite is *Plasmodium*.

* * * * *